US007709514B2

(12) United States Patent
Morand et al.

(10) Patent No.: US 7,709,514 B2
(45) Date of Patent: May 4, 2010

(54) THERAPEUTIC MOLECULES AND METHODS-1

(75) Inventors: Eric Francis Morand, Elwood (AU); Magdy Naguib Iskander, Sandringham (AU); Basil Danylec, Box Hill North (AU)

(73) Assignee: Cortical Pty Ltd, Victoria (AU)

( * ) Notice: Subject to any disclaimer, the term of this patent is extended or adjusted under 35 U.S.C. 154(b) by 1074 days.

(21) Appl. No.: 10/517,264

(22) PCT Filed: Jun. 6, 2003

(86) PCT No.: PCT/AU03/00717

§ 371 (c)(1),
(2), (4) Date: Sep. 30, 2005

(87) PCT Pub. No.: WO03/104203

PCT Pub. Date: Dec. 18, 2003

(65) Prior Publication Data

US 2006/0154977 A1    Jul. 13, 2006

(30) Foreign Application Priority Data

Jun. 7, 2002   (AU) ................................. PS2832
Jun. 7, 2002   (AU) ................................. PS2834

(51) Int. Cl.
*A61K 31/415* (2006.01)
*C07D 233/00* (2006.01)
(52) U.S. Cl. .................................. 514/385; 548/300.1
(58) Field of Classification Search ................. 514/385; 548/300.1
See application file for complete search history.

(56) References Cited

U.S. PATENT DOCUMENTS

| 2,418,925 A * | 4/1947 | Clapp et al. ............... 548/302.7 |
| 2,843,597 A | 7/1958 | Clark et al. |
| 2,933,503 A | 4/1960 | Clark et al. |
| 3,775,333 A | 11/1973 | Loffelman et al. |
| 4,277,397 A | 7/1981 | Fuchs |
| 4,329,477 A | 5/1982 | Schubart et al. |
| 4,400,319 A | 8/1983 | Hari et al. |

FOREIGN PATENT DOCUMENTS

| DE | 292452 A5 | 8/1991 |
| EP | 0010721 A1 | 5/1980 |
| EP | 0462831 A2 | 12/1991 |
| FR | 2688504 | 9/1993 |
| GB | 876015 | 8/1961 |
| WO | 96/10026 A1 | 4/1996 |
| WO | 99/36402 A1 | 7/1999 |
| WO | 01/44223 A1 | 6/2001 |
| WO | WO 01/44223 A1 | 6/2001 |
| WO | 01/77083 A1 | 10/2001 |
| WO | 01/92239 A1 | 12/2001 |

OTHER PUBLICATIONS

U.S. Appl. No. 12/158,563 (no pg pub available), filing date: Dec. 21, 2006.*
Schacke et al., Expert Opin. THer. Patents, 2008, 18(3), 339-352, especially p. 343.*
STN File HCS, Abstract No. 115:159037 and Kawashima et al., "2, 5, 6-Trichlorobenzimidazole. Synthesis of a Precursor for 2-Substituted 5, 6-Dichlorobenzimidazoles", 1991, Nucleic Acid Chem. vol. 4, pp. 24-26.
STN File HCA Abstract No. 52:77210 and Clark et al., "Synthesis of Some Substituted Benzimidazolinones" 1958, Journal of the American Chemical Society, vol. 80, pp. 1657-1662.
STN File HCA Abstract No. 52:72309 and Efros et al., "Imidazole Derivatives. XVII. Nitration of 5-Methylbenzimidazoles", 1958, Zhurnal Obshchei Khimii, vol. 28, pp. 62-69.
Morand, et al.; "Macrophage Migration Inhibitory Factor"; *Arthritis & Rheumatism*, vol. 48, No. 2, Feb. 2003, pp. 2910-2299.
De Jong, et al.; "Development of chronic colitis is dependent on the cytokine MIF"; *Nature Immunology*, Nov. 2001, vol. 2 No. 11; pp. 1061-1066.
Yu, et al.; "Expression of Macrophage Migration Inhibitory Factor in Acute Ischemic Myocardial Injury"; *The Journal of Histochemistry & Cytochemistry*, vol. 51(5):625-631, 2003.
Kobayashi, et al.; "Prevention of Lethal Acute Hepatic Failure by Antimacrophage Migration Inhibitory Factor Antibody in Mice Treated With Bacille Calmette-Guerin and Lipopolysaccharide"; *Hepatology*, vol. 29, No. 6, 1999, pp. 1752-1759.
He, et al.; "Macrophage Migration Inhibitory Factor Promotes Colorectal Cancer"; *Mol. Med.* 15(1-2) 1-10, Jan.-Feb. 2009.
Calandra, et al.; "Protection from septic shock by neutralization of macrophage migration inhibitory factor"; *Nature Medicine*, vol. 6, No. 2, Feb. 2000, pp. 164-170.
Pan, et al.; "Macrophage Migration Inhibitory Factor Deficiency Impairs Atherosclerosis in Low-Density Lipoprotein Receptor-Deficient Mice"; *Circulation Journal of the American Heart Association*, Mar. 18, 2009; pp. 3149-3153.
Stosic-Grujicic, et al.; "Macrophage Migration Inhibitory Factor (MIF) Is Necessary for Progression of Autoimmune Diabetes Mellitus"; *Journal of Cellular Physiology*; pp. 665-675.
Sanchez, et al.; "Evidence of association of macrophage migration inhibitory factor gene polymorphisms with systemic lupus erythematosus"; *Genes and Immunity* (2006), 1-4.
Magalhaes, et al.; "Macrophage migration inhibitory factor is essential for allergic asthma but not for Th2 differentiation"; *European Journal of Immunology*, 2007, 37: 1097-1106.

(Continued)

*Primary Examiner*—Susannah Chung
(74) *Attorney, Agent, or Firm*—King & Spalding

(57) ABSTRACT

Methods of inhibiting the cytokine or biological activity of Macrophage Migration Inhibitory Factor (MIF) comprising contacting MIF with a compound of formula (I) as defined herein, is provided. The invention also relates to methods of treating diseases or conditions where MIF cytokine or biological activity is implicated comprising administration of compounds of formula (I), either alone or as part of a combination therapy. Novel heterocyclic compounds are also provided for.

12 Claims, 12 Drawing Sheets

OTHER PUBLICATIONS

Chesney, et al.; "An Essential Role for Macrophage Migration Inhibitory Factor (MIF) in Angiogenesis and the Growth of a Murine Lymphoma"; *Moledular Medicine* 5: 181-191, 1999.

Shimizu, et al.; "High Macrophage Migration Inhibitory Factor (MIF) Serum Levels Associated with Extended Psoriasis"; *The Society for Investigative Dermatology, Inc.*, pp. 989-990.

Denkinger, et al., "In Vivo Blockade of Macrophage Migration Inhibitory Factor Ameliorates Actue Experimental Autoimmune Encephalomyelitis by Impairing the Homing of Encephalitogenic T Cells to the Central Nervous System"; *The Journal of Immunology*; pp. 1274-1282.

Meyer-Siegler, et al.; "Further evidence for increased macrophage migration inhibitory factor expression in prostate cancer"; *BMC Cancer* 2005, 5:73; pp. 1-12.

Onodera, et al.; "Transgenic Mice Overexpressing Macrophage Migration Inhibitory Factor (MIF) Exhibit High-Turnover Osteoporosis"; *Journal of Bone and Mineral Research*; vol. 21, No. 6, 2006, pp. 876-885.

Lan, et al.; "The Pathogenic Role of Macrophage Migration Inhibitory Factor in Immunologically Induced Kidney Disease in the Rat"; *J. Exp. Med.*, vol. 185, No. 8, Apr. 21, 1997, pp. 1455-1465.

Hardman, et al.; "Macrophage Migration Inhibitory Factor, A Central Regulator of Wound Healing"; *American Journal of Pathology*, vol. 167, No. 6, Dec. 2005, pp. 1561-1574.

Martin, et al.; "Macrophage migration inhibitory factor (MIF) plays a critical role in pathogenesis of ultraviolet-B (UVB)-induced nonmelanoma skin cancer (NMSC)"; *The FASEB Journal*, vol. 23, Mar. 2009, pp. 720-730.

Rendon, et al.; "Regulation of Human Lung Adenocarcinoma Cell Migration and Invasion by Macrophage Migration Inhibitory Factor"; *Journal of Biological Chemistry*, vol. 282, No. 41, Oct. 12, 2007, pp. 29910-29918.

Shimizu, et al.; "High Expression of Macrophage Migration Inhibitory Factor in Human Melanoma Cells and Its Role in Tumor Cell Growth and Angiogenesis"; *Biochemical and Biophysical Research Communications* 264, 751-758 (1999).

Shun, et al.; "Expression of macrophage migration inhibitory factor is associated with enhanced angiogenesis and advanced stage in gastric carcinomas"; *World Journal of Gastroenterology* 2005: 11(24)-3767-3771.

Ren, et al.; "Macrophage Migration Inhibitory Factor: Roles in Regulating Tumor Cell Migration and Expression of Angiogenic Factors in Hepatocellular Carcinoma"; *Int. J. Cancer*: 107, 22-29 (2003).

Nunez, et al.; "Involvement of macrophage migration inhibitory factor gene in celiac disease susceptibility"; *Genes and Immunity* (2007) 8, 168-170.

Xu, et al.; "Overexpression of macrophage migration inhibitory factor induces angiogenesis in human breast cancer"; *Cancer Letters* 261 (2008) 147-157.

Selvi, et al.; "Expression of macrophage migration inhibitory factor in diffuse systemic sclerosis"; *Ann Rheum Dis* 2003; 62:460-464.

Berdeli, et al.; "Association of macrophage migration inhibitory factor -173C allele polymorphism with steriod resistance in children with mephrotic syndrome"; *Pediatr Nephrol* (2005) 20:1566-1571.

De Benedetti, et al.; "Functional and Prognostic Relevance of the -173 Polymorphism of the Macrophage Migration Inhibitory Factor Gene in Systemic-Onset Juvenile Idiopathic Arthritis"; *Arthritis & Rheumatism* vol. 48, No. 5, May 2003, pp. 1398-1407.

Kotake, et al.; "Macrophage Migration Inhibitory Factor in Uveitis"; pp. 99-103.

Tashimo, et al.; "Aqueous levels of macrophage migration inhibitory factor and monocyte chemotactic protein-1 in patients with diabetic retinopathy"; 2004 *Diabetic Medicine*, 21 1292-1297.

Hagemann, et al.; "Ovarian cancer cell-derived migration inhibitory factor enchances tumor growth, progression, and angiogenesis"; *Mol Cancer Ther* 2007;6(7), Jul. 2007.

Meyer-Siegler, et al.; "Inhibition of macrophage migration inhibitory factor decreases proliferation and cytokine expression in bladder cancer cells"; *BMC Cancer* 2004, 4:34, pp. 1-12.

Nakamaur, et al.; "Prognostic significance of cytoplasmic macrophage migration inhibitory factor expression in patients with squamous cell carcinoma of the head and neck treated with concurrent chemoradiotherapy"; *Oncol Rep*, Jan. 2005;13(1):59-64.

Ren, et al.; "Macrophage Migration Inhibitory Factor Stimulates Angiogenic Factor Expression and Correlates With Differentiation and Lymph Node Status in Patients With Esophageal Squamous Cell Carcinoma"; *Annals of Surgery*, vol. 242, No. 1, Jul. 2005, pp. 55-63.

* cited by examiner

THERAPEUTIC MOLECULES AND METHODS-1

FIELD OF THE INVENTION

The present invention relates generally to the treatment of diseases or conditions resulting from cellular activation, such as inflammatory or cancerous diseases or conditions. In particular, the invention relates to the use of heterocyclic derivatives to inhibit the cytokine or biological activity of macrophage migration inhibitory factor (MIF), and diseases or conditions wherein MIF cytokine or biological activity is implicated.

BACKGROUND OF THE INVENTION

MIF is the first identified T-cell-derived soluble lymphokine. MIF was first described as a soluble factor with the ability to modify the migration of macrophages (1). The molecule responsible for the biological actions ascribed to MIF was identified and cloned in 1989 (2). Initially found to activate macrophages at inflammatory sites, it has been shown to possess pluripotential actions in the immune system. MIF has been shown to be expressed in human diseases which include inflammation, injury, ischaemia or malignancy. MIF also has a unique relationship with glucocorticoids by overriding their anti-inflammatory effects.

Recent studies have indicated that monoclonal antibody antagonism of MIF may be useful in the treatment of sepsis, certain types of cancers and delayed type hypersensitivity. Antibody antagonism of MIF has also been shown to have activity in adjuvant- or collagen-induced arthritis animal models and other models of inflammatory and immune diseases.

Although antibody antagonism of MIF is one potential way to provide therapeutic treatments, such biological molecules can be expensive to prepare on a commercial basis and further, can be limited in the way they are administered (generally by injection) and do not readily lend themselves to formulations for administration by other means eg oral administration.

Small molecule inhibitors may overcome one or more such difficulties connected with the use of biological therapeutic treatments. There exists a need, therefore, for small molecule inhibitors of the cytokine or biological activity of MIF. Small molecule inhibitors of the MIF would have therapeutic effects in a broad range of diseases, whether given alone or in combination with other therapies.

Examples of agents which could be used in combination with a compound of formula (I) include glucocorticoids, anti-rheumatic drugs, immunosuppressive drugs, anti-cytokine therapies, antagonists or inhibitors of nitrogen-activated protein (MAP) kinases, antagonists or inhibitors of nuclear factor kappa-B (NF-κB) signal transduction pathway, antibodies, protein therapeutics or small molecule therapeutics interacting with adhesion molecules and co-stimulatory molecules, bronchodilators, antagonists of eicosanoid synthesis pathways, agents used for the treatment of inflammatory bowel disease, anti-cancer drugs, antisense oligonucleotides, interfering RNA and ribozymes.

For example, glucocorticoids have been used to treat human diseases for over fifty years and are effective in a range of diseases which include inflammation, injury, ischaemia or malignancy. Although debate continues in relation to their impact on disease prognosis, their influence on symptoms and signs of inflammation, especially in the short term, can be dramatic.

Despite their benefits and efficacy, the use of glucocorticoids is limited by universal, predictable, dose-dependent toxicity. Mimicking Cushing's disease, a disease wherein the adrenal glands produce excess endogenous glucocorticoids, glucocorticoid treatment is associated with side effects including immunosuppression (resulting in increased susceptibility to infections), weight gain, change in body habitus, hypertension, oedema, diabetes mellitus, cataracts, osteoporosis, poor wound healing, thinning of the skin, vascular fragility, hirsutism and other features of masculinization (in females). In children, growth retardation is also noted. These side effects are known as Cushingoid side effects.

Since the side effects of glucocorticoids are dose dependent, attempts to reduce the dosage requirement have been investigated, including combination therapies in which glucocorticoids are administered with other therapeutic agents. These combination therapies are sometimes referred to as "steroid-sparing" therapies. However, currently available combination therapies are non-specific as the other therapeutic agents do not address biological events which inhibit the effectiveness of glucocorticoids. Such combination therapies are also typically associated with serious side effects.

Furthermore, glucocorticoids are incompletely effective in a number of disease settings, leading to the concept of "steroid-resistant" diseases. Agents which amplify or enhance the effects of glucocorticoids would not only allow the reduction of dose of these agents but may also potentially render "steroid-resistant" diseases steroid-sensitive.

There is a need for effective therapies which enable a reduction in the dosage level of glucocorticoids. There is also a need for effective treatment of "steroid-resistant" diseases. Preferably, such therapies or treatments would address factors which directly limit the effectiveness of glucocorticoids.

Therapeutic antagonism of MIF may provide "steroid-sparing" effects or be therapeutic in "steroid-resistant" diseases. Unlike other pro-inflammatory molecules, such as cytokines, the expression and/or release of MIF can be induced by glucocorticoids (3), (4). Moreover, MIF is able to directly antagonize the effects of glucocorticoids. This has been shown to be the case for macrophage TNF, IL-1β, IL-6 and IL-8 secretion (5), (6), and for T cell proliferation and IL-2 release (7). In vivo, MIF exerts a powerful glucocorticoid-antagonist effect in models including endotoxic shock and experimental arthritis (5), (8). In the context of an inflammatory or other disease treated with glucocorticoids, then, MIF is expressed but exerts an effect which prevents the glucocorticoid inhibition of inflammation. It can therefore be proposed that therapeutic antagonism of MIF would remove MIF's role in inhibiting the anti-inflammatory effect of glucocorticoids, thereby allowing glucocorticoids to prevail. This would be the first example of true "steroid-sparing" therapy. In support of this hypothesis is the observation that anti-MIF antibody therapy reverses the effect of adrenalectomy in rat adjuvant arthritis (9). By neutralizing the natural glucocorticoid 'counter-regulator' effect of MIF, it is envisioned that with MIF antagonism, steroid dosages could be reduced or even eliminated in inflammatory disease, particularly in those diseases that are associated with the glucocorticoid resistance (10), (11). There is a need, therefore, for therapeutic antagonists of the cytokine or biological activity of MIF.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

In a first aspect, the present invention provides a method of inhibiting cytokine or biological activity of MIF comprising contacting MIF with a cytokine or biological activity inhibiting effective amount of a compound of formula (I), or a pharmaceutically acceptable salt or prodrug thereof

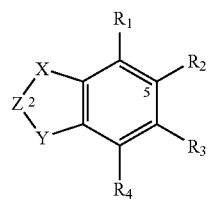

wherein

X is selected from —O—, —S—, —C($R_5$)($R_{5'}$)— or —N($R_6$)— and preferably comprises a hydrogen bond donor or acceptor;

Y is selected from —N($R_7$)—, —O—, —S— or —C($R_7$)$_2$—;

Z is selected from —C(O)—, —C(S)—, —C(=N$R_6$)—, —S(O)— or —S(O)$_2$—;

$R_1$ is selected from hydrogen, $C_{1-3}$alkyl, $(CR_5R_{5'})_nOR_7$, $(CR_5R_{5'})_nSR_7$, $(CR_5R_{5'})_nN(R_6)_2$ and $(CR_5R_{5'})_n$halo;

$R_2$ is selected from $C_1$-$C_{20}$alkyl, $C_2$-$C_{20}$alkenyl, $C_2$-$C_{20}$alkynyl, $(CR_{12}R_{12'})_mC(O)R_8$, $(CR_{12}R_{12'})_mC(S)R_8$, $(CR_{12}R_{12'})_mS(O)_2$, $(CR_{12}R_{12'})_mS(O)_2R_8$, $(CR_{12}R_{12'})_mOR_9$, $(CR_{12}R_{12'})_mSR_9$, $(CR_{12}R_{12'})_mNR_{10}R_{11}$, $(CR_{12}R_{12'})_mC(=NR_{24})R_{22}$ and $(CR_{12}R_{12'})_mR_{13}$;

$R_3$ is selected from hydrogen, $C_1$-$C_6$alkyl, $(CR_{16}R_{16'})_pNR_{14}R_{15}$, $(CR_{16}R_{16'})_pOR_{17}$, $(CR_{16}R_{16'})_pSR_{17}$, $(CR_{16}R_{16'})_p$halo, $(CR_{16}R_{16'})_pNO_2$, $(CR_{16}R_{16'})_nC(O)R_{28}$, $(CR_{16}R_{16'})_nC(=NR_{24})R_{22}$, $(CR_{16}R_{16'})_nS(O)R_{17}$, $(CR_{16}R_{10'})_nS(O)_2R_{17}$, $(CR_{16}R_{16'})_nS(O)_3R_{17}$ and $(CR_{16}R_{16'})_pC(R_{18})_3$;

$R_4$ is selected from hydrogen, halogen $C_1$-$C_3$alkyl, $C_{2-3}$alkenyl, $C_{2-3}$alkynyl and $(CR_{12}R_{12'})_nC(R_{18})_3$;

Each $R_5$ and $R_{5'}$ is independently selected from hydrogen, $C_1$-$C_3$alkyl, halo, $OR_7$, $SR_7$ and $N(R_6)_2$;

Each $R_6$ is independently selected from hydrogen, $C_1$-$C_3$alkyl and $OR_7$;

Each $R_7$ is independently selected from hydrogen and $C_1$-$C_3$alkyl;

$R_8$ is selected from hydrogen, $C_1$-$C_{20}$allyl, $C_2$-$C_{20}$alkenyl, $C_2$-$C_{20}$alkynyl, $OR_{19}$, $SR_{19}$, $N(R_{20})_2$, [NH—CH($R_{21}$)—C(O)]$_q$—$OR_{29}$, [sugar]$_q$ and $(CR_{12}R_{12'})_tR_{13}$;

$R_9$ is selected from hydrogen, $C_1$-$C_{20}$alkyl, $C_2$-$C_{20}$alkenyl, $C_2$-$C_{20}$alkynyl, $(CR_{12}R_{12'})_tR_{13}$, $C(O)R_{23}$, $CO_2R_{23}$, $C(S)R_{23}$, $C(S)OR_{23}$, $S(O)R_{23}$, $S(O)_2R_{23}$, [C(O)CH($R_{21}$)NH]$_q$—$R_{23}$ and [sugar]$_q$;

$R_{10}$ and $R_{11}$ are independently selected from hydrogen, $C_1$-$C_{20}$alkyl, $C_2$-$C_{20}$alkenyl, $C_2$-$C_{20}$alkynyl, $(CR_{12}R_{12'})_m R_{13}$, $C(O)R_{23}$, $C(S)R_{23}$, $S(O)R_{23}$, $S(O)_2R_{23}$, [C(O)CH($R_{21}$)NH]$_q$—$R_{23}$, -[sugar]$_q$ and NHC(=N$R_{25}$)—NH$_2$;

Each $R_{12}$ and $R_{12'}$ is independently selected from hydrogen, $C_1$-$C_6$alkyl, $C_2$-$C_6$alkenyl, $C_2$-$C_6$alkynyl, $OR_{24}$, $SR_{24}$, halo, $N(R_{24})_2$, $CO_2R_{24}$, CN, $NO_2$, aryl or heterocyclyl;

$R_{13}$ is selected from $OR_{25}$, $SR_{25}$, halo, $N(R_{25}$, $C(O)R_{31}$, CN, $C(R_{18})_3$, aryl or heterocyclyl;

$R_{14}$ and $R_{15}$ are independently selected from hydrogen, $C_1$-$C_3$alkyl, $OR_{17}$, $(CR_{16}R_{16'})_pC(R_{18})_3$;

Each $R_{16}$ and $R_{16'}$ is independently selected from hydrogen, $C_1$-$C_3$alkyl, halo, $OR_{17}$, $SR_{17}$ and $N(R_{17})_2$;

Each $R_{17}$ is independently selected from hydrogen and $C_1$-$C_3$alkyl;

Each $R_{18}$ is independently selected from hydrogen and halo;

$R_{19}$ and each $R_{20}$ are independently selected from hydrogen, $C_1$-$C_{20}$alkyl, $C_2$-$C_{20}$alkenyl, $C_2$-$C_{20}$alkynyl, $(CR_{26}R_{26'})_tR_{27}$;

$R_{21}$ is the characterising group of an amino acid;

$R_{22}$ is selected from $C_1$-$C_6$alkyl, $NH_2$, NH($C_{1-6}$alkyl), N($C_{1-6}$alkyl)$_2$, $OR_{29}$ or $SR_{29}$;

$R_{23}$ is selected from hydrogen, $C_1$-$C_{20}$alkyl, $C_2$-$C_{20}$alkenyl, $C_2$-$C_{20}$alkynyl, aryl $(CR_{26}R_{26'})_tR_{27}$;

Each $R_{24}$ is independently selected from hydrogen and $C_1$-$C_6$alkyl;

Each $R_{25}$ is independently selected from hydrogen, $C_1$-$C_6$alkyl, $C_{1-3}$alkoxy$C_{1-3}$alkyl, aryl and heterocyclyl;

Each $R_{26}$ and $R_{26'}$ is independently selected from hydrogen, $C_1$-$C_6$alkyl, $C_2$-$C_6$alkenyl, $C_2$-$C_6$alkynyl, $OR_{29}$, $SR_{29}$, halo, $N(R_{29})_2$, $CO_2R_{29}$, CN, $NO_2$, aryl and heterocyclyl;

$R_{27}$ is selected from hydrogen, $OR_{30}$, $SR_{30}$, halo, $N(R_{30})_2$, $CO_2R_{30}$, aryl and heterocyclyl;

$R_{28}$ is selected from hydrogen, $C_{1-6}$alkyl, $OR_{29}$, $SR_{29}$ or $N(R_{29})_2$;

Each $R_{29}$ is independently selected from hydrogen and $C_1$-$C_3$alkyl;

Each $R_{30}$ is independently selected from hydrogen, $C_1$-$C_3$alkyl, aryl and heterocyclyl;

$R_{31}$ is selected from $C_{1-3}$alkyl, OH, $C_{1-3}$alkoxy, aryl, aryloxy, heterocyclyl and heterocyclyloxy;

n is 0 or an integer from 1 to 3;

m is 0 or an integer from 1 to 20;

p is 0 or an integer from 1 to 6;

q is an integer from 1 to 5;

t is an integer from 1 to 10;

wherein alkyl, alkenyl, alkynyl, aryl and heterocyclyl may be optionally substituted.

In another aspect, the invention provides a method of treating, preventing or diagnosing a disease or condition wherein MIF cytokine or biological activity is implicated comprising the administration of a treatment, prevention or diagnostic effective amount of a compound of formula (I) or a pharmaceutically acceptable salt or prodrug thereof to a subject in need thereof.

In a further aspect, there is provided the use of a compound of formula (I) or a pharmaceutically acceptable salt or prodrug thereof in the manufacture of a medicament for the treatment, prevention or diagnosis of a disease or condition wherein MIF cytokine or biological activity is implicated.

In particular, the invention provides a method of treating, diagnosing or preventing autoimmune diseases, solid or haemopoeitic tumours, or chronic or acute inflammatory diseases, including a disease or condition selected from the group comprising:

Rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, connective tissue diseases (including but not limited to systemic lupus erythematosus, systemic sclerosis, polymyositis, dermatomyositis, Sjögren's syndrome), vasculitides (including but not limited to polyarteritis nodosa, Wegener's granulomatosis, Churg-Strauss syndrome), glomerulonephritis, interstitial nephritis, inflammatory bowel disease (including but not limited to ulcerative colitis, Crohn's disease), peptic ulceration, gastritis, oesophagitis, liver disease (including but not limited to cirrhosis, hepatitis), autoimmune diseases (including but not limited to diabetes mellitus, thyroiditis, myasthenia gravis, sclerosing cholangitis, primary biliary cirrhosis), pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome), cancers whether primary or metastatic (including but not limited to colon cancer, lymphoma, lung cancer, melanoma, prostate cancer, breast cancer, stomach cancer, leukemia, cervical cancer, multiple myeloma and metastatic cancer), atherosclerosis (eg ischaemic heart disease, myocardial infarction, stroke, peripheral vascular disease), disorders of the hypothalamic-pituitary-adrenal axis, brain disorders (eg dementia, Alzheimer's disease, multiple sclerosis, demyelinating diseases), corneal disease, iritis, iridocyclitis, cataracts, uveitis, sarcoidosis, diseases characterised by modified angiogenesis (eg diabetic retinopathy, rheumatoid arthritis, cancer), endometrial function (menstruation, implantation, parturition, endometriosis), psoriasis, endotoxic (septic) shock, exotoxic (septic) shock, infective (true septic) shock, other complications of infection, pelvic inflammatory disease, transplant rejection, allergies, allergic rhinitis, bone diseases (eg osteoporosis, Paget's disease), atopic dermatitis, UV(B) induced dermal cell activation (eg sunburn, skin cancer), malarial complications, diabetes mellitus, pain, inflammatory consequences of trauma or ischaemia, testicular dysfunctions and wound healing, comprising the administration of a treatment, diagnosis or prevention effective amount of a compound of formula (I) or a pharmaceutically acceptable salt or prodrug thereof to a subject in need thereof.

A further aspect of the invention provides for the use of a compound of formula (I) or a pharmaceutically acceptable salt or prodrug thereof in the manufacture of a medicament for the treatment of a disease or condition as above.

A further aspect of the invention provides a pharmaceutical composition comprising a compound of formula (I) or a pharmaceutically acceptable salt or prodrug thereof and a pharmaceutically acceptable carrier, diluent or excipient.

In another aspect, the invention provides a method of treating or preventing a disease or condition wherein MIF cytokine or biological activity is implicated comprising:

administering to a mammal a compound of formula (I) or a pharmaceutically acceptable salt or prodrug thereof and a second therapeutic agent.

In another aspect, the present invention provides a method of prophylaxis or treatment of a disease or condition for which treatment with a glucocorticoid is indicated, said method comprising:

administering to a mammal a glucocorticoid and a compound of formula (I) or a pharmaceutically acceptable salt or prodrug thereof.

In yet another aspect, the present invention provides a method of treating steroid-resistant diseases comprising:

administering to a mammal a glucocorticoid and a compound of formula (I) or a pharmaceutically acceptable salt or prodrug thereof.

In a further aspect, the present invention provides a method of enhancing the effect of a glucocorticoid in mammals comprising administering a compound of formula (I) or a pharmaceutically acceptable salt or prodrug thereof, simultaneously, separately or sequentially with said glucocorticoid.

In yet a further aspect, the present invention provides a pharmaceutical composition comprising a glucocorticoid and a compound of formula (I) or a pharmaceutically acceptable salt or prodrug thereof.

In a further aspect of the invention there is provided a use of a glucocorticoid in the manufacture of a medicament for administration with a compound of formula (I) or a pharmaceutically acceptable salt or prodrug thereof for the treatment or prophylaxis of a disease or condition for which treatment with a glucocorticoid is indicated.

In yet a further aspect of the invention there is provided a use of a compound of formula (I) or a pharmaceutically acceptable salt or prodrug thereof in the manufacture of a medicament for administration with a glucocorticoid for the treatment or prophylaxis of a disease or condition for which treatment of a glucocorticoid is indicated.

In yet a further aspect of the invention there is provided a use of a glucocorticoid and a compound of formula (I) or a pharmaceutically acceptable salt or prodrug thereof in the manufacture of a medicament for the treatment or prophylaxis of a disease or condition for which treatment with a glucocorticoid is indicated.

In preferred embodiments, the compound of formula (I) or a pharmaceutically acceptable salt or prodrug thereof are used to treat or prevent a disease or condition, particularly in a human subject.

In yet a further aspect of the invention, there is provided a compound of formula (III) or a pharmaceutically acceptable salt or prodrug thereof:

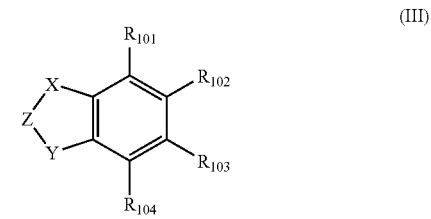

(III)

wherein

X is —O—, —NH—, —O— or —CH$_2$—;

Y is —NH—, —O— or —CH$_2$—;

Z is —C(O)—, —C(S)— or —S(O)—;

$R_{101}$ is selected from hydrogen, $C_{1-3}$alkyl, OH, SH, $NH_2$, $NHC_{1-3}$alkyl, F, Cl or Br;

$R_{102}$ is selected from $C_{1-20}$alkyl, $C_{2-20}$alkenyl, $CO_2H$, $CO_2R_{105}$, $-NH_2$, F, Cl, Br, $(CH_2)_nR_{106}$, $C(O)N(R_{107})_2$, $C(=N)NHC_{1-6}$alkyl, $SO_2C_{1-6}$alkyl, $C(O)[NHCH(R_{108})C(O)]_q$—$OR_{109}$, $C(O)$sugar, $C(O)NH(CH_2)_n$aryl, $NHC(O)(CH_2)_n$Sheterocyclyl, $C(O)SC_{1-6}$alkyl, $C(O)(CH_2)_nCO_2H$, $SO_2OC_{1-10}$alkyl and $SO_2NHC_{1-10}$alkyl;

$R_{103}$ is selected from hydrogen, F, Cl, Br, $C_{1-6}$alkyl, $-(CH_2)_nNH_2$, $-(CH_2)$, $-OH$, $-(CH_2)$, $-CF_3$, $-(CH_2)_6C(O)C_{1-3}$alkyl or $-(CH_2)_n$—SH;

$R_{104}$ is selected from hydrogen, methyl, ethyl, $CH_2C(R_{110})_3$, $C(R_{110})_3$, $-CH_2=CH_2$, fluoro, chloro or bromo;

$R_{105}$ is selected from hydrogen, $C_{1-20}$alkyl, $C_{2-20}$alkenyl or $(CH_2)_tOC_{1-3}$alkyl;

$R_{106}$ is selected from SH, $SC_{1-6}$alkyl, OH, $OC_{1-6}$alkyl, sugar, $CO_2H$, $NH_2$, heterocyclyl or aryl;

Each $R_{107}$ is independently selected from hydrogen, $C_{1-20}$alkyl, $C_{2-20}$alkenyl, $(CH_2)_t$aryl and $(CH_2)_t$heterocyclyl;

$R_{108}$ is the characterising group of an amino acid;

$R_{109}$ is hydrogen, $C_{1-3}$alkyl;

Each $R_{110}$ is independently selected from hydrogen and halo; and n is 0 or an integer from 1 to 3, q is an integer from 1 to 5, w is an integer from 1 to 6; t is an integer from 1 to 10; wherein each alkyl, alkenyl, alkynyl, aryl and heterocyclyl may be optionally substituted.

DETAILED DESCRIPTION OF THE INVENTION

Figure 1:
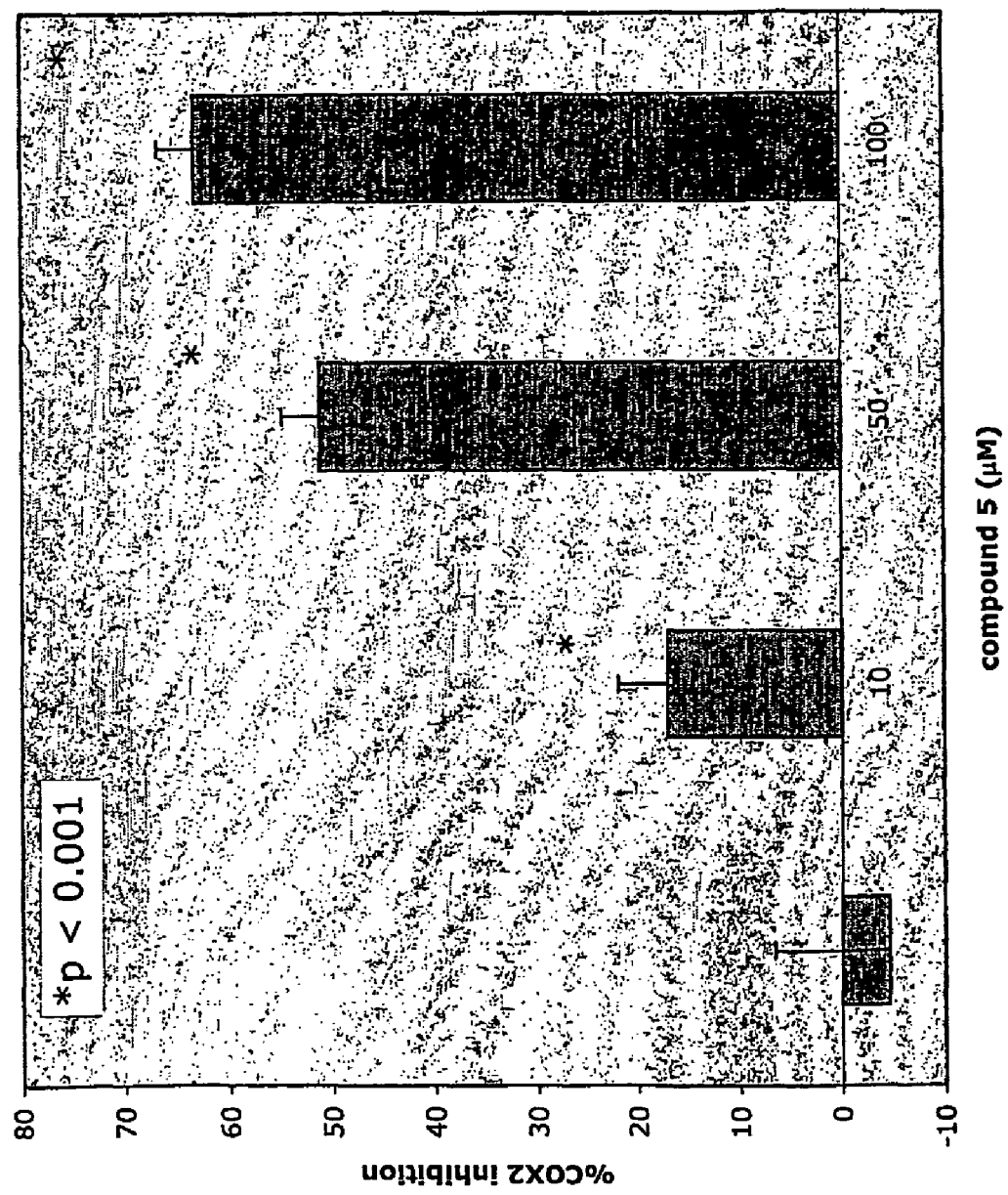
FIG. 1 graphically depicts dose response effect of benzimidazol-2-one-5-pentanoate (compound 5) on Interleukin-1 (IL-1)-induced cyclooxygenase II (COX-2) expression.

As used herein, the term "alkyl", either used alone or in compound terms such as NHCalkyl N(Calkyl)$_2$, etc., refers to monovalent straight, branched or, where appropriate, cyclic aliphatic radicals, having 1 to 3, 1 to 6, 1 to 10 or 1 to 20 carbon atoms as appropriate, e.g. methyl, ethyl, n-propyl, iso-propyl, cyclopropyl, n-butyl, sec-butyl, t-butyl and cyclobutyl, n-pentyl, 1-methylbutyl, 2-methylbutyl, 3-methylbutyl, cyclopentyl, n-hexyl, 1-2-3- or 4-methylpentyl, 1-2- or 3-ethylbutyl, 1 or 2-propylpropyl or cyclohexyl.

An alkyl group may be optionally substituted one or more times by halo (eg chloro, fluoro or bromo), CN, $NO_2$, $CO_2H$, $CO_2C_{1-6}$alkyl, $CONH_2$, $CONH(C_{1-6}$alkyl), $CONH(C_{1-6}$alkyl)$_2$, OH, hydroxyalkyl, alkoxy, methyl, ethyl, propyl, butyl, methoxy, ethoxy, butyloxy, acyl, carboxyalkyl, acetyl, trifluoromethyl, benzyloxy, phenoxy, $NH_2$, $NH(C_{1-6}$alkyl) or $NH(C_{1-6}$alkyl)$_2$. A preferred optional substituent is a polar substituent. Preferred optional substituents are hydroxy, $NH_2$ and $CO_2H$. Examples of alkoxy include methoxy, ethoxy, n-propoxy, iso-propoxy, cyclopropoxy, and butoxy (n-, sec-t- and cyclo) pentoxy and hexyloxy. The "alkyl" portion of an alkoxy group may be substituted as described above.

As used herein, the term "alkenyl" refers to straight, branched, or where appropriate, cyclic carbon containing radicals having one or more double bonds between carbon atoms. Examples of such radicals include vinyl, allyl, butenyl, or longer carbon chains such as those derived from palmitoleic, oleic, linoleic, linolenic or arachidonic acids. An alkenyl group may be optionally substituted one or more times by halo (eg chloro, fluoro or bromo), CN, $NO_2$, $CO_2H$, $CO_2C_{1-6}$alkyl, $CONH_2$, $CONH(C_{1-6}$alkyl), $CONH(C_{1-6}$alkyl)$_2$, OH, hydroxyalkyl, methyl, ethyl, butyl, propyl, alkoxy, acyl, carboxyalkyl, acetyl, trifluoromethyl, benzyloxy, phenoxy, $NH_2$, $NH(C_{1-6}$alkyl) or $NH(C_{1-6}$alkyl)$_2$. A preferred optional substituent is a polar substituent, such as $NH_2$, OH or $CO_2H$.

As used herein, the term "alkynyl" refers to straight or branched carbon containing radicals having one or more triple bonds between carbon atoms. Examples of such radicals include propargyl, butynyl and hexynyl. An alkynyl group may be optionally substituted one or more times by halo (eg chloro, fluoro or bromo), CN, $NO_2$, $CO_2H$, $COC_{1-6}$alkyl, $CO_2NH_2$, $CONH(C_{1-6}$alkyl), $CONH(C_{1-6}$alkyl)$_2$, OH, hydroxyalkyl, alkoxy, acyl, carboxyalkyl, acetyl, trifluoromethyl, benzyloxy, phenoxy, $NH_2$, $NH(C_{1-6}$alkyl) or $NH(C_1$alkyl)$_2$. A preferred optional substituent is a polar substituent, such as $NH_2$, OH and $CO_2H$.

Examples of suitable NH(alkyl) and N(alkyl)$_2$ include methylamino, ethylamino, isopropylamino, dimethylamino, n-propylamino, diethylamino and di-isopropylamino.

The term "halogen" (or "halo") refers to fluorine (fluoro), chlorine (chloro), bromine (bromo) or iodine (iodo).

The term "sugar" refers to a pyranosyl or furanosyl moiety such as those derived from glucose, galactose, mannose, allose, altrose, gulose, idose, talose, ribose, arabinose or xylose. Derivatives of such sugars include deoxy or aminopyranosyl or furanosyl sugar derivatives. Each sugar moiety is incorporated into the compound of formula (I) through a hydroxy group of the sugar moiety.

As used herein, "the characterising group of an amino acid" refers to the substituent at $C_2$ of a naturally occurring or non-naturally occurring amino acid and which defines the amino acid. The amino acid may be in the L- or D-configuration. For example, methyl is the characterising group of alanine, phenylmethyl is the characterising group of phenylalanine, hydroxymethyl is the characterising group of serine, hydroxyethyl is the characterising group of homoserine and n-propyl is the characterising group of norvaline.

An aryl group, as used herein, refers to $C_6$-$C_{10}$ aryl groups such as phenyl or naphthalene. Aryl groups may be optionally substituted one or more times by halo (eg, chloro, fluoro or bromo), CN, $NO_2$, $CO_2H$, $CO_2C_{1-6}$alkyl, $CONH_2$, CONH ($C_{1-6}$alkyl), $CONH(C_{1-6}$alkyl)$_2$, OH, hydroxyalkyl, alkoxy, acyl, carboxyalkyl, acetyl, trifluoromethyl, benzyloxy, phenoxy, $NH_2$, $NH(C_{1-6}$alkyl) or $NH(C_{1-6}$alkyl)$_2$. A preferred optional substituent is a polar substituent, particularly hydroxy, hydroxyalkyl or halo.

As used herein, the term "heterocyclyl" refers to a cyclic, aliphatic or aromatic radical containing at least one heteroatom independently selected from O, N or S. Examples of suitable heterocyclyl groups include furyl, pyridinyl, pyrimidinyl, pyrazolyl, piperidinyl, pyrrolyl, thiophenyl, oxazolyl, imidazolyl, thiazolyl, isoxazolyl, isothiazolyl, quinolyl, isoquinolyl, indolyl, benzofuranyl, benzothiophenyl, triazolyl, tetrazolyl, oxadiazolyl and purinyl. Heterocyclyl groups may be optionally substituted one or more times by halo (eg, chloro, fluoro or bromo), CN, $NO_2$, $CO_2H$, $CO_2C_{1-6}$alkyl, $CONH_2$, $CONH(C_{1-6}$alkyl), $CONH(C_{1-6}$alkyl)$_2$, OH, hydroxyalkyl, alkoxy, acyl, carboxyalkyl, acetyl, trifluoromethyl, benzyloxy, phenoxy, $NH_2$, $NH(C_{1-6}$alkyl) or $NH(C_{1-6}$alkyl)$_2$.

In a first aspect, the present invention provides a method of inhibiting cytokine or biological activity of MIF comprising contacting MIF with a cytokine or biological activity inhibiting effective amount of a compound of formula (I), or a pharmaceutically acceptable salt or prodrug thereof.

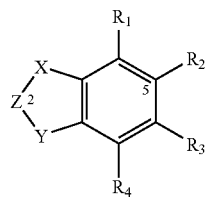

(I)

wherein

X is selected from —O—, —S—, —C($R_5$)($R_{5'}$)— or —N($R_6$)— and preferably comprises a hydrogen bond donor or acceptor;

Y is selected from —N($R_7$)—, —O—, —S— or —C($R_7$)$_2$—;

Z is selected from —C(O)—, —C(S)—, —C(=$NR_6$)—, —S(O)— or —S(O)$_2$—;

$R_1$ is selected from hydrogen, $C_{1-3}$alkyl, $(CR_5R_{5'})_nOR_7$, $(CR_5R_{5'})_nSR_7$, $(CR_5R_{5'})_nN(R_6)_2$ and $(CR_5R_{5'})_n$halo;

$R_2$ is selected from $C_1$-$C_{20}$alkyl, $C_2$-$C_{20}$alkenyl, $C_2$-$C_{20}$alkynyl, $(CR_{12}R_{12'})_mC(O)R_8$, $(CR_{12}R_{12'})_mC(S)R_8$, $(CR_{12}R_{12'})_mS(O)R_8$, $(CR_{12}R_{12'})_mS(O)_2R_8$, $(CR_{12}R_{12'})_mOR_9$, $(CR_{12}R_{12'})_mSR_9$, $(CR_{12}R_{12'})_mNR_{10}R_{11}$, $(CR_{12}R_{12'})_mC(=NR_{24})R_{22}$ and $(CR_{12}R_{12'})_mR_{13}$;

$R_3$ is selected from hydrogen, $C_1$-$C_6$alkyl, $(CR_{16}R_{16'})_pNR_{14}R_{15}$, $(CR_{16}R_{16'})_pOR_{17}$, $(CR_{16}R_{16'})_pSR_{17}$, $(CR_{16}R_{16'})_p$halo, $(CR_{16}R_{16'})_pNO_2$, $(CR_{16}R_{16'})_nC(O)R_{28}$, $(CR_{16}R_{16'})_nC(=NR_{24})R_{22}$, $(CR_{16}R_{16'})_nS(O)R_{17}$, $(CR_{16}R_{16'})_nS(O)_2R_{17}$, $(CR_{16}R_{16'})S(O)_3R_{17}$ and $(CR_{16}R_{16'})_pC(R_{18})_3$;

$R_4$ is selected from hydrogen, halogen, $C_1$-$C_3$alkyl, $C_{2-3}$alkenyl, $C_{2-3}$alkynyl and $(CR_{12}R_{12'})_nC(R_{18})_3$;

Each $R_5$ and $R_{5'}$ is independently selected from hydrogen, $C_1$-$C_3$alkyl, halo, $OR_7$, $SR_7$ and $N(R_6)_2$;

Each $R_6$ is independently selected from hydrogen, $C_1$-$C_3$alkyl and $OR_7$;

Each $R_7$ is independently selected from hydrogen and $C_1$-$C_3$alkyl;

$R_8$ is selected from hydrogen, $C_1$-$C_{20}$alkyl, $C_2$-$C_{20}$alkenyl, $C_2$-$C_{20}$alkynyl, $OR_{19}$, $SR_{19}$, $N(R_{20})_2$, [NH—CH($R_{21}$)—C(O)]$_q$—$OR_{29}$, [Sugar]$_q$ and $(CR_{12}R_{12'})_rR_{13}$;

$R_9$ is selected from hydrogen, $C_1$-$C_{20}$alkyl, $C_2$-$C_{20}$alkenyl, $C_2$-$C_{20}$alkynyl, $(CR_{12}R_{12'})_rR_{13}$, $C(O)R_{23}$, $CO_2R_{23}$, $C(S)R_{23}$, $C(S)OR_{23}$, $S(O)R_{23}$, $S(O)_2R_{23}$, [C(O)CH($R_{21}$)NH]$_q$—$R_{23}$ and [sugar]$_q$;

$R_{10}$ and $R_{11}$ are independently selected from hydrogen, $C_1$-$C_{20}$alkyl, $C_2$-$C_{20}$alkenyl, $C_2$-$C_{20}$alkynyl, $(CR_{12}R_{12'})_mR_{13}$, $C(O)R_{23}$, $C(S)R_{23}$, $S(O)R_{23}$, $S(O)_2R_{23}$, [C(O)CH($R_{21}$)NH]$_q$—$R_{23}$, -[sugar]$_q$ and $NHC(=NR_{25})$—$NH_2$;

Each $R_{12}$ and $R_{12'}$ is independently selected from hydrogen, $C_1$-$C_6$alkyl, $C_2$-$C_6$alkenyl, $C_2$-$C_6$alkynyl, $OR_{24}$, $SR_{24}$, halo, $N(R_{24})_2$, $CO_2R_{24}$, CN, $NO_2$, aryl or heterocyclyl;

$R_{13}$ is selected from $OR_{25}$, $SR_{25}$, halo, $N(R_{25})_2$, $C(O)R_{31}$, CN, $C(R_{18})_3$, aryl or heterocyclyl;

$R_{14}$ and $R_{15}$ are independently selected from hydrogen, $C_1$-$C_3$alkyl, $OR_{17}$, $(CR_{16}R_{16'})_pC(R_8)_3$;

Each $R_{16}$ and $R_{16'}$ is independently selected from hydrogen, $C_1$-$C_3$alkyl, halo, $OR_{17}$, $SR_{17}$ and $N(R_{17})_2$;

Each $R_{17}$ is independently selected from hydrogen and $C_1$-$C_3$alkyl;

Each $R_{18}$ is independently selected from hydrogen and halo;

$R_{19}$ and each $R_{20}$ are independently selected from hydrogen, $C_1$-$C_{20}$alkyl, $C_2$-$C_{20}$alkenyl, $C_2$-$C_{20}$alkynyl, $(CR_{26}R_{26'})_rR_{27}$;

$R_{21}$ is the characterising group of an amino acid;

$R_{22}$ is selected from $C_1$-$C_6$alkyl, $NH_2$, $NH(C_{1-6}$alkyl), $N(C_{1-6}$alkyl)$_2$, $OR_{29}$ or $SR_{29}$;

$R_{23}$ is selected from hydrogen, $C_1$-$C_{20}$alkyl, $C_2$-$C_{20}$alkenyl, $C_2$-$C_{20}$alkynyl, aryl $(CR_{26}R_{26'})_rR_{27}$;

Each $R_{24}$ is independently selected from hydrogen and $C_1$-$C_6$alkyl;

Each $R_{25}$ is independently selected from hydrogen, $C_1$-$C_6$alkyl, $C_{1-3}$alkoxy$C_{1-3}$alkyl, aryl and heterocyclyl;

Each $R_{26}$ and $R_{26'}$ is independently selected from hydrogen, $C_1$-$C_6$alkyl, $C_2$-$C_6$alkenyl, $C_2$-$C_6$alkynyl, $OR_{29}$, $SR_{29}$, halo, $N(R_{29})_2$, $CO_2R_{29}$, CN, $NO_2$, aryl and heterocyclyl;

$R_{27}$ is selected from hydrogen, $OR_{30}$, $SR_{30}$, halo, $N(R_{30})_2$, $CO_2R_{30}$, aryl and heterocyclyl;

$R_{28}$ is selected from hydrogen, $C_{1-6}$alkyl, $OR_{29}$, $SR_{29}$ or $N(R_{29})_2$;

Each $R_{29}$ is independently selected from hydrogen and $C_1$-$C_3$alkyl;

Each $R_{30}$ is independently selected from hydrogen, $C_1$-$C_3$alkyl, aryl and heterocyclyl;

$R_{31}$ is selected from $C_{1-3}$alkyl, OH, $C_{1-3}$alkoxy, aryl, aryloxy, heterocyclyl and heterocyclyloxy;

n is 0 or an integer from 1 to 3;

m is 0 or an integer from 1 to 20;

p is 0 or an integer from 1 to 6;

q is an integer from 1 to 5;

t is an integer from 1 to 10;

wherein alkyl, alkenyl, alkynyl, aryl and heterocyclyl may be optionally substituted.

In a preferred embodiment one or more of the following definitions apply:

X is —N(H)—, —N($C_{1-3}$alkyl)-, —N(OH)—, —N(O$C_{1-3}$alkyl)-, —O—, —S—, —$CH_2$—, —CH(OH)—, —CH($NH_2$)—, —CH($C_{1-3}$alkyl)-, —CH(halo)-, —CH(SH)—, —CH(O$C_{1-3}$alkyl) or —CH(S$C_{1-3}$alkyl)-; more preferably, —N(H)—, —$CH_2$—, —S— or —O—.

Y is —NH—, —N($C_{1-3}$alkyl)-, —O—, —S— or —$CH_2$—; more preferably —O—, —NH— or —$CH_2$—;

Z is —C(O)—, —C(S)—, —S(O)—, —C(=NH)—, —C(=N$C_{1-3}$alkyl)-, —C(=NOH)— or —C(=NO$C_{1-3}$alkyl), more preferably —C(O)—, —C(S)— or —S(O)—;

$R_1$ is hydrogen, $CH_3$, OH, SH, $NH_2$, $NHCH_3$, F, Cl or Br, more preferably hydrogen, $CH_3$, Br or $NHCH_3$;

$R_2$ is selected from $C_{1-20}$alkyl, $C_{1-20}$alkenyl, $(CR_{12}R_{12'})_m$heterocyclyl, $(CR_{12}R_{12'})_m$aryl, $(CR_{12}R_{12'})_n$halo, $(CR_{12}R_{12'})_m$OH, $(CR_{12}R_{12'})_m$O$C_{1-20}$alkyl, $(CR_{12}R_{12'})_m$O$C_{2-20}$alkenyl, $(CR_{12}R_{12'})_m$OC(O)$C_{1-20}$alkyl, $(CR_{12}R_{12'})_m$OC(O)$C_{2-20}$alkenyl, $(CR_{12}R_{12'})_m$OC(O)aryl, $(CR_{12}R_{12'})_m$O[C(O)CH($R_{21}$)NH]$_r$—H, $(CR_{12}R_{12'})_m$O[sugar]$_r$, $(CR_{12}R_{12'})_m$$NH_2$ $(CR_{12}R_{12'})_m$NH$C_{1-20}$alkyl, $(CR_{12}R_{12'})_n$N($C_{1-20}$alkyl)$_2$, $(CR_{12}R_{12'})_m$N$C_{2-20}$alkenyl, $(CR_{12}R_{12'})_m$N($C_{2-20}$alkenyl)$_2$, $(CR_{12}R_{12'})_n$N($C_{1-20}$alkyl)($C_{2-20}$alkenyl), $(CR_{12}R_{12'})_m$NHC(O)$C_{1-20}$alkyl, $(CR_{12}R_{12'})_m$NHC(O)$C_{2-20}$alkenyl, $(CR_{12}R_{12'})_n$NHC(O)aryl, $(CR_{12}R_{12'})_m$NH[C(O)CH($R_{21}$)NH]$_r$—H, $(CR_{12}R_{12'})_m$NH-[sugar]$_r$, $(CR_{12}R_{12'})_m$SO$_3$H, $(CR_{12}R_{12'})_m$SO$_3$$C_{1-20}$alkyl, $(CR_{12}R_{12'})_m$SO$_3$$C_{2-20}$alkenyl, $(CR_{12}R_{12'})_m$C(O)$C_{1-20}$alkyl, $(CR_{12}R_{12'})_m$C(O)$C_{2-20}$alkenyl, $(CR_{12}R_{12'})_m$CO$_2$H, $(CR_{12}R_{12'})_m$CO$_2$$C_{1-20}$alkyl, $(CR_{12}R_{12'})_m$CO$_2$$C_{2-20}$alkenyl, $(CR_{12}R_{12'})_m$C(O)NH$C_{1-20}$alkyl, $(CR_{12}R_{12'})_m$C(O)N($C_{1-20}$alkyl)$_2$, $(CR_{12}R_{12'})_m$C(O)NH$C_{2-20}$alkenyl, $(CR_{12}R_{12'})_m$C(O)N($C_{2-20}$alkenyl)$_2$, $(CR_{12}R_{12'})_m$C(O)N($C_{1-20}$alkyl)($C_{2-20}$alkenyl), $(CR_{12}R_{12'})_m$C(O)[NHCH($R_{21}$)C(O)]$_r$—OH, $(CR_{12}R_{12'})_m$C(O)[NHCH($R_{21}$)C(O)]$_r$—OCH$_3$ $(CR_{12}R_{12'})_m$C(O)[sugar]$_r$, $(CR_{12}R_{12'})_m$S$C_{1-6}$alkyl, C(=N)NH$C_{1-4}$alkyl; wherein each $R_{12}$ and $R_{12'}$ is independently selected from hydrogen, $C_{1-6}$alkyl, $C_{2-6}$alkenyl, $C_{2-6}$alkynyl, halogen, OH, hydroxy$C_{1-6}$alkyl, O$C_{1-6}$alkyl, CO$_2$H, CO$_2$$C_{1-3}$allyl, $NH_2$, NH$C_{1-3}$alkyl, N($C_{1-3}$alkyl)$_2$, CN, $NO_2$, aryl or heterocyclyl; $R_2$, is the characterising group of an amino acid, m is 0 or an integer from 1 to 20 and r is an integer from 1 to 5; more preferably $R_2$ is selected from $(CH_2)_{1-6}$CO$_2$H, $C_{1-20}$alkyl, $C_{1-20}$alkenyl, CO$_2$$C_{1-6}$alkyl, $(CH_2)_{0-6}$$NH_2$, $(CH_2)_{1-6}$heterocyclyl, $(CH_2)_{1-6}$aryl wherein aryl is optionally substituted with one or more OH or hydroxy$C_{1-3}$alkyl groups, CO$_2$$C_{1-6}$alkyleneO$C_{1-6}$alkyl wherein the $C_{1-6}$alkyl is optionally substituted with OH, C(O)[NHCH($R_{21}$)C(O)]$_r$—OH, C(O)[NHCH($R_{21}$)C(O)]$_r$—OCH$_3$, SO$_3$$C_{1-10}$alkyl, SO$_2$NH$C_{1-10}$alkyl, C(=N)NH$C_{1-6}$alkyl, $(CH_2)_{1-3}$Osugar, $(CH_2)_{1-3}$S$C_{1-6}$alkyl, C(O)$C_{1-6}$alkylCO$_2$H, C)O)S$C_{1-6}$alkyl, NHC(O)$C_{1-3}$ alkylSheterocyclyl, C(O)NH$(CH_2)_{1-3}$aryl wherein aryl is optionally substituted with one or more OH groups;

$R_3$ is hydrogen, halogen $C_1$-$C_6$alkyl, —$(CH_2)_n$$NH_2$, —$(CH_2)_n$ $NO_2$, —$(CH_2)$, —OH, $(CH_2)_n$C(O)$C_{1-3}$alkyl, —$(CH_2)_n$—CF$_3$ or —$(CH_2)$, —SH wherein n is 0 or an integer from 1 to 3; more preferably $R_3$ is hydrogen, $NH_2$, $(CH_2)_n$ C(O)$C_{1-3}$ alkyl, $NO_2$, Br, OH, or CH$_3$;

$R_4$ is hydrogen, methyl, ethyl, —$CH_2$=$CH_2$, $CH_2$CF$_3$, fluoro, chloro or bromo, more preferably hydrogen or bromo, especially hydrogen.

At least one of $R_5$ and $R_{5'}$ is hydrogen in each $(CR_5R_{5'})$ and wherein the number of $(CR_5R_{5'})$ as designated by n is greater than 2, preferably less than 2 of $R_5$ and $R_{5'}$ are other than hydrogen, more preferably, $(CR_5R_{5'})_n$ represents an unsubstituted alkylene chain with n designating the number of methylene groups in the chain.

At least one of $R_{12}$ and $R_{12'}$ is hydrogen in each $(CR_{12}R_{12'})$ and wherein the number of $(CR_{12}R_{12'})$ as designated by m is greater than 5, preferably less than 5 of $R_{12}$ and $R_{12'}$ are other than hydrogen, more preferably, $(CR_{12}R_{12'})_m$ represents an unsubstituted alkylene chain with m designating the number of methylene groups in the chain.

At least one of $R_{16}$ and $R_{16'}$ is hydrogen in each $(CR_{16}R_{16'})$ and wherein the number of $(CR_{16}R_{16'})$ as designated by n is greater than 2, preferably less than 2 of $R_{16}$ and $R_{16'}$ are other than hydrogen, and wherein the number of $(CR_{16}R_{16'})$ as designated by p is greater than 4, preferably less than 4 of $R_{16}$ and $R_{16'}$ are other than hydrogen, more preferably, $(CR_{16}R_{16'})_n$ and $(CR_{16}R_{16'})_p$ represent an unsubstituted alkylene chain with n or p designating the number of methylene groups in the chain.

At least one of $R_{26}$ and $R_{26'}$ is hydrogen in each $(CR_{26}R_{26'})$ and wherein the number of $(CR_{26}R_{26'})$ as designated by t is greater than 5, preferably less than 5 of $R_{26}$ and $R_{26'}$ are other than hydrogen, more preferably, $(CR_{26}R_{26'})_t$ represents an unsubstituted alkylene chain with t designating the number of methylene groups in the chain.

Alkyl, alkenyl, alkynyl, aryl and heterocyclyl, are optionally substituted with one or more substituents selected from the group halogen, hydroxy, hydroxyalkyl, alkoxy, $C_{1-6}$alkyl, carboxylic acid, carboxylic ester, amino, alkyl substituted amino, —CN and —$NO_2$, particularly halogen, hydroxy, hydroxyalkyl and carboxylic acid.

In certain preferred forms of the invention, the compounds of formula (I) include:

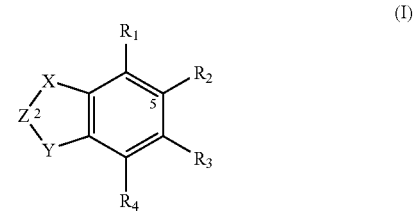

wherein

X is selected from —O—, —S—, —C(R$_5$)(R$_{5'}$)— or —N(R$_6$)— and preferably comprises a hydrogen bond donor or acceptor;

Y is selected from —N(R$_7$)— or —C(R$_7$)$_2$—;

Z is selected from —C(O)—, —C(S)—, —C(=NR$_6$)—, —S(O)— or —S(O)$_2$—;

R$_1$ is selected from hydrogen, C$_{1-3}$alkyl, (CR$_5$R$_{5'}$)$_n$OR$_7$, (CR$_5$R$_{5'}$)—SR$_7$, (CR$_5$R$_{5'}$)$_n$N(R$_6$)$_2$ and (CR$_5$R$_{5'}$)$_n$halo;

R$_2$ is selected from C$_1$-C$_{20}$alkyl, C$_2$-C$_{20}$alkenyl, C$_2$-C$_{20}$alkynyl, (CR$_{12}$R$_{12'}$)$_m$C(O)R$_8$, (CR$_{12}$R$_{12'}$)$_m$C(S)R$_8$, (CR$_{12}$R$_{12'}$)$_m$S(O)R$_8$, (CR$_{12}$R$_{12'}$)$_m$S(O)$_2$R$_8$, (CR$_{12}$R$_{12'}$)$_m$OR$_9$, (CR$_{12}$R$_{12'}$)$_m$SR$_9$, (CR$_{12}$R$_{12'}$)$_m$NR$_{10}$R$_{11}$, (CR$_{12}$R$_{12'}$)$_m$C(=NR$_{24}$)R$_{22}$ and (CR$_{12}$R$_{12'}$)$_m$R$_{13}$;

R$_3$ is selected from hydrogen, C$_1$-C$_6$alkyl, (CR$_{16}$R$_{16'}$)$_p$NR$_{14}$R$_{15}$, (CR$_{16}$R$_{16'}$)$_p$OR$_{17}$, (CR$_{16}$R$_{16'}$)$_p$SR$_{17}$, (CR$_{16}$P$_{16'}$)$_p$halo, (CR$_{16}$R$_{16'}$)$_p$NO$_2$, (CR$_{16}$R$_{16'}$)$_n$C(O)R$_{28}$, (CR$_{16}$R$_{16'}$)$_n$C(=NR$_{24}$)R$_{22}$, (CR$_{16}$R$_{16'}$)$_n$S(O)R$_{17}$, (CR$_{16}$R$_{16'}$)$_n$S(O)$_2$R$_{17}$, (CR$_{16}$R$_{16'}$)$_n$S(O)$_3$R$_{17}$ and (CR$_{16}$R$_{16'}$)$_p$C(R$_{18}$)$_3$;

R$_4$ is selected from hydrogen, halogen, C$_1$-C$_3$alkyl, C$_{2-3}$alkenyl, C$_{2-3}$allyl and (CR$_{12}$R$_{12'}$)$_n$C(R$_{18}$)$_3$;

Each R$_5$ and R$_{5'}$ is independently selected from hydrogen, C$_1$-C$_3$alkyl, halo, OR$_7$, SR$_7$ and N(R$_6$)$_2$;

Each R$_6$ is independently selected from hydrogen, C$_1$-C$_3$alkyl and OR$_7$;

Each R$_7$ is independently selected from hydrogen and C$_1$-C$_3$alkyl;

R$_8$ is selected from hydrogen, C$_1$-C$_{20}$alkyl, C$_2$-C$_{20}$alkenyl, C$_2$-C$_{20}$alkynyl, OR$_{19}$, SR$_{19}$, N(R$_{20}$)$_2$, [NH—CH(R$_{21}$)—C(O)]$_q$—OR$_{29}$, [sugar]$_q$ and (CR$_{12}$R$_{12'}$)$_r$R$_{13}$;

R$_9$ is selected from hydrogen, C$_1$-C$_{20}$alkyl, C$_2$-C$_{20}$alkenyl, C$_2$-C$_{20}$alkynyl, (CR$_{12}$R$_{12'}$)$_r$R$_{13}$, C(O)R$_{23}$, CO$_2$R$_{23}$, C(S)R$_{23}$, C(S)OR$_{23}$, S(O)R$_{23}$, S(O)$_2$R$_{23}$; [C(O)CH(R$_{21}$)NH]$_q$—R$_{23}$ and [sugar]$_q$;

R$_{10}$ and R$_{11}$ are independently selected from hydrogen, C$_1$-C$_{20}$alkyl, C$_2$-C$_{20}$alkenyl, C$_2$-C$_{20}$alkynyl, (CR$_{12}$R$_{12'}$)$_m$R$_{13}$, C(O)R$_{23}$, C(S)R$_{23}$, S(O)R$_{23}$, S(O)$_2$R$_{23}$, [C(O)CH(R$_{2'}$)NH]$_q$—R$_{23}$, -[sugar]$_q$ and NHC(=NR$_{25}$)—NH$_2$;

Each R$_{12}$ and R$_{12'}$ is independently selected from hydrogen, C$_1$-C$_6$alkyl, C$_2$-C$_6$alkenyl, C$_2$-C$_6$alkynyl, OR$_{24}$, SR$_{24}$, halo, N(R$_{24}$)$_2$, CO$_2$R$_{24}$, CN, NO$_2$, aryl or heterocyclyl;

R$_{13}$ is selected from OR$_{25}$, SR$_{25}$, halo, N(R$_{25}$)$_2$, C(O)R$_{31}$, CN, C(R$_{18}$)$_3$, aryl or heterocyclyl;

R$_{14}$ and R$_{15}$ are independently selected from hydrogen, C$_1$-C$_3$alkyl, OR$_{17}$, (CR$_{16}$R$_{16'}$)$_p$C(R$_{18}$)$_3$;

Each R$_{16}$ and R$_{16'}$ is independently selected from hydrogen, C$_1$-C$_3$alkyl, halo, OR$_{17}$, SR$_{17}$ and N(R$_{17}$)$_2$;

Each R$_{17}$ is independently selected from hydrogen and C$_1$-C$_3$alkyl;

Each R$_{18}$ is independently selected from hydrogen and halo;

R$_{19}$ and each R$_{20}$ are independently selected from hydrogen, C$_1$-C$_{20}$alkyl, C$_2$-C$_{20}$alkenyl, C$_2$-C$_{20}$alkynyl, (CR$_{26}$R$_{26'}$)$_t$R$_{27}$;

R$_{21}$ is the characterising group of an amino acid;

R$_{22}$ is selected from C$_1$-C$_6$alkyl, NH$_2$, NH(C$_1$alkyl), N(C$_1$alkyl)$_2$, OR$_{29}$ or SR$_{29}$;

R$_{23}$ is selected from hydrogen, C$_1$-C$_{20}$alkyl, C$_2$-C$_{20}$alkenyl, C$_2$-C$_{20}$alkynyl, aryl (CR$_{26}$R$_{26'}$)$_t$R$_{27}$;

Each R$_{24}$ is independently selected from hydrogen and C$_1$-C$_6$alkyl;

Each R$_{25}$ is independently selected from hydrogen, C$_1$-C$_6$alkyl, C$_{1-3}$alkoxyC$_{1-3}$alkyl, aryl and heterocyclyl;

Each R$_{26}$ and R$_{26'}$ is independently selected from hydrogen, C$_1$-C$_6$alkyl, C$_2$-C$_6$alkenyl, C$_2$-C$_6$alkynyl, OR$_{29}$, SR$_{29}$, halo, N(R$_{29}$)$_2$, CO$_2$R$_{29}$, CN, NO$_2$, aryl and heterocyclyl;

R$_{27}$ is selected from hydrogen, OR$_{30}$, SR$_{30}$, halo, N(R$_{30}$)$_2$, CO$_2$R$_{30}$, aryl and heterocyclyl;

R$_{28}$ is selected from hydrogen, C$_{1-6}$alkyl, OR$_{29}$, SR$_{29}$ or N(R$_{29}$)$_2$;

Each R$_{29}$ is independently selected from hydrogen and C$_1$-C$_3$alkyl;

Each R$_{30}$ is independently selected from hydrogen, C$_1$-C$_3$alkyl, aryl and heterocyclyl;

R$_{31}$ is selected from C$_{1-3}$alkyl, OH, C$_{1-3}$alkoxy, aryl, aryloxy, heterocyclyl and heterocyclyloxy;

n is 0 or an integer from 1 to 3;

m is 0 or an integer from 1 to 20;

p is 0 or an integer from 1 to 6;

q is an integer from 1 to 5;

t is an integer from 1 to 10;

wherein alkyl, alkenyl, alkynyl, aryl and heterocyclyl may be optionally substituted.

In certain preferred forms of the invention, the compounds of formula (I) include:

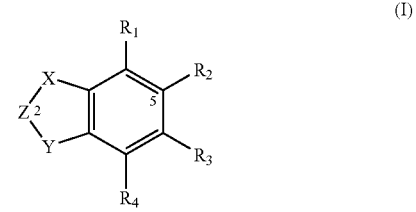

(I)

wherein

X is —O—, —S—, —C(R$_5$)$_2$— or —N(R$_6$)—;

Y is —N(R$_7$)—, —O—, —S— or —C(R$_7$)$_2$—;

Z is —C(O)—, —C(S)—, —S(O)— or —C(=NR$_6$);

R$_1$ is hydrogen, CH$_3$, OH, SH, NH$_2$, NHCH$_3$, F, Cl or Br;

R$_2$ is C$_1$-C$_{20}$alkyl, C$_2$-C$_{20}$alkenyl, C$_2$-C$_{20}$alkynyl, (CR$_{12}$R$_{12'}$)$_m$ C(O)R$_8$, (CR$_{12}$R$_{12'}$)$_m$C(S)R$_8$, —(CR$_{12}$R$_{12'}$)$_m$S(O)R$_8$, —(CR$_{12}$R$_{12'}$)$_m$S(O)$_2$R$_8$, —(CR$_{12}$R$_{12'}$)$_m$OR$_9$, (CR$_{12}$R$_{12'}$)$_m$SR$_9$, —(CR$_{12}$R$_{12'}$)$_m$R$_{10}$R$_{11}$, (CR$_{12}$R$_{12'}$)$_m$C(=NR$_{24}$)R$_{22}$ or (CR$_{12}$R$_{12'}$)$_m$R$_{13}$ where m, R$_7$, R$_8$, R$_9$, R$_{10}$, R$_{11}$, R$_{12}$, R$_{12'}$, R$_{13}$, R$_{22}$ and R$_{24}$ are defined above;

R$_3$ is hydrogen, halogen, C$_{1-6}$alkyl, —(CH$_2$)$_n$NH$_2$, —(CH$_2$)$_n$NO$_2$, —(CH$_2$)$_n$-OH, —(CH$_2$)$_n$C(O)C$_{1-3}$alkyl, —(CH$_2$)$_n$CF$_3$ or —(CH$_2$)$_n$SH where n is defined above;

R$_4$ is hydrogen, halogen, methyl, ethyl, CH$_2$CF$_3$ or —CH$_2$=CH$_2$.

Preferred compounds of formula (I) comprise

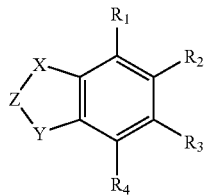

wherein

X is —N($R_6$)—;

Y is —N($R_7$)— or —C($R_7$)$_2$—;

Z is —C(O)—, —C(S)—, —S(O)— or —C(=NH);

$R_1$ is hydrogen, $CH_3$, $NH_2$, $NHCH_3$, F, Cl or Br;

$R_2$ is as defined for $R_2$ above;

$R_3$ is hydrogen, halogen, $C_{1-3}$alkyl, $(CH_2)_nNH_2$, $(CH_2)_nNO_2$, $(CH_2)_nOH$, $(CH_2)_nC(O)CH_3$ or $(CH_2)_nCF_3$ where n is defined above;

$R_4$ is hydrogen, halogen, methyl, ethyl, $CH_2CF_3$ or —$CH_2$=$CH_2$.

Preferred compounds of formula (I) are benzimidazole compounds having the formula (II)

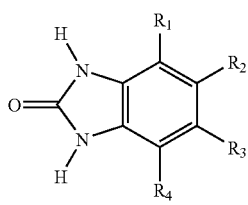

wherein $R_1$ is hydrogen, $CH_3$, $NHCH_3$, F, Cl or Br;

$R_2$ is as defined for $R_2$ above;

$R_3$ is hydrogen, halogen, $C_1$-$C_3$alkyl, $(CH_2)_nNH_2$, $(CH_2)_nNO_2$, $(CH_2)_nOH$, $CH_2C(O)CH_3$, $(CH_2)_nCF_3$ where n is defined above.

$R_4$ is hydrogen, halogen, methyl, ethyl, $CH_2CF_3$ or —$CH_2$=$CH_2$.

Other preferred compounds of formula (I) are compounds having formula (III):

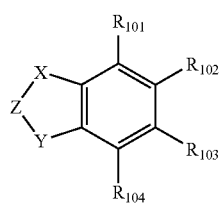

wherein

X is —O—, —NH— or —$CH_2$—;

Y is —NH—, —O— or —$CH_2$—;

Z is —C(O)—, —C(S)— or —S(O)—;

$R_{101}$ is selected from hydrogen, $C_{1-3}$alkyl, OH, SH, $NH_2$, $NHC_{1-3}$alkyl, F, Cl or Br;

$R_{102}$ is selected from $C_{1-20}$alkyl, $C_{2-20}$alkenyl, $CO_2H$, $CO_2R_{105}$, —$NH_2$, F, Cl, Br, $(CH_2)_wR_{106}$, $C(O)N(R_{107})_2$, $C(=N)NHC_{1-6}$alkyl, $SO_2C_{1-6}$alkyl, $C(O)[NHCH(R_{108})C(O)]_q$—$OR_{109}$, C(O)sugar, $CONH(CH_2)_t$aryl, $NHC(O)(CH_2)_n$Sheterocyclyl, $C(O)SC_{1-6}$alkyl, $C(O)(CH_2)_nCO_2H$, $SO_2OC_{1-10}$alkyl, and $SO_2NHC_{1-10}$alkyl;

$R_{103}$ is selected from hydrogen, f, Cl, Br, $C_{1-6}$alkyl, —$(CH_2)_n$$NH_2$, —$(CH_2)_nNO_2$, —$(CH_2)_n$—OH, —$(CH_2)_n$—$CF_3$, —$(CH_2)_nC(O)C_{1-3}$alkyl or —$(CH_2)_n$—SH;

$R_{104}$ is selected from hydrogen, methyl, ethyl, $CH_2C(R_{110})_3$, $C(R_{110})_3$, —$CH_2$=$CH_2$, fluoro, chloro or bromo;

$R_{105}$ is selected from hydrogen, $C_{1-20}$alkyl, $C_{2-20}$alkenyl or $(CH_2)_tOC_{1-3}$alkyl;

$R_{106}$ is selected from SH, $SC_{1-6}$allyl, OH, $OC_{1-6}$alkyl, sugar, $CO_2H$, $NH_2$, heterocyclyl or aryl;

Each $R_{107}$ is independently selected from hydrogen, $C_{1-20}$alkyl, $C_{2-20}$alkenyl, $(CH_2)_t$aryl and $(CH_2)_t$heterocyclyl;

$R_{108}$ is the characterising group of an amino acid;

$R_{109}$ is hydrogen, $C_{1-3}$alkyl;

Each $R_{110}$ is independently selected from hydrogen and halo; and n is 0 or an integer from 1 to 3, q is an integer from 1 to 5, w is an integer from 1 to 6; t is an integer from 1 to 10; wherein each alkyl, alkenyl, alkynyl, aryl and heterocyclyl may be optionally substituted.

Preferred compounds of formula (I) are benzimidazole compounds having formula (IV):

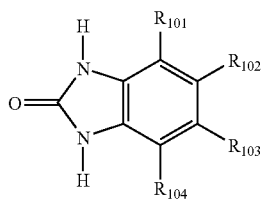

wherein $R_{101}$ is selected from hydrogen, $CH_3$, OH, SH, $NH_2$, $NHCH_3$, F, Cl or Br;

$R_{102}$ is selected from $C_{1-20}$alkyl, $C_{2-20}$alkenyl, $CO_2H$, $CO_2R_{105}$, —$NH_2$, F, Cl, Br, $(CH_2)_wR_{106}$, $C(O)N(R_{107})_2$, $C(=N)NHC_{1-6}$alkyl, $SO_2C_{1-6}$alkyl, $C(O)[NHCH(R_{108})C(O)]_q$—$OR_{109}$, C(O)sugar, $CONH(CH_2)_n$aryl, $NHC(O)(CH_2)_n$Sheterocyclyl, $C(O)SC_{1-6}$alkyl, $C(O)(CH_2)_nCO_2H$, $SO_2OC_{1-10}$alkyl, and $SO_2NHC_{1-10}$alkyl;

$R_{103}$ is selected from hydrogen, F, Cl, Br, $C_{1-6}$alkyl, $(CH_2)_nNH_2$, —$(CH_2)_nNO_2$, —$(CH_2)_n$—OH, —$(CH_2)_n$—$CF_3$, $CH_2C(O)CH_3$ or —$(CH_2)_n$—SH;

$R_{104}$ is selected from hydrogen, methyl, ethyl, $CH_2CF_3$, —$CH_2$=$CH_2$ fluoro, chloro or bromo;

$R_{105}$ is selected from hydrogen, $C_{1-10}$alkyl, $C_{2-10}$alkenyl, $(CH_2)_tOC_{1-3}$alkyl;

$R_{106}$ is selected from SH, $SC_{1-6}$alkyl, OH, $OC_{1-6}$alkyl, sugar, $CO_2H$, $NH_2$, heterocyclyl or aryl;

Each $R_{107}$ is independently selected from hydrogen, $C_{1-10}$alkyl, $C_{2-10}$alkenyl, $(CH_2)_t$aryl and $(CH_2)_t$heterocyclyl;

$R_{108}$ is the characterising group of an amino acid;

$R_{109}$ is hydrogen, $C_{1-3}$alkyl;

Each $R_{110}$ is independently selected from hydrogen and halo; and n is 0 or an integer from 1 to 3, q is an integer from 1 to 5, w is an integer from 1 to 6, t is an integer from 1 to 10; wherein each alkyl, alkenyl, alkynyl, aryl and heterocyclyl may be optionally substituted.

Examples of suitable compound include

-continued

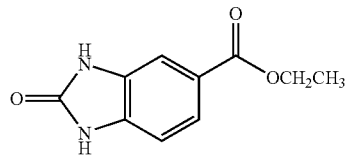
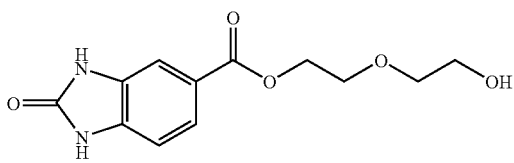
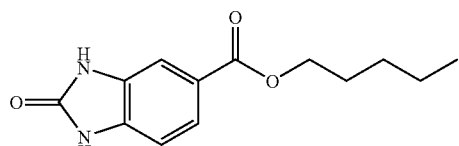
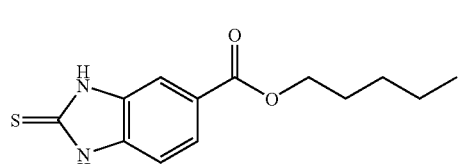
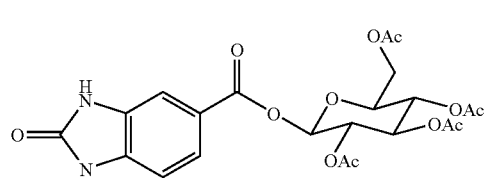
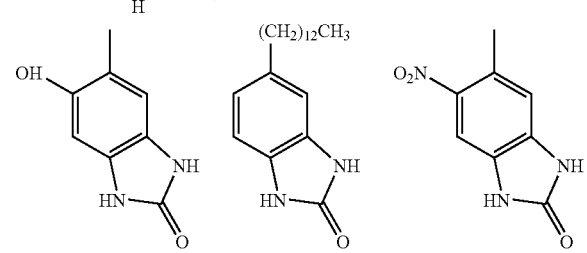
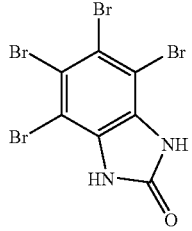
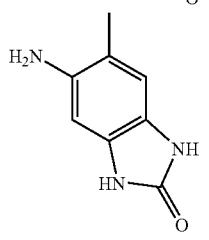
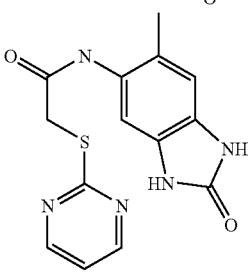

19

-continued

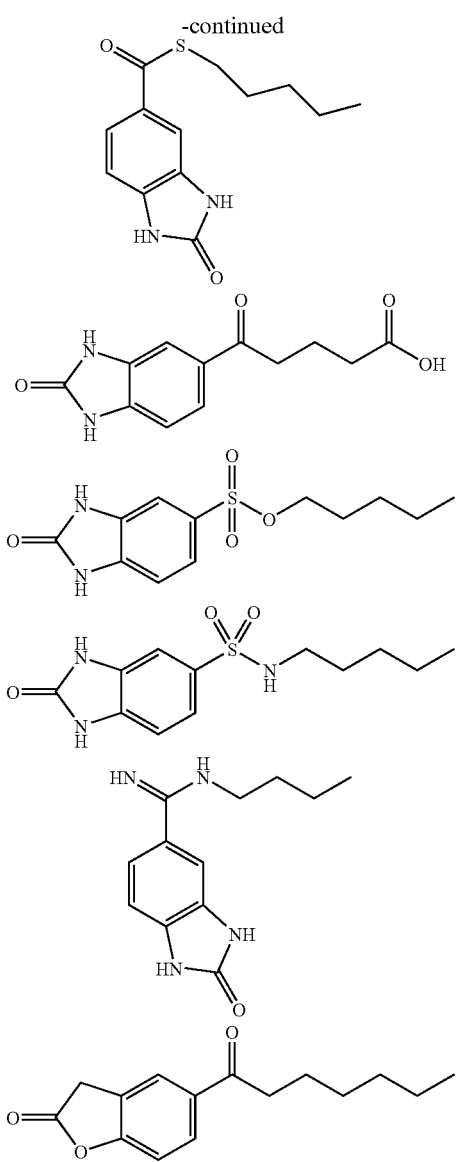

Compounds of formula (I) may be prepared using the methods depicted or described herein or known in the art. It will be understood that minor modifications to methods described herein or known in the art may be required to synthesize particular compounds of formula (I). General synthetic procedures applicable to the synthesis of compounds may be found in standard references such as *Comprehensive Organic Transformations*, R. C. Larock, 1989, VCH Publishers and *Advanced Organic Chemistry*, J. March, 4th Edition (1992), Wiley InterScience, and references therein. It will also be recognised that certain reactive groups may require protection and deprotection during the synthetic process. Suitable protecting and deprotecting methods for reactive functional groups are known in the art for example in *Protective Groups in Organic Synthesis*, T. W. Green & P. Wutz, John Wiley & Son, $3^{rd}$ Edition, 1999.

Thus, for certain embodiments of the invention, compounds of formula (I), where X and Y are N and Z is —C(O)—, —S(O)— or —(C=NR$_6$)— may be prepared in accordance with the exemplified general methods depicted in scheme 1 (3). Suitable starting materials can be obtained commercially or prepared using methods known in the art.

Scheme 1

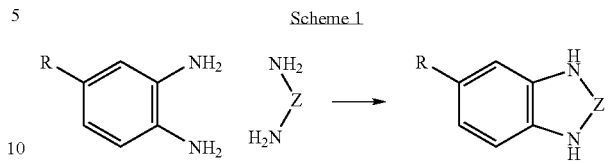

When R is —CO$_2$H or —C(S)OH, the compounds may be further derivatised to provide ketones, thioketones, esters, thioesters, amides and thioamides by standard alkylating, esterifying or amide forming methodology. When R is hydroxy, thiol or amino, these groups may be further derivatised to provide esters, thioesters, amides, ethers, thioethers and N-alkyl groups using standard acylating or alkylating methodology. Conversion of an amide to C=NH(NH$_2$) can be achieved by aminolysis eg NH$_3$/dry methanol.

When R is CO$_2$H, a methylene group can be inserted between the benzene nucleus and the carboxylic acid group by Arndt-Eistert synthesis, eg by conversion of the carboxylic acid to an acyl halide and conversion to the diazoketone. Rearrangement of the diazoketone (eg with silver oxide and water) affords access to the CH$_2$—CO$_2$H group. Repeating these steps allows for further incorporation of methylene groups. The CO$_2$H group can be converted as above.

In other embodiments, compounds of formula (I), where R$_2$ is a substituted methyl group, can be prepared by conversion of the methyl substituent (R$_2$) into a halomethyl substituent (eg by treatment with a N-halosuccinimide such as NBS) followed by nucleophilic substitution by an appropriate nucleophile and/or insertion of additional methylene groups by, for example, Wittig reaction (see Scheme 2 where R* can be, for example, (CH$_2$)$_m$OH, (CH$_2$)$_m$SH, (CH$_2$)$_m$NH$_2$ (CH$_2$)$_m$C(O)C$_{1-20}$alkyl, (CH$_2$)$_m$OC(O)C$_{1-10}$alkyl, (CH$_2$)$_m$OC$_{1-20}$alkyl, (CH$_2$)$_m$Ophenyl, (CH$_2$)$_m$Obenzyl, (CH$_2$)$_m$NHC$_{1-20}$alkyl, (CH$_2$)$_n$N(C$_{1-20}$alkyl)$_2$, (CH$_2$)$_n$NHphenyl, (CH$_2$)$_n$Nbenzyl, (CH$_2$)$_n$SC$_{1-20}$alkyl, (CH$_2$)$_m$SC(O)C$_{1-10}$alkyl, (CH$_2$)$_m$Sphenyl, (CH$_2$)$_m$Sbenzyl, (CH$_2$)$_m$NHsugar, (CH$_2$)$_m$ Ssugar, (CH$_2$)$_m$Osugar, (CH$_2$)$_m$NHC(O)C$_{1-10}$alkyl, (CH$_2$)$_m$ NHC(O) phenyl, (CH$_2$)$_m$NC(O)benzyl, (CH$_2$)$_m$NHCO$_2$C$_{1-6}$ alkyl, (CH$_2$)$_m$NHCO$_2$phenyl, or (CH$_2$)$_n$NHCO$_2$benzyl, where m is 0 or 1 to 20).

Scheme 2

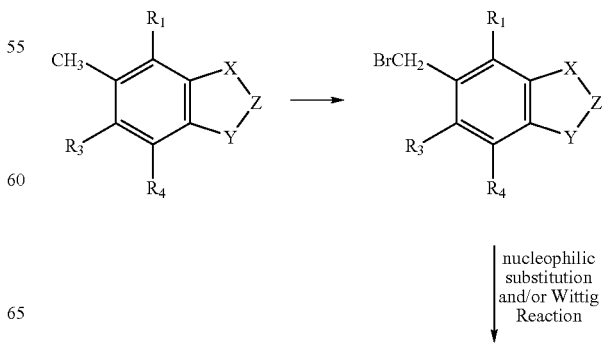

nucleophilic substitution and/or Wittig Reaction

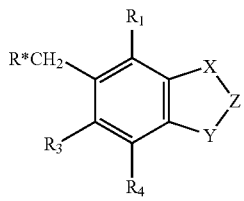

In other embodiments, compounds where $R_2$ is $CH_2$halo can be prepared by reaction of a suitable carboxylic acid derivative with a reducing agent such as $LiAlH_4$, followed by halogenation, eg treatment with thionyl chloride (Scheme 3).

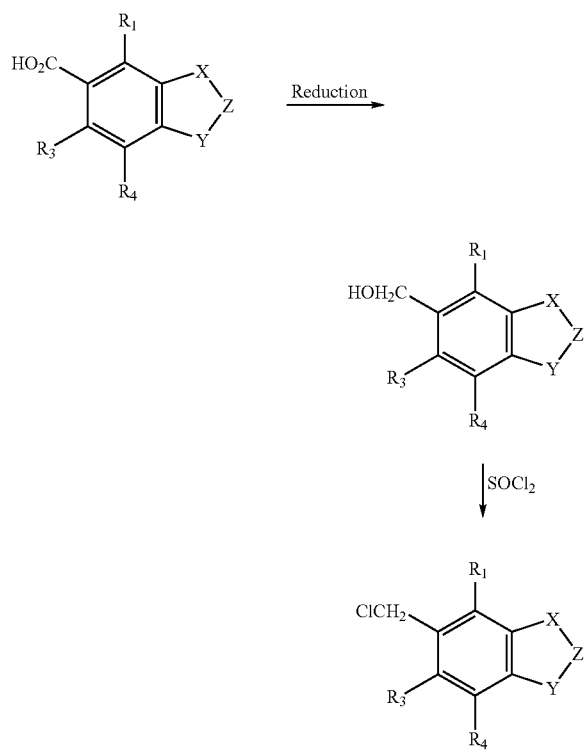

Coupling of compounds wherein $R_2$ is $CH_2$halo with a $C_{1-4}$alkylhalide, halo$(CH_2)_n$heterocyclyl in the presence of CuLi affords the corresponding compounds where the $R_2$ substituent is $C_{1-6}$alkyl, $(CH_2)_n$heterocyclyl.

Reaction of $CH_2$halo with $NH_2$—NH—C(=NH)—$NH_2$ in the presence of base affords access to compounds wherein $R_2$ is $CH_2$—NH—NH—C(=NH)—$NH_2$. Alternatively, reaction of the $CH_2$halo group with halo$(CH_2)_p$NH—NH—C(=NH)—$NH_2$ (where p is 1 or 2), affords the group $(CH_2)_p$NH—NH—C(=NH)—$NH_2$ where p is 2 or 3.

Other embodiments of formula (I) may be prepared by known methods. For example, furan, thiophene and indole derivatives may be prepared by cyclisation of hydroxy acids, thiol acids or amino acids respectively. For example,

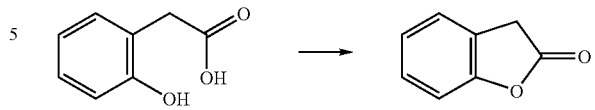

The term "salt, or prodrug" includes any pharmaceutically acceptable salt, ester, solvate, hydrate or any other compound which, upon administration to the recipient is capable of providing (directly or indirectly) a compound of formula (I) as described herein. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate, or where a free amino group is converted into an amide. Procedures for acylating hydroxy or amino groups of the compounds of the invention are well known in the art and may include treatment of the compound with an appropriate carboxylic acid, anhydride or acylchloride in the presence of a suitable catalyst or base.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that some compounds of formula (I) may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In another aspect, the invention provides a method of treating, preventing or diagnosing a disease or condition wherein MIF cytokine or biological activity is implicated comprising the administration of a treatment, prevention or diagnostic effective amount of a compound of formula (I) or a pharmaceutically acceptable salt or prodrug thereof to a subject in need thereof.

In a further aspect, there is provided the use of a compound of formula (I) or a pharmaceutically acceptable salt or prodrug thereof in the manufacture of a medicament for the treatment, prevention or diagnosis of a disease or condition wherein MIF cytokine or biological activity is implicated.

In a further aspect of the invention there is provided an agent for the treatment, prevention or diagnosis of a disease or condition wherein MIF cytokine or biological activity is implicated comprising a compound of formula (I) or a pharmaceutically acceptable salt or prodrug thereof.

As used herein, MIF includes human or other animal MIF and derivatives and naturally occurring variants thereof which at least partially retain MIF cytokine or biological activity. Thus, the subject to be treated may be human or other animal such as a mammal. Non-human subjects include, but are not limited to primates, livestock animals (eg sheep, cows, horses, pigs, goats), domestic animals (eg dogs, cats), birds and laboratory test animals (eg mice rats, guinea pigs, rabbits). MIF is also expressed in plants (thus "MIF" may also refer to plant MIF) and where appropriate, compounds of formula (I) may be used in botanical/agricultural applications such as crop control.

Reference herein to "cytokine or biological activity" of MIF includes the cytokine or biological effect on cellular function via autocrine, endocrine, paracrine, cytokine, hormone or growth factor activity or via intracellular effects.

In particular, the invention provides a method of treating, diagnosing or preventing autoimmune diseases, solid or haemopoeitic tumours, or chronic or acute inflammatory diseases, including a disease or condition selected from the group comprising:

Rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, connective tissue diseases (including but not limited to systemic lupus erythematosus, systemic sclerosis, polymyositis, dermatomyositis, Sjögren's syndrome), vasculitides (including but not limited to polyarteritis nodosa, Wegener's granulomatosis, Churg-Strauss syndrome), glomerulonephritis, interstitial nephritis, inflammatory bowel disease (including but not limited to ulcerative colitis, Crohn's disease), peptic ulceration, gastritis, oesophagitis, liver disease (including but not limited to cirrhosis, hepatitis), autoimmune diseases (including but not limited to diabetes mellitus, thyroiditis, myasthenia gravis, sclerosing cholangitis, primary biliary cirrhosis), pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome), cancers whether primary or metastatic (including but not limited to colon cancer, lymphoma, lung cancer, melanoma, prostate cancer, breast cancer, stomach cancer, leukemia, cervical cancer, multiple myeloma and metastatic cancer), atherosclerosis (eg ischaemic heart disease, myocardial infarction, stroke, peripheral vascular disease), disorders of the hypothalamic-pituitary-adrenal axis, brain disorders (eg dementia, Alzheimer's disease, multiple sclerosis, demyelinating diseases), corneal disease, iritis, iridocyclitis, cataracts, uveitis, sarcoidosis, diseases characterised by modified angiogenesis (eg diabetic retinopathy, rheumatoid arthritis, cancer), endometrial function (menstruation, implantation, parturition, endometriosis), psoriasis, endotoxic (septic) shock, exotoxic (septic) shock, infective (true septic) shock, other complications of infection, pelvic inflammatory disease, transplant rejection, allergies, allergic rhinitis, bone diseases, (eg osteoporosis, Paget's disease), atopic dermatitis, UV(B)-induced dermal cell activation (eg sunburn, skin cancer), malarial complications, diabetes mellitus, pain, inflammatory consequences of trauma or ischaemia, testicular dysfunctions and wound healing, comprising the administration of a treatment, diagnosis or prevention effective amount of a compound of formula (I) or a pharmaceutically acceptable salt or prodrug thereof to a subject in need thereof.

In a preferred embodiment, the invention provides a method of treating, diagnosing or preventing autoimmune diseases, solid or haemopoeitic tumours, or chronic or acute inflammatory diseases, including a disease or condition selected from the group comprising rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis, Reiter's syndrome), crystal arthropathies (including but not limited to gout, pseudogout, calcium pyrophosphate deposition disease), connective tissue diseases (including but not limited to systemic lupus erythematosus, systemic sclerosis, polymyositis, dermatomyositis, Sjögren's syndrome), glomerulonephritis, interstitial nephritis, inflammatory bowel disease (including but not limited to ulcerative colitis, Crohn's disease), peptic ulceration, gastritis, oesophagitis, liver disease (including but not limited to cirrhosis, hepatitis), autoimmune diseases (including but not limited to diabetes mellitus, thyroiditis, myasthenia gravis), pulmonary diseases (including but not limited to diffuse interstitial lung diseases, asthma, bronchitis, chronic obstructive pulmonary disease, adult respiratory distress syndrome), cancers whether primary or metastatic (including but not limited to colon cancer, lymphoma, lung cancer, melanoma, prostate cancer, breast cancer, stomach cancer, leukemia, cervical cancer, multiple myeloma and metastatic cancer), atherosclerosis (eg ischaemic heart disease, myocardial infarction), brain disorders (eg multiple sclerosis, demyelinating diseases), iritis, iridocyclitis, uveitis, sarcoidosis, diseases characterised by modified angiogenesis (eg diabetic retinopathy, rheumatoid arthritis, cancer), psoriasis, endotoxic (septic) shock, exotoxic (septic) shock, infective (true septic) shock, pelvic inflammatory disease, transplant rejection, allergies, allergic rhinitis, bone diseases (including but not limited to osteoporosis, Paget's disease), atopic dermatitis, malarial complications, diabetes mellitus, pain, inflammatory consequences of trauma or ischaemia, and wound healing, comprising the administration of a treatment, diagnosis or prevention effective amount of a compound of formula (I) or a pharmaceutically acceptable salt or prodrug thereof to a subject in need thereof.

In yet another preferred embodiment of the invention there is provided a method of treating, diagnosing or preventing autoimmune diseases, solid or haemopoeitic tumours, or chronic or acute inflammatory diseases, including a disease or condition selected from the group comprising rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis), crystal arthropathies (including but not limited to gout, pseudogout, calcium pyrophosphate deposition disease), connective tissue diseases (including but not limited to systemic lupus erythematosus, systemic sclerosis, polymyositis, dermatomyositis), glomerulonephritis, interstitial nephritis, inflammatory bowel disease (including but not limited to ulcerative colitis, Crohn's disease), liver disease (including but not limited to cirrhosis, hepatitis), autoimmune diseases (including but not limited to diabetes mellitus, thyroiditis, myasthenia gravis,), pulmonary diseases (including but not limited to asthma, chronic obstructive pulmonary disease, adult respiratory distress syndrome), cancers whether primary or metastatic (including but not limited to colon cancer, lymphoma, lung cancer, leukemia, cervical cancer, multiple myeloma and metastatic cancer), atherosclerosis (eg ischaemic heart disease, myocardial infarction), brain disorders (eg multiple sclerosis, demyelinating diseases), uveitis, sarcoidosis, diseases characterised by modified angiogenesis (eg diabetic retinopathy, rheumatoid arthritis, cancer), psoriasis, endotoxic (septic) shock, exotoxic (septic) shock, infective (true septic) shock, transplant rejection, allergies, allergic rhinitis, bone diseases (including but not limited to osteoporosis, Paget's disease), atopic dermatitis, malarial complications, diabetes mellitus, pain, inflammatory consequences of trauma or ischaemia, and wound healing, comprising the administration of a treatment, diagnosis or prevention effective amount of a compound of formula (I) or a pharmaceutically acceptable salt or prodrug thereof to a subject in need thereof.

In yet another preferred embodiment, the invention provides a method of treating, diagnosing or preventing autoimmune diseases, solid or haemopoeitic tumours, or chronic or acute inflammatory diseases, including a disease or condition selected from the group comprising rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis), connective tissue diseases (including but not limited to systemic lupus erythematosus, systemic sclerosis,), glomerulonephritis, interstitial nephritis, inflammatory bowel disease (including but not limited to ulcerative colitis, Crohn's disease), liver disease (including but not limited to cirrhosis, hepatitis), autoimmune diseases (including but not limited to diabetes mellitus, thyroiditis, myasthenia gravis,), pulmonary diseases (including but not limited to asthma, chronic obstructive pulmonary disease, adult respiratory distress syndrome), cancers whether primary or metastatic (including but not limited to colon cancer, lymphoma, lung cancer, leukemia, cervical cancer, multiple myeloma and metastatic cancer), atherosclerosis (eg ischaemic heart disease, myocardial infarction), brain disorders (eg multiple sclerosis, demyelinating diseases), psoriasis, transplant rejection, allergies, allergic rhinitis, atopic dermatitis, and wound healing, comprising the administration of a treatment, diagnosis or prevention effective amount of a compound of formula (I) or a pharmaceutically acceptable salt or prodrug thereof to a subject in need thereof.

In a further preferred embodiment, the invention provides a method of treating, diagnosing or preventing autoimmune diseases, or chronic or acute inflammatory diseases, including a disease or condition selected from the group comprising rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis,), connective tissue diseases (including but not limited to systemic lupus erythematosus, systemic sclerosis,), glomerulonephritis, interstitial nephritis, inflammatory bowel disease (including but not limited to ulcerative colitis, Crohn's disease), liver disease (including but not limited to cirrhosis, hepatitis), autoimmune diseases (including but not limited to diabetes mellitus, thyroiditis, myasthenia gravis,), pulmonary diseases (including but not limited to asthma, chronic obstructive pulmonary disease, adult respiratory distress syndrome), atherosclerosis (eg ischaemic heart disease, myocardial infarction), brain disorders (eg multiple sclerosis, demyelinating diseases), psoriasis, transplant rejection, allergies, allergic rhinitis, atopic dermatitis, and wound healing, comprising the administration of a treatment, diagnosis or prevention effective amount of a compound of formula (I) or a pharmaceutically acceptable salt or prodrug thereof to a subject in need thereof.

In yet a further preferred embodiment, the invention provides a method of treating, diagnosing or preventing autoimmune diseases, or chronic or acute inflammatory diseases, including a disease or condition selected from the group comprising rheumatic diseases (including but not limited to rheumatoid arthritis, psoriatic arthritis, polymyalgia rheumatica), spondyloarthropathies (including but not limited to ankylosing spondylitis,), connective tissue diseases (including but not limited to systemic lupus erythematosus), glomerulonephritis, interstitial nephritis, inflammatory bowel disease (including but not limited to ulcerative colitis, Crohn's disease), liver disease (including but not limited to cirrhosis, hepatitis), autoimmune diseases (including but not limited to diabetes mellitus, thyroiditis, myasthenia gravis,), pulmonary diseases (including but not limited to asthma, chronic obstructive pulmonary disease, adult respiratory distress syndrome), atherosclerosis (eg ischaemic heart disease, myocardial infarction), brain disorders (eg multiple sclerosis, demyelinating diseases), psoriasis, transplant rejection, allergic rhinitis, and atopic dermatitis, comprising the administration of a treatment, diagnosis or prevention effective amount of a compound of formula (I) or a pharmaceutically acceptable salt or prodrug thereof to a subject in need thereof.

In yet a further preferred embodiment, the invention provides a method of treating, diagnosing or preventing autoimmune diseases, or chronic or acute inflammatory diseases, including a disease or condition selected from the group comprising rheumatic diseases (including but not limited to rheumatoid arthritis, psoriatic arthritis, polymyalgia rheumatica), spondyloarthropathies (including but not limited to ankylosing spondylitis), connective tissue diseases (including but not limited to systemic lupus erythematosus), glomerulonephritis, interstitial nephritis, inflammatory bowel disease (including but not limited to ulcerative colitis, Crohn's disease), pulmonary diseases (including but not limited to asthma, chronic obstructive pulmonary disease, adult respiratory distress syndrome), atherosclerosis (eg ischaemic heart disease, myocardial infarction), brain disorders (eg multiple sclerosis, demyelinating diseases), psoriasis, and transplant rejection, comprising the administration of a treatment, diagnosis or prevention effective amount of a compound of formula (I) or a pharmaceutically acceptable salt or prodrug thereof to a subject in need thereof.

A further aspect of the invention provides for the use of a compound of formula (I) or a pharmaceutically acceptable salt or prodrug thereof in the manufacture of a medicament for the treatment of a disease or condition as above.

As used herein, the term "effective amount" relates to an amount of compound which, when administered according to a desired dosing regimen, provides the desired MIF cytokine inhibiting or treatment or therapeutic activity, or disease/condition prevention.

Dosing may occur at intervals of minutes, hours, days, weeks, months or years or continuously over any one of these periods. A cytokine or biological activity inhibiting amount is an amount which will at least partially inhibit the cytokine or biological activity of MIF. A therapeutic, or treatment, effective amount is an amount of the compound which, when administered according to a desired dosing regimen, is sufficient to at least partially attain the desired therapeutic effect, or delay the onset of, or inhibit the progression of or halt or partially or fully reverse the onset or progression of a particular disease condition being treated. A prevention effective amount is an amount of compound which when administered according to the desired dosing regimen is sufficient to at least partially prevent or delay the onset of a particular disease or condition. A diagnostic effective amount of compound is an amount sufficient to bind to MIF to enable detection of the MIF-compound complex such that diagnosis of a disease or condition is possible.

Suitable dosages may lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts and dosing regimens can be determined by the attending physician or veterinarian and may depend on the desired level of inhibiting activity, the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition.

In a further aspect of the invention, there is provided a pharmaceutical composition comprising a compound of formula (I) or a pharmaceutically acceptable salt or prodrug thereof together with a pharmaceutically acceptable carrier, diluent or excipient.

The formulation of such compositions is well known to those skilled in the art. The composition may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, inhalational, nasal, transdermal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Depending on the disease or condition to be treated, it may or may not be desirable for a compound of formula (I) to cross the blood/brain barrier. Thus the compositions for use in the present invention may be formulated to be water or lipid soluble.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg inert diluent, preservative, disintegrant (eg. sodium starch glycolate, cross-linked polyvinyl pyrrolidone, cross-linked sodium carboxymethyl cellulose)) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

The compounds of formula (I) may also be administered intranasally or via inhalation, for example by atomiser, aerosol or nebulizer means.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal devices, such as patches, may also be used to administer the compounds of the invention.

Compositions for rectal administration may be presented as a suppository with a suitable carrier base comprising, for example, cocoa butter, gelatin, glycerin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

It will be recognised that other therapeutically active agents such as anti-inflammatory (eg steroids such as glucocorticoids) or anti-cancer agents may be used in conjunction with a compound of formula (I). Compounds of formula (I) when administered in conjunction with other therapeutically active agents may exhibit an additive or synergistic effect. These may be administered simultaneously, either as a combined form (ie as a single composition containing the active agents) or as discrete dosages. Alternatively, the other therapeutically active agents may be administered sequentially or separately with the compounds of the invention. Thus, the invention also relates to kits and combinations, comprising a compound of formula (I) and one or more other therapeutically active ingredients for use in the treatment of diseases or conditions described herein.

Without being limiting, examples of agents which could be used in combination with a compound of formula (I) include: glucocorticoids, antirheumatic drugs (including but not limited to methotrexate, leflunomide, sulphasalazine, hydroxycholorquine, gold salts); immunosuppressive drugs (including but not limited to cyclosporin, mycophenyllate mofetil, azathioprine, cyclophosphamide); anti-cytokine therapies (including but not limited to antagonists of, antibodies to, binding proteins for, or soluble receptors for tumor necrosis factor, interleukin 1, interleukin 3, interleukin 5, interleukin 6, interleukin 8, interleukin 12, interleukin 18, interleukin 17, and other pro-inflammatory cytokines as may be found relevant to pathological states); antagonists or inhibitors of mitogen-activated protein (MAP) kinases (including but not limited to antagonists or inhibitors of extracellular signal-regulated kinases (ERK), the c-Jun N-terminal kinases/stress-activated protein kinases (JNK/SAPK), and the p38 MAP kinases, and other kinases or enzymes or proteins involved in MAP kinase-dependent cell activation); antagonists or inhibitors of the nuclear factor kappa-B (NF-κB) signal transduction pathway (including but not limited to antagonists or inhibitors of I-κB-kinase, interleukin receptor activated kinase, and other kinases or enzymes or proteins involved in NF-κB-dependent cell activation); antibodies, protein therapeutics, or small molecule therapeutics interacting with adhesion molecules and co-stimulatory molecules (including but not limited to therapeutic agents directed against intercellular adhesion molecule-1, CD40, CD40-ligand, CD28, CD4, CD-3, selectins such as P-selectin or E-selectin); bronchodilators such as O-adrenoceptor agonists or anti-cholinergics; antagonists of eicosanoid synthesis pathways such as non-steroidal anti-inflammatory drugs, cyclooxygenase-2 inhibitors, thromboxane inhibitors, or lipoxygenase inhibitors; antibodies or other agents directed against leukocyte surface antigens (including but not limited to antibodies or other agents directed against CD3, CD4, CD5, CD19, CD20, HLA molecules); agents used for the treatment of inflammatory bowel disease (including but not limited to sulphasalazine, mesalazine, salicylic acid derivatives); anti-cancer drugs (including but not limited to cytotoxic drugs, cytolytic drugs, monoclonal antibodies).

In another aspect, the invention provides a method of treating or preventing a disease or condition wherein MIF cytokine or biological activity is implicated comprising:

administering to a mammal a compound of formula (I) or a pharmaceutically acceptable salt or prodrug thereof and a second therapeutic agent.

In a preferred embodiment of the invention, the second therapeutic agent is a glucocorticoid compound. The mechanism through which MIF antagonises the effects of glucocorticoids has not been fully eludicated. Glucocorticoid effects on inflammation are dependent upon the transactivation of genes which exert inhibitory effects on cell activation, or on the transrepression of genes which exert stimulatory effects on cell activation. Transrepression effects are in part mediated via effects on intra-cellular signal transduction pathways such as the nuclear factor κB (NF-κB) and mitogen activated protein kinase (MAPK) pathways.

Figure 3:
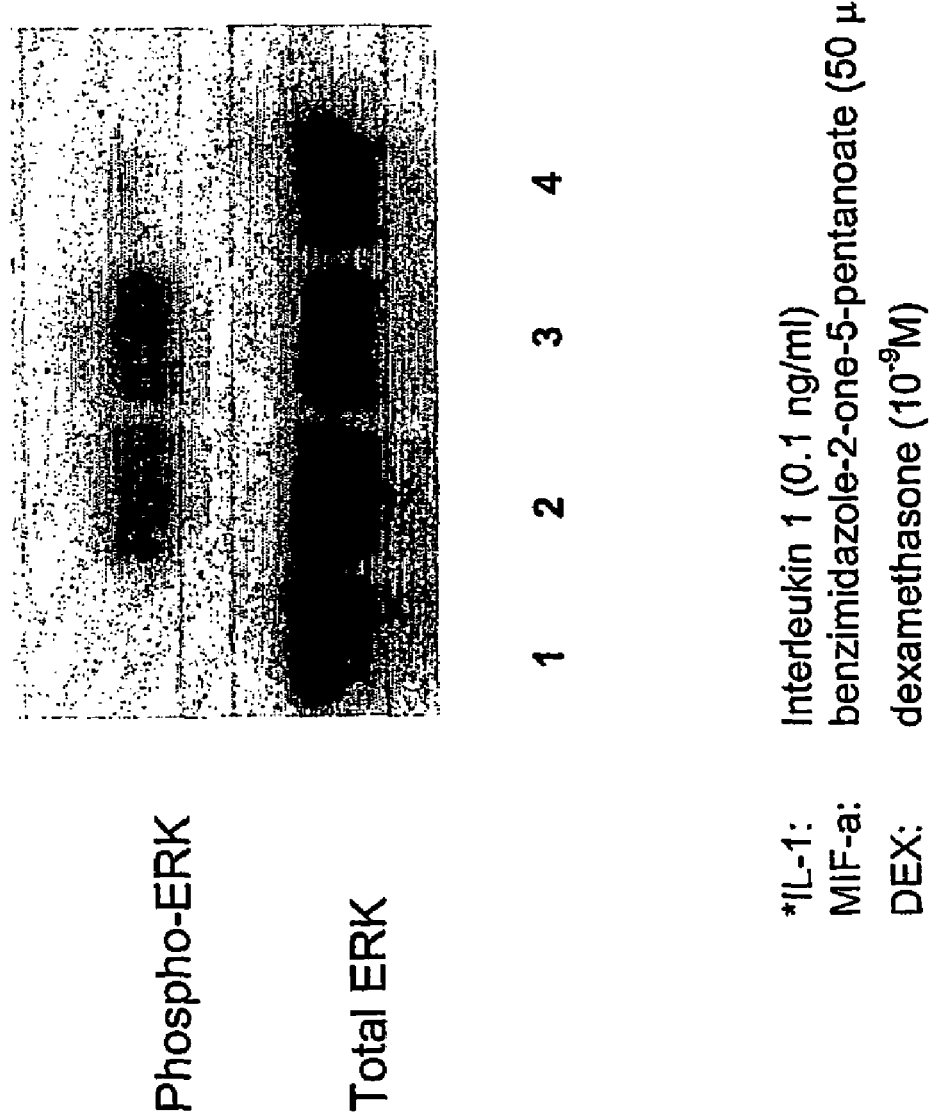
FIG. 3 graphically depicts the effect of MIF antagonist, benzimidazol-2-one-5-pentanoate (compound 5) and dexamethasone on IL-1 induced phosphorylation (activation) of ERK (extracellular signal regulated kinase), as detected by Western blotting.

Without wishing to be bound by theory, it is possible that suppression of activation of signal transduction pathways by a MIF inhibitor may allow a glucocorticoid to be more effective. The ability of glucocorticoids to inhibit the activation of MAPK pathways is uncertain. Glucocorticoids have been variously reported either to suppress, or to be unable to suppress, MAPK activation under various conditions (13-15). Activation of the MAPK pathway known as ERK (extracellular signal regulated kinase, also known as p44/42 MAP kinase), as measured by the phosphorylation of ERK protein detected with a phospho-specific antibody, is increased by stimuli such as interleukin-1 (IL-1) (FIG. 3). The ERK pathway is also known to be activated by MIF (16). In experiments using human dermal fibroblasts, the glucocorticoid dexamethasone does not inhibit ERK pathway activation by IL-1. The combination of dexamethasone with a compound that inhibits the cytokine or biological activity of MIF, however, was able to inhibit ERK activation (FIG. 3).

Notwithstanding the incomplete understanding of the interacting pathways involved, it is possible that administration of a compound which inhibits the cytokine or biological activity of MIF in combination with a glucocorticoid exerts inhibitory effects on signal transduction pathways that are greater than the effects of the glucocorticoid alone. Where these signal transduction pathways are known to be important in the regulation of cell activation in conditions such as inflammatory diseases, it is likely that this greater effect would permit the use of lower doses of the glucocorticoid in a given patient; that is, the compound which inhibits the cytokine or biological activity of MIF would have a "steroid-sparing" effect.

In another aspect, the present invention provides a method of prophylaxis or treatment of a disease or condition for which treatment with a glucocorticoid is indicated, said method comprising:

administering to a mammal a glucocorticoid and a compound of formula (I) or a pharmaceutically acceptable salt or prodrug thereof.

In yet another aspect, the present invention provides a method of treating steroid-resistant diseases comprising:

administering to a mammal a glucocorticoid and a compound of formula (I) or a pharmaceutically acceptable salt or prodrug thereof.

In a further aspect, the present invention provides a method of enhancing the effect of a glucocorticoid in mammals comprising administering a compound of formula (I) or a pharmaceutically acceptable salt or prodrug thereof, simultaneously, separately or sequentially with said glucocorticoid.

In yet a further aspect, the present invention provides a composition comprising a glucocorticoid and a compound of formula (I) or a pharmaceutically acceptable salt or prodrug thereof.

In a further aspect of the invention there is provided a use of a glucocorticoid in the manufacture of a medicament for administration with a compound of formula (I) or a pharmaceutically acceptable salt or prodrug thereo, for the treatment or prophylaxis of a disease or condition for which treatment with a glucocorticoid is indicated.

In yet a further aspect of the invention there is provided a use of a compound of formula (I) or a pharmaceutically acceptable salt or prodrug thereof, in the manufacture of a medicament for administration with a glucocorticoid for the treatment or prophylaxis of a disease or condition for which treatment of a glucocorticoid is indicated.

In yet a further aspect of the invention there is provided a use of a glucocorticoid and a compound of formula (I) or a pharmaceutically acceptable salt or prodrug thereof in the manufacture of a medicament for the treatment or prophylaxis of a disease or condition for which treatment with a glucocorticoid is indicated.

Preferably the amount of glucocorticoid used in the methods, uses and compositions of the invention is less than the amount which would be effective in the absence of the compound of formula (I). In the treatment of steroid-resistant diseases or conditions which are not responsive to glucocorticoids, any amount of glucocorticoid which is effective in combination with a compound of formula (I) is considered less than the amount which would be effective in the absence of a compound formula (I). Accordingly, the invention provides a steroid-sparing therapy.

In preferred embodiments of the invention, the glucocorticoid and the compound of formula (I) are used to treat or prevent a disease or condition in a mammal, preferably in a human subject.

The term "disease or condition for which treatment with a glucocorticoid is indicated" refers to diseases or conditions which are capable of being treated by administration of a glucocorticoid including but not limited to autoimmune diseases, solid or haemopoeitic tumours, or chronic or acute inflammatory diseases. Examples of such diseases or conditions include:

Rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, connective tissue diseases (including but not limited to systemic lupus erythematosus, systemic sclerosis, polymyositis, dermatomyositis, Sjögren's syndrome), vasculitides (including but not limited to polyarteritis nodosa, Wegener's granulomatosis, Churg-Strauss syndrome), glomerulonephritis, interstitial nephritis, inflammatory bowel disease (including but not limited to ulcerative colitis, Crohn's disease), peptic ulceration, gastritis, oesophagitis, liver disease (including but not limited to cirrhosis, hepatitis), autoimmune diseases (including but not limited to diabetes mellitus, thyroiditis, myasthenia gravis, sclerosing cholangitis, primary biliary cirrhosis), pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome), cancers whether primary or metastatic (including but not limited to colon cancer, lymphoma, lung cancer, melanoma, prostate cancer, breast cancer, stomach cancer, leukemia, cervical cancer, multiple myeloma and metastatic cancer), atherosclerosis (eg ischaemic heart disease, myocardial infarction, stroke, peripheral vascular disease), disorders of the hypothalamic-pituitary-adrenal axis, brain disorders (eg dementia, Alzheimer's disease, multiple sclerosis, demyelinating diseases), corneal disease, iritis, iridocyclitis, cataracts, uveitis, sarcoidosis, diseases characterised by modified angiogenesis (eg diabetic retinopathy, rheumatoid arthritis, cancer), endometrial function (menstruation, implantation, parturition, endometriosis), psoriasis, endotoxic (septic) shock, exotoxic (septic) shock, infective (true septic) shock, other complications of infection, pelvic inflammatory disease, transplant rejection, allergies, allergic rhinitis, bone diseases (eg osteoporosis, Paget's disease), atopic dermatitis, UV(B)-induced dermal cell activation (eg sunburn, skin cancer), malarial complications, diabetes mellitus, pain, inflammatory consequences of trauma or ischaemia, testicular dysfunctions and wound healing.

These diseases or conditions may also include steroid-resistant diseases or conditions where treatment with a glucocorticoid is indicated, but where the glucocorticoid is ineffective or is not as effective as expected.

Compounds of formula (I) may be particularly useful in combination with a glucocorticoid, for the treatment of a disease or condition selected from autoimmune diseases, or chronic or acute inflammatory diseases, including rheumatic diseases (including but not limited to rheumatoid arthritis, osteoarthritis, psoriatic arthritis, polymyalgia rheumatica) spondyloarthropathies (including but not limited to ankylosing spondylitis, reactive arthritis, Reiter's syndrome), crystal arthropathies (including but not limited to gout, pseudogout, calcium pyrophosphate deposition disease), connective tissue diseases (including but not limited to systemic lupus erythematosus, systemic sclerosis, polymyositis, dermatomyositis, Sjögren's syndrome), vasculitides (including but not limited to polyarteritis nodosa, Wegener's granulomatosis, Churg-Strauss syndrome), glomerulonephritis, interstitial nephritis, inflammatory bowel disease (including but not limited to ulcerative colitis, Crohn's disease), liver disease (including but not limited to cirrhosis, hepatitis), autoimmune diseases (including but not limited to diabetes mellitus, thyroiditis, myasthenia gravis, sclerosing cholangitis, primary biliary cirrhosis), pulmonary diseases (including but not limited to diffuse interstitial lung diseases, fibrosing alveolitis, asthma, bronchitis, bronchiectasis, chronic obstructive pulmonary disease, adult respiratory distress syndrome), cancers whether primary or metastatic (including but not limited to myeloma, lymphoma, lung cancer, leukemia, cervical cancer and metastatic cancer), atherosclerosis (eg ischaemic heart disease, myocardial infarction, stroke, peripheral vascular disease), disorders of the hypothalamic-pituitary-adrenal axis, brain disorders (including but not limited to multiple sclerosis, demyelinating diseases), corneal disease, iritis, iridocyclitis, uveitis, sarcoidosis, psoriasis, endotoxic (septic) shock, exotoxic (septic) shock, infective (true septic) shock, other complications of infection, transplant rejection, allergies, allergic rhinitis, bone diseases (including but not limited to osteoporosis), atopic dermatitis, malarial complications, inflammatory consequences of trauma or ischaemia, and wound healing.

The combination of glucocorticoid and compound of formula (I) may be particularly useful when used in a steroid-sparing manner. The term "steroid-sparing" refers to a combination therapy method that allows a reduction in the amount of glucocorticoid administered while still providing an effective therapy for the disease or condition being treated or prevented.

Steroid-resistant diseases or conditions are diseases or conditions for which treatment with a glucocorticoid is indicated, but where the glucocorticoid is ineffective or is not as effective as expected. This term encompasses diseases or conditions for which the effective dose of glucocorticoid results in unacceptable side effects and/or toxicity. Some steroid-resistant diseases or conditions may require a dosage of glucocorticoid so large that they are considered non-responsive and therefore are not able to be successfully treated with glucocorticoids. Some steroid-resistant diseases or conditions may require a large dosage of glucocorticoid to achieve only a small effect on the symptoms of the disease or condition. Furthermore, some patients, diseases or conditions present with symptoms that do not respond to treatment with a glucocorticoid, or may become less sensitive to glucocorticoid treatment over time. Examples of diseases which may commonly exhibit features of steroid-resistance include asthma, chronic obstructive pulmonary disease, rheumatoid arthritis, glomerulonephritis, interstitial nephritis, systemic lupus erythematosus, inflammatory bowel disease and transplant rejection.

Glucocorticoids are a group of steroid hormones, which are used to treat or prevent a wide range of diseases or conditions. Suitable glucocorticoids may be synthetic or naturally occurring and include but are not limited to prednisolone, prednisone, cortisone acetate, beclamethasone, fluticasone, hydrocortisone, dexamethasone, methyl prednisolone, triamcinolone, budesonide and betamethasone. A person skilled in the art would be able to identify other suitable glucocorticoids that may benefit from being used in a combination treatment with a MIF antagonist.

In preferred embodiments of the invention, the glucocorticoid used is selected from prednisone, prednisolone, hydrocortisone, fluticasone, beclamethasone, betamethasone, methyl prednisolone, budesonide, triamcinolone, dexamethasone and cortisone. Most preferably, the glucocorticoid is selected from prednisone, prednisolone, methyl prednisolone, fluticasone and beclamethasone. Beclamethasone and fluticasone are particularly preferred for treating asthma. Prednisone, prednisolone and methyl prednisolone are particularly preferred in the treatment of systemic or local inflammatory diseases.

The amounts of glucocorticoid and compound of formula (I) are selected such that in combination they provide complete or partial treatment or prophylaxis of a disease or condition for which a glucocorticoid is indicated. The amount of compound formula (I) is preferably an amount that will at least partially inhibit the cytokine or biological activity of MIF. The amount of glucocorticoid is preferably less than the amount required in the absence of the compound of formula (I). The amounts of glucocorticoid and compound of formula (I) used in a treatment or therapy are selected such that in combination they at least partially attain the desired therapeutic effect, or delay onset of, or inhibit the progression of, or halt or partially or fully-reverse the onset or progression of the disease or condition being treated. The amounts of glucocorticoid and compound of formula (I) used in the prophylaxis of a disease or condition are selected such that in combination they at least partially prevent or delay the onset of the disease or condition. Dosing may occur at intervals of minutes, hours, days, weeks, months or years or continuously over any one of these periods.

Suitable doses of a compound of formula (I) may lie within the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 μg to 1 mg per kg of body weight per dosage.

Suitable dosage amounts of glucocorticoids will depend, in part, on the mode of administration and whether the dosage is being administered in a single, daily or divided dose, or as a continuous infusion. When administered orally, intravenously, intramuscularly, intralesionally or intracavity (eg. intra-articular, intrathecal, intrathoracic), dosages are typically between 1 mg to 1000 mg, preferably 1 mg to 100 mg, more preferably 1 mg to 50 mg or 1 mg to 10 mg per dose. When administered topically or by inhalation as a single, daily or divided dose, dosages are typically 1 ng to 1 μg, 1 ng to 1 mg or 1 pg to 1 μg.

Suitable dosage amounts and dosing regimens can be determined by the attending physician or veterinarian and may depend on the desired level of inhibiting activity, the particular condition being treated, the severity of the condition as well as the general age, health and weight of the subject.

The glucocorticoid and compound of formula (I) may be administered simultaneously or sequentially. The active ingredients may be administered alone but are preferably administered as a pharmaceutically acceptable composition or separate pharmaceutically acceptable compositions.

The formulation of such compositions is well known to those skilled in the art and are described above in relation to compounds of formula (I). The composition or compositions may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

Preferred unit dosage compositions are those containing a daily dose or unit, daily sub-dose, as herein above described, or an appropriate fraction thereof, of the glucocorticoids and/or compound of formula (I) which inhibit the cytokine or biological activity of MIF.

In one preferred aspect of the invention, the compounds of formula (I) may be administered together with, simultaneously or sequentially, glucocorticoids. In such a therapy, the amount of glucocorticoid required may be significantly reduced.

The compounds of formula (I), either as the only active agent or together with another active agent, e.g. a glucocorticoid, may also be presented for use in veterinary compositions. These may be prepared by any suitable means known in the art. Examples of such compositions include those adapted for:

(a) oral administration, external application (eg drenches including aqueous and non-aqueous solutions or suspensions), tablets, boluses, powders, granules, pellets for admixture with feedstuffs, pastes for application to the tongue;

(b) parenteral administration, eg subcutaneous, intramuscular or intravenous injection as a sterile solution or suspension; and (c) topical application eg creams, ointments, gels, lotions, etc.

By virtue of their ability to bind to or antagonize MIF, compounds of formula (I) or salts or derivatives thereof may be used as laboratory or diagnostic or in vivo imaging reagents. Typically, for such use the compounds would be labelled in some way, for example, radio isotope, fluorescence or colorimetric labelling, or be chelator conjugated. In particular, compounds of formula (I) could be used as part of an assay system for MIF or as controls in screens for identifying other inhibitors. Those skilled in the art are familiar with such screens and could readily establish such screens using compounds of formula (I). Those skilled in the art will also be familiar with the use of chelate conjugated molecules for in vivo diagnostic imaging.

In a further aspect of the invention there is provided a compound of formula (III) or a pharmaceutically acceptable salt or prodrug thereof:

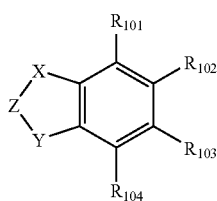

(III)

wherein

X is —O—, —NH— or —CH$_2$—;

Y is —NH—, —O—, —S— or —CH$_2$—;

Z is —C(O)—, —C(S)— or —S(O)—;

$R_{101}$ is selected from hydrogen, $C_{1-3}$alkyl, OH, SH, NH$_2$, NHC$_{1-3}$alkyl, F, Cl or Br;

$R_{102}$ is selected from $C_{1-20}$alkyl, $C_{2-20}$alkenyl, CO$_2$H, F, Cl, Br, CO$_2$R$_{105}$, (CH$_2$)$_w$R$_{106}$, C(O)N(R$_{107}$)$_2$, C(=N)NHC$_{1-6}$alkyl, SO$_2$C$_{1-6}$alkyl, C(O)[NHCH(R$_{108}$)C(O)]$_q$—OR$_{109}$, NH$_2$, C(O)sugar, CONH(CH$_2$)$_n$aryl, NHC(O)(CH$_2$)$_n$Sheterocyclyl, C(O)SC$_{1-6}$alkyl, C(O)(CH$_2$)$_n$CO$_2$H, SO$_{20}$C$_{1-10}$alkyl, SO$_2$NHC$_{1-10}$alkyl;

$R_{103}$ is selected from hydrogen, F, Cl, Br, C$_{1-6}$alkyl, —(CH$_2$)$_n$NH$_2$, —(CH$_2$)$_n$NO$_2$, —(CH$_2$)$_n$—OH, —(CH$_2$), —CF$_3$, —(CH$_2$)$_n$C(O)C$_{1-3}$alkyl or —(CH$_2$)$_n$—SH;

$R_{104}$ is selected from hydrogen, methyl, ethyl, CH$_2$C(R$_{110}$)$_3$, C(R$_{110}$)$_3$, —CH$_2$=CH$_2$, fluoro, chloro or bromo;

$R_{105}$ is selected from hydrogen, C$_{1-20}$alkyl, C$_{2-20}$alkenyl or (CH$_2$)$_t$OC$_{1-3}$alkyl;

$R_{106}$ is selected from SH, SC$_{1-4}$alkyl, OH, OC$_{1-6}$alkyl, sugar, CO$_2$H, NH$_2$, heterocyclyl or aryl;

Each $R_{107}$ is independently selected from hydrogen, C$_{1-20}$alkyl, C$_{2-20}$alkenyl, (CH$_2$)$_t$aryl and (CH$_2$)$_t$heterocyclyl;

$R_{108}$ is the characterising group of an amino acid;

$R_{109}$ is hydrogen, C$_{1-3}$alkyl;

Each $R_{110}$ is independently selected from hydrogen and halo; and n is 0 or an integer from 1 to 3, q is an integer from 1 to 5, w is an integer from 1 to 6; t is an integer from 1 to 10; wherein each alkyl, alkenyl, alkynyl, aryl and heterocyclyl may be optionally substituted.

Preferred compounds of formula (III) are benzimidazole compounds having formula (IV):

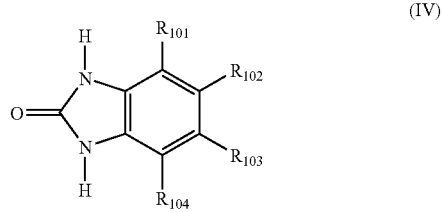

(IV)

wherein $R_{101}$ is selected from hydrogen, CH$_3$, OH, SH, NH$_2$, NHCH$_3$, F, Cl or Br;

$R_{102}$ is selected from C$_{1-20}$alkyl, C$_{2-20}$alkenyl, CO$_2$H, F, Cl, Br, CO$_2$R$_{105}$, (CH$_2$)$_w$R$_{106}$, C(O)N(R$_{107}$)$_2$, C(=N)NHC$_{1-6}$alkyl, SO$_2$C$_{1-6}$alkyl, C(O)[NHCH(R$_{108}$)C(O)]$_q$—OR$_{109}$, NH$_2$, C(O)sugar, CONH(CH$_2$)$_n$aryl, NHC(O)(CH$_2$)$_n$Sheterocyclyl, C(O)SC$_{1-6}$alkyl, C(O)(CH$_2$)$_n$CO$_2$H, SO$_{20}$C$_{1-10}$alkyl, SO$_2$NHC$_{1-10}$alkyl;

$R_{103}$ is selected from hydrogen, F, Cl, Br, C$_{1-6}$alkyl, (CH$_2$)$_n$NH$_2$, —(CH$_2$)$_n$NO$_2$, —(CH$_2$)$_n$—OH, —(CH$_2$), —CF$_3$, CH$_2$C(O)CH$_3$ or —(CH$_2$)$_n$—SH;

$R_{104}$ is selected from hydrogen, methyl, ethyl, CH$_2$CF$_3$, —CH$_2$=CH$_2$ fluoro, chloro or bromo;

$R_{105}$ is selected from hydrogen, C$_{1-10}$alkyl, C$_{2-10}$alkenyl, (CH$_2$)$_t$OC$_{1-3}$alkyl;

$R_{106}$ is selected from SH, SC$_{1-6}$alkyl, OH, OC$_{1-6}$alkyl, sugar, CO$_2$H, NH$_2$, heterocyclyl or aryl;

Each $R_{107}$ is independently selected from hydrogen, C$_{1-10}$alkyl, C$_{2-10}$alkenyl, (CH$_2$)$_t$aryl and (CH$_2$)$_t$heterocyclyl;

$R_{108}$ is the characterising group of an amino acid;

$R_{109}$ is hydrogen, C$_{1-3}$alkyl;

Each $R_{110}$ is independently selected from hydrogen and halo; and n is 0 or an integer from 1 to 3, q is an integer from 1 to 5, w is an integer from 1 to 6, t is an integer from 1 to 10; wherein each alkyl, alkenyl, alkynyl, aryl and heterocyclyl may be optionally substituted.

Preferably the compounds of formula (III) or formula (IV) are those in which at least one or more of the following definitions apply:

$R_{101}$ is hydrogen, F, Cl or Br;

$R_{102}$ is $C_{1-20}$alkyl, halogen, $NH_2$, $CO_2H$, $CO_2C_{1-10}$alkyl, C(O)sugar, $CO_2(CH_2)_nOC_{1-6}$alkyl, $CONHC_{1-10}$alkyl, $CONH(CH_2)_n$aryl, CO[NHCH($R_{107}$)CO]—OH, CO[NHCH($R_{107}$)CO]O$C_{1-3}$alkyl, NHC(O)($CH_2$)$_n$Sheterocyclyl, C(O)S$C_{1-6}$alkyl, C(O)($CH_2$)$_n$$CO_2H$, $SO_2OC_{10}$alkyl, $SO_2NHC_{1-10}$alkyl or C(=NH)NH$C_{1-6}$alkyl;

$R_{103}$ is hydrogen, halogen, $C_{1-3}$alkyl, $(CH_2)_nNH_2$, $(CH_2)_nNO$, $(CH_2)_nOH$ or $(CH_2)_nCF_3$;

$R_{104}$ is hydrogen, F, Cl or Br;

$R_{108}$ is the characterising group of an amino acid, preferably the characterising group from serine ($CH_2OH$) or phenylalanine ($CH_2Ph$);

n is 0 or an integer from 1 to 3; and wherein each alkyl or aryl group is optionally substituted, preferably with one or more OH, carboxylic acid or halo.

Preferred compounds of formula (III) include:
benzimidazol-2-one-5-n-pentanoate,
5[2(1-oxy-2-hydroxyethyl)ethyl]benzimidazol-2-one-5-carboxylate,
benzimidazol-2-one-5-methanoate,
benzimidazol-2-one-5-ethanoate,
pentyl-benzimidazole-2-thioxo-5-carboxylate,
3,4,5-tris(acetyloxy)-6-[(acetyloxy)methyl]tetrahydro-2H-pyran-2-yl-benzimidazole-2-one-5-carboxylate,
5-bromo-6-methylbenzimidazol-2-one,
5-hydroxy-6-methylbenzimidazol-2-one,
5-dodecanylbenzoimidazol-2-one,
4,5,7-tribromo-6-methylbenzimidazol-2-one,
4,5,6,7-tetrabromobenzimidazol-2-one,
5-methyl-6-nitrobenzimidazol-2-one,
5-amino-6-methylbenzimidazol-2-one,
N-(6-methylbenzimidazol-5-yl)-2-pyrimidin-2-yl-sulfanyl-acetamide
pentyl-benzimidazol-2-one-5-carbothioate
5-(benzimidazol-2(3H)-one-6-yl)-5-oxopentanoic acid
2(3H)-benzimidazolone-5-sulfonic acid pentyl ester,
2(3H)-benzimidazolone-5-sulfonic acid pentyl amide,
N-butyl-2-oxo-2,3-dihydro-1H-1,3-benzimidazole-5-carboximidamide
5-heptanoylbenzofuran-2(3H)-one,
methyl 3-hydroxy-2-{[(2-oxo-2,3-dihydro-1H-1,3-benzimidazol-5-yl)carbonyl]amino}propanoate,
3-hydroxy-2-{[(2-oxo-2,3-dihydro-1H-1,3-benzimidazol-5-yl)carbonyl]amino}propanoic acid,
methyl 2-{[(2-oxo-2,3-dihydro-1H-1,3-benzimidazol-5-yl)carbonyl]amino}-3-phenyl propanoate,
2-{[(2-oxo-2,3-dihydro-1H-1,3-benzimidazol-5-yl)carbonyl]amino}-3-phenyl propanoic acid, and
N-(3,4-dihydroxyphenethyl)-2-oxo-2,3-dihydro-1H-1,3-benzimidazole-5-carboxamide.

Unless the context indicates otherwise, reference to any prior art in this specification is not, and should not be taken as, an acknowledgment or any form of suggestion that that prior art forms part of the common general knowledge in Australia.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustration only and are not intended to limit the generality of the invention hereinbefore described.

EXAMPLES

Synthesis of Compounds of Formula (I)

Example 1

5-Methylbenzimidazol-2-one (2)

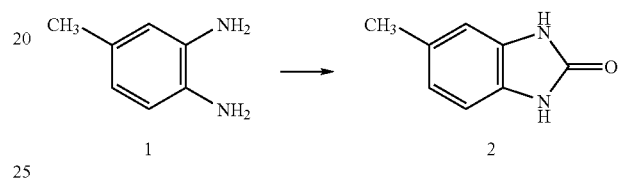

This was prepared as described by Harvey et al (12).

A solution of urea (6.00 g, 0.1000 mol) and 3,4-diaminotoluene (1) (12.20 g, 0.0999 mol) in pentan-1-ol (40 mL) was vigorously stirred and heated to reflux under a nitrogen atmosphere. After 2 hours the heating was discontinued and on cooling to room temperature a pink solid settled out. This was filtered off and recrystallised from boiling ethanol (17.98 g. in 400 mL) to give 2 crops of 5-methylbenzimidazol-2-one (2) as a pink powder. The total mass was recovered was 8.21 g (56% yield);

$R_f$: 0.40 (9:1 CHCl$_3$:MeOH),
mp: 300-302° C., lit.³ mp: 297-300° C.;
$^1$H NMR (CDCl$_3$/CD$_3$OD): δ 2.12 (s, 3H, CH$_3$), 6.63-6.70 (m, 3H, ArH);
LRESI mass spectrum: m/z 149 (100%, MH$^+$).

Example 2

Benzimidazol-2-one-5-carboxylic acid (4)

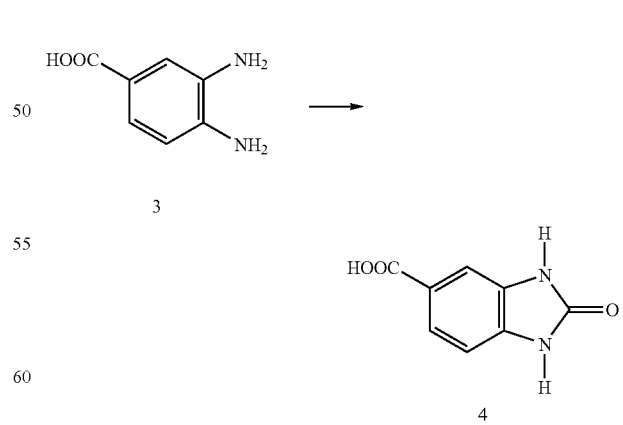

The method described by Harvey et al (12) and used in Example 1 for the preparation of 5-methylbenzimidazol-2-one (2) was used except this preparation started with 3,4-diaminobenzoic acid (3).

Urea (1.20 g, 0.0200 mol) and 3,4-diaminobenzoic acid (3) (3.04 g, 0.0200 mol) in pentan-1-ol (10 mL) was vigorously stirred and heated to reflux under a nitrogen atmosphere. The heating was discontinued after 4 hours and on cooling to room temperature, water (30 mL) was added. The pH was adjusted to 1 with conc. HCl. The resultant dark solid was filtered off, washed with further water (2×20 mL) and dried to give 3.00 g (84% yield) of benzimidazol-2-one-5-carboxylic acid (4) as a black powder, $R_f$: 0.09 (9:1 $CHCl_3$:MeOH), 0.20 (4:1 $CHCl_3$:MeOH), $^1$H NMR ($d_6$-DMSO): δ 6.98 (d, 1H, $J_{7,6}$ 8.1 Hz, H-7), 7.45 (d, 1H, $J_{4,6}$ 1.2 Hz, H-4), 7.60 (dd, 1H, H-6), 10.78 (bs, 1H, NH), 10.94 (bs, 1H, NH);

LRESI negative ion mass spectrum: m/z 177 (100%, M−H⁻).

Example 3

Benzimidazol-2-one-5-n-pentanoate (5)

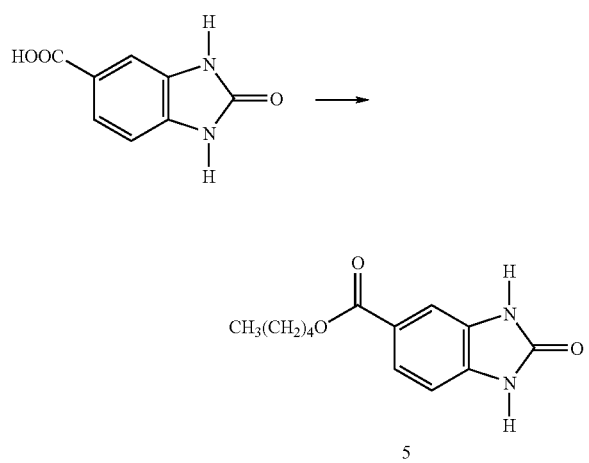

Benzimidazol-2-one-5-carboxylic acid (4) (250 mg, 0.9070 mmol) and Dowex 50 W-X8(H⁺) resin (250 mg) were suspended in pentan-1-ol (40 mL) and the mixture heated to reflux for 42 hours. The solid was filtered off and washed with methanol (3×20 mL) and the combined filtrates evaporated to dryness to give benzimidazol-2-one-5-n-pentanoate (5) (310 mg, 43% yield) as an off-white powder;

$R_f$: 0.63 (4:1 $CHCl_3$:MeOH), mp: 227-228° C., $^1$H NMR ($CDCl_3$/$CD_3OD$): δ 0.88-0.92 (pseudo t, 3H, $CH_3$), 1.33-1.43 (m, 4H, 2×$CH_2$), 1.70-1.79 (m, 2H, $CH_2$), 4.25-4.29 (pseudo t, 2H, $CH_2$), 7.04 (d, 1H, $J_{7,6}$ 8.4 Hz, H-7), 7.44 (bs, 1H, NH), 7.55 (bs, 1H, NH), 7.66 (bs, 1H, H-4), 7.75 (dd, 1H, $J_{6,5}$ 1.5 Hz, H-6);

LRESI negative ion mass spectrum: m/z 247 (100%, [M−H]⁻);

HRESI positive ion mass spectrum: $C_{13}H_{17}N_2O_3$ calculated 249.12391, $C_{13}H_{16}N_2O_3$ calculated C, 62.97; H, 6.50; N, 11.29. found C, 63.1, H, 6.54, N, 11.05.

Example 4

5[2(1-oxy-2-hydroxyethyl)ethyl]benzimidazol-2-one-5-carboxylate (6)

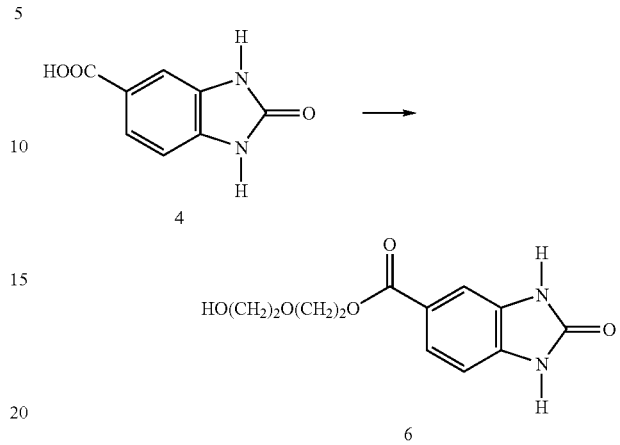

Benzimidazol-2-one-5-carboxylic acid (4) (300 mg, 1.6853 mmol) and Dowex 50 W-X8(H⁺) resin (300 mg) were suspended in diethylene glycol (50 mL) and the mixture heated to reflux for 44 hours. The solid was filtered off and washed with methanol (3×20 mL) and the combined filtrates reduced in volume (approx 2 mL) with vacuum distillation. This residue was column chromatographed ($SiO_2$, isocratically with 4:1 $CHCl_3$:MeOH) to give with evaporated to dryness to give 5[2(1-oxy-2-hydroxyethyl)ethyl]benzimidazol-2-one-5-carboxylate (6) (310 mg, 43% yield) as an off-white powder, $R_f$: 0.63 (4:1 $CHCl_3$:MeOH), mp: 227-228° C., $^1$H NMR ($CDCl_3$/$CD_3OD$): δ 0.88-0.92 (pseudo t, 3H, $CH_3$), 1.33-1.43 (m, 4H, 2×$CH_2$), 1.70-1.79 (m, 2H, $CH_2$), 4.25-4.29 (pseudo t, 2H, $CH_2$), 7.04 (d, 1H, $J_{7,6}$ 8.4 Hz, H-7), 7.44 (bs, 1H, NH), 7.55 (bs, 1H, NH), 7.66 (bs, 1H, H-4), 7.75 (dd, 1H, $J_{6,5}$ 1.5 Hz, H-6);

LRESI negative ion mass spectrum: m/z 247 (100%, [M−H]⁻);

Example 5 benzimidazol-2-one-5-methanoate

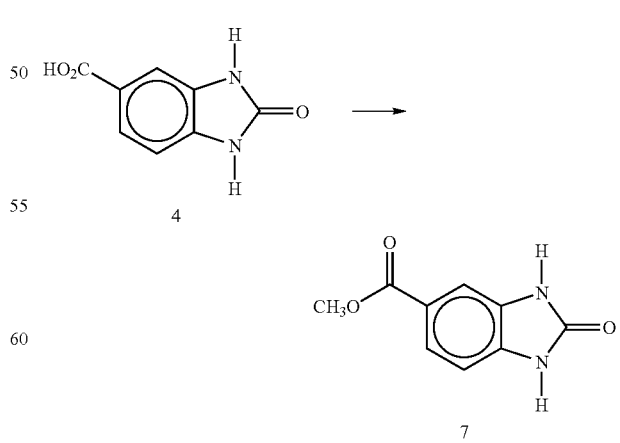

Benzimidazol-2-one-5-carboxylic acid (4) (100 mg; 0.56 mmol) and DCC (100 mg) were suspended in methanol and the mixture heated to reflux for 42 hours. The solid was filtered off and washed with methanol (3×3 mL) and the combined filtrates evaporated to dryness to give benzimidazol-2-one-5-methanoate (7) in 61% yield.

¹HMR (d$_6$-DMSO): δ 3.80 (s, 3H, CO$_2$CH$_3$), 6.70 (d, 1H, J$_{ortho}$ 8.1 Hz, aromatic), 7.46 (bs, 1H, 4-H aromatic), 7.61 (d, 1H, J$_{ortho}$ 8.1 Hz, aromatic), 10.82 (bs, 1H, NH) and 10.99 (bs, 1H, NH).

Negative ion mass spectrum: m/z 191 (40%, M−1$^+$).

Example 6 benzimidazol-2-one-5-ethanoate

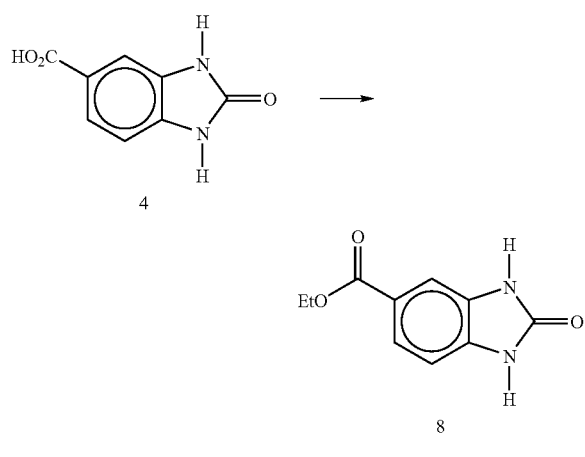

Benzimidazol-2-one-5-carboxylic acid (4) (100 mg) and conc. H$_2$SO$_4$ (0.25 mL) were suspended in ethanol and the mixture heated to reflux for 20 hours. The solid was filtered off and washed with ethanol (50 mL) and the combined filtrates evaporated to dryness to give benzimidazol-2-one-5-ethanoate (8) in 69% yield.

¹HMR (d$_6$-DMSO): δ 1.20 (t, 3H, J=6.9 Hz, CH$_3$—), 4.26 (q. 2H, J=6.9 Hz, OCH$_2$—), 7.00 (d, 1H, J$_{ortho}$ 8.1 Hz, H-7 aromatic), 7.46 (d, 1H, J$_{meta}$ 1.5 Hz, 4-H aromatic), 7.62 (dd, 1H, J$_{ortho}$ 8.2 Hz and J$_{meta}$ 1.5 Hz, 6-H aromatic) and 10.88 (bs, 2H, NH).

Negative ion mass spectrum: M/Z 205 (100%, M−1$^+$).

Example 7 methyl 3-hydroxy-2-{[(2-oxo-2,3-dihydro-1H-1,3-benzimidazol-5-yl)carbonyl]amino}propanoate (9)

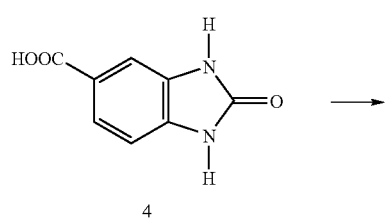

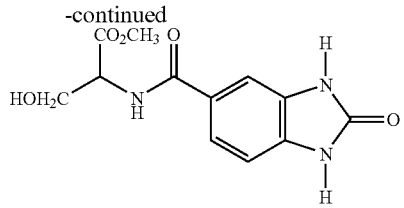

A suspension of benzimidazol-2-one-5-carboxylic acid (4) (356 mg, 2.00 mmol) and L-serine-methylester hydrochloride (311 mg, 2.00 mmol) in sieve dried DMF (6 mL) was cooled in an ice-bath. Then added, in the following sequence, were 1-hydroxybenzotriazole monohydrate (612 mg, 4.00 mmol), diisopropylethylamine (0.696 mL, 517 mg, 4.00 mmol, Hunnig's Base) and 1,3-dicyclohexylcarbodiimide (412 mg, 2.00 mmol). The reaction was allowed to equilibrate to room temperature and left to stir for 41 hours.

The white solid dicyclohexylurea was then filtered off and washed with further DMF (5 mL). The combined filtrates were then vacuum distilled to give a black oil (2.09 g). This was triturated with chloroform (20 mL) over ice to give a dark solid that was filtered off. A sample (250 mg) was made up as a DMF bolus and this column chromatographed (SiO2, isocratically eluted with 4:1 CHCl$_3$:MeOH) to give 208 mg of the benzimidazol-2-one-5-Serine-amido-coupled adduct (9) as a pale brown powder;

R$_f$: 0.41 (4:1 CHCl$_3$:MeOH),

¹H NMR (d$_6$-DMSO): δ 3.63 (s, 3H, CO$_2$CH$_3$), 3.75-3.79 (pseudo t, 2H, CH$_2$), 4.48-4.54 (m, 1H, CH), 5.00 (t, 1H, OH), 6.97 (d, 1H, J$_{7,6}$ 8.1 Hz, H-7), 7.47 (bs, 1H, H-4), 7.54 (dd, 1H, J$_{6,5}$ 1.5 Hz, H-6), 8.35 (d, 1H, J$_{NH}$ 7.5 Hz, NH), 10.83 (bs, 2H, 2×NH);

LRESI mass spectrum: m/z 280 (100%, MH$^+$).

Example 8

3-hydroxy-2-{[(2-oxo-2,3-dihydro-1H-1,3-benzimidazol-5-yl)carbonyl]amino}propanoic acid (10)

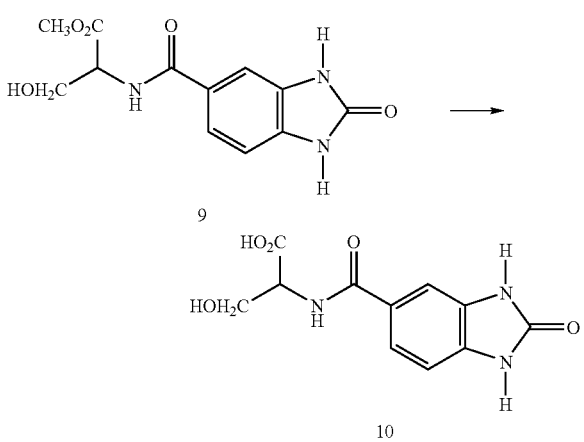

The methyl ester adduct benzimidazol-2-one-5-carboxy-(L-serine)-amide (9) (100 mg, 0.3584 mmol) was suspended in methanol (10 mL) and on addition of 1M aq NaOH (0.68 mL, 0.680 mmol) readily dissolved. The disappearance of starting material was monitored with TLC and complete after stirring overnight at room temperature. The volume was increased by addition of further methanol (30 mL) and the pH carefully adjusted from 10 to 5 by the addition of Dowex 50 W-X8(H$^+$) resin. The resin was rapidly filtered off and washed with further methanol (4×20 mL) and the combined filtrates rotary evaporated to dryness to give benzimidazol-2-one-5-carboxy-(L-serine)-amide (10) (91 mg, 96% yield) as a white powder;

R$_f$: ≦0.04 (4:1 CHCl$_3$:MeOH), $^1$H NMR (d$_6$-DMSO): δ 3.74-3.80 (m, 2H, CH$_2$), 4.38-4.45 (m, 1H, CH), 6.97 (d, 1H, J$_{7,6}$ 8.1 Hz, H-7), 7.46 (bs, 1H, H-4), 7.53 (dd, 1H, J$_{6,5}$ 1.5 Hz, H-6), 8.16 (d, 1H, J$_{NH}$ 7.5 Hz, NH);

LRESI mass spectrum: positive ion m/z 266 (100%, MH$^+$), negative ion m/z 264 (100%, [M−H]$^−$).

Example 9 methyl 2-{[(2-oxo-2,3-dihydro-1H-1,3-benzimidazol-5-yl)carbonyl]amino}-3-phenyl propanoate (11)

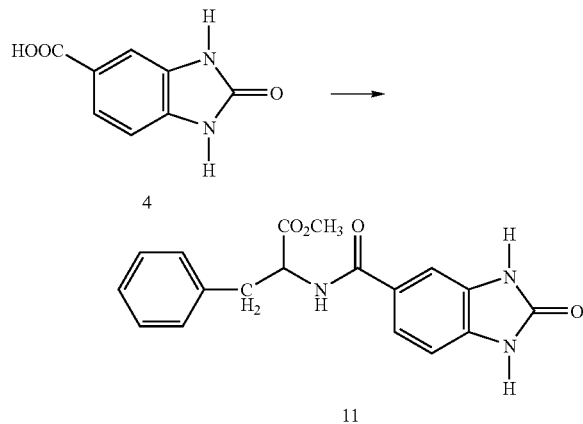

A suspension of benzimidazol-2-one-5-carboxylic acid (4) (356 mg, 2.00 mmol) and L-phenylalanine-methylester hydrochloride (431 mg, 2.00 mmol) in sieve dried DMF (6 mL) was cooled in an ice-bath. Then added, in the following sequence, were 1-hydroxybenzotriazole monohydrate (612 mg, 4.00 mmol), diisopropylethylamine (0.696 mL, 517 mg, 4.00 mmol, Hunnig's Base) and 1,3-dicyclohexylcarbodiimide (412 mg, 2.00 mmol). The reaction was allowed to equilibrate to room temperature and left to stir for 44 hours.

The white solid dicyclohexylurea was then filtered off and washed with further DMF (5 mL). The combined filtrates were then vacuum distilled to give a black oil (2.00 g). This was column chromatographed (SiO$_2$, isocratically eluted with 6:1 CHCl$_3$:MeOH) to give as main product 1.15 g of a brown solid. 150 mg was taken and this then rechromatographed (SiO$_2$, isocratically eluted with 9:1 CHCl$_3$:MeOH) to give 81 mg (equivalent to 90% overall yield) of the benzimidazol-2-one-5-phenylalanine-amido-coupled adduct (11) as an off white powder;

R$_f$: 0.38 (9:1 CHCl$_3$:MeOH), mp: 220-221° C.;

$^1$H NMR (CDCl$_3$/CD$_3$OD): δ 3.06-3.13 (m, 2H, CH$_2$), 3.63 (s, 3H, CO$_2$CH$_3$), 4.86 (pseudo t, 1H, CH), 6.90 (bd, 1H, J 8.1 Hz), 7.03-7.05 (m, 2H), 7.10-7.18 (m, 3H), 7.28-7.31 (m, 2H, J 8.1 Hz, J=1.5 Hz);

LRESI mass spectrum: m/z 340 (41%, MH$^+$), 225 (100%).

Example 10

2-{[(2-oxo-2,3-dihydro-1H-1,3-benzimidazol-5-yl)carbonyl]amino}-3-phenyl propanoic acid (12)

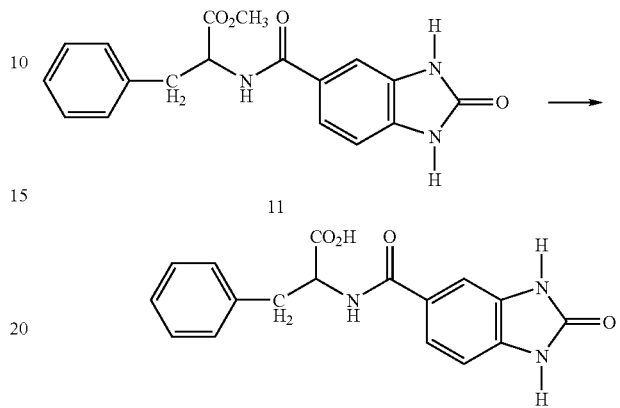

1M aq NaOH (0.75 mL, 0.75 mmol) was added to the methyl ester adduct of benzimidazol-2-one-5-carboxy-(L-phenylalanine)-amide (11) (65 mg, 0.1917 mmol) dissolved in methanol (7.5 mL) and this stirred overnight at room temperature. The volume was increased then increased to 50 mL by the addition of further methanol and the pH then carefully adjusted from 10 to 5 by the addition of Dowex 50 W-X8(H$^+$) resin. The resin was rapidly filtered off, washed with further methanol (4×20 mL) and the combined filtrates rotary evaporated to dryness to give an oil. This was taken up in hot ethanol and on cooling a white solid settled out from solution. This was filtered off and dried to give benzimidazol-2-one-5-carbox-(L-phenylalanine)-amide (12) (60 mg, 97% yield) as a white powder;

R$_f$: ≦0.03 (9:1 CHCl$_3$:MeOH), mp: 222-223° C., $^1$H NMR (CD$_3$OD): δ 3.13 (dd, 1H, J$_{germinal}$ 13.5 Hz, J 7.8 Hz, benzyl-CH$_2$), 3.34 (dd, 1H, benzyl-CH$_2$), 4.76 (pseudo t, 1H, J 7.5 Hz, CH), 7.03 (bd, 1H, J 8.1 Hz), 7.12-7.27 (m, 5H), 7.43-7.47 (m, 2H, J 8.4 Hz, J 1.5 Hz);

LRESI mass spectrum: m/z 326 (100%, MH$^+$).

Example 11

N-(3,4-dihydroxyphenethyl)-2-oxo-2,3-dihydro-1H-1,3-benzimidazole-5-carboxamide (13)

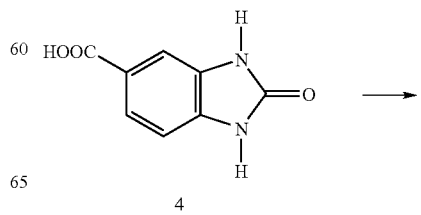

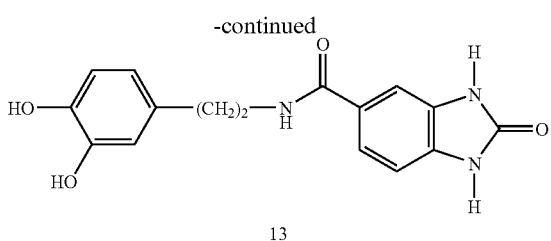

13

A suspension of benzimidazol-2-one-5-carboxylic acid (4) (356 mg, 2.00 mmol) and 3,4-dihydroxyphenylethylamine hydrochloride (379 mg, 2.00 mmol) in sieve dried DMF (6 mL) was cooled in an ice-bath. Then added, in the following sequence, were 1-hydroxybenzotriazole monohydrate (612 mg, 4.00 mmol), diisopropylethylamine (0.696 mL, 517 mg, 4.00 mmol, Hunnig's Base) and 1,3-dicyclohexylcarbodiimide (412 mg, 2.00 mmol). The reaction was allowed to equilibrate to room temperature and left to stir for 44 hours.

The white solid dicyclohexylurea was then filtered off and washed with further DMF (2×5 mL). The combined filtrates were then vacuum distilled to give a dark brown oil (2.39 g). This was taken up in methanol (5 mL) and on addition of chloroform (10 mL) a dark solid settled out off solution. This was filtered off, dissolved in a minimum amount of DMF and then subject to column chromatography (SiO$_2$, isocratically eluted with 4:1 CHCl$_3$:MeOH) to give 604 mg (96% yield) of benzimidazol-2-one-5-dopamine-amido-coupled adduct (13) as a pale brown powder. A sample was triturated with cold 4:1 CHCl$_3$:MeOH, filtered and dried to give material for spectroscopic and bioassay analysis.

R$_f$: 0.38 (9:1 CHCl$_3$:MeOH), mp: >250° C., darkens without melting;

$^1$H NMR (d$_6$ DMSO): δ 2.49 (t, 2H, J 1.8 Hz. CH$_2$), 2.62 (t, 2H, J 78 Hz. CH$_2$), 6.45 (dd, 1H, J$_{6',5'}$ 8.1, J$_{6',2'}$ 1.8 Hz, H-6') 6.60-6.64 (m, 2H, H-2', H-5'), 6.94 (d, 1H, J$_{7,6}$ 8.4 Hz, H-7), 7.42 (bs, 1H, H-4), 7.47 (dd, 1H, J$_{6,4}$ 1.5 Hz, H-4), 8.33 (bt, 1H, J 5.4 Hz, amide NH), 8.63 (bs, 1H, hetero NH), 8.73 (bs, 1H, hetero NH);

LRESI mass spectrum: m/z, negative ion 312 (63%, [M–H]$^-$), (249, 39%), (134, 100%); positive ion 314 (37%, MH$^+$), (211, 69%), (130, 100%).

Example 12 benzimidazol-2-thio-5-carboxylic acid (14)

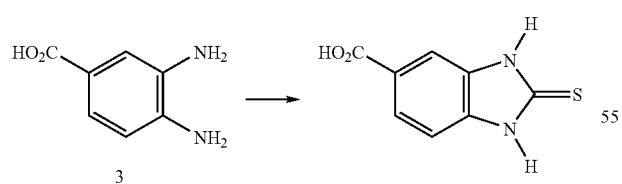

The method described by Harvey et al. (12) and used in Example 2 for the preparation of benzimidazol-2-one-5-carboxylic acid (4) was used except this preparation used thiourea instead of urea.

Thiourea (1.52 g, 2 mmol) and 3,4-diaminobenzoic acid (3) (3.04 g, 2 mmol) in pentan-1-ol (14 ml) was stirred vigorously and heated to reflux under nitrogen atmosphere. Heating was discontinued after 5 hours, and stirring continued for 12 hours. Water was added and the pH adjusted to 1. The solvents were removed and the black solid was triturated with cold water (10 ml) and filtered to give 1.94 g of a black powder.

LRESI negative ion in mass spectrum: m/z 193 (M–H$^-$).

Example 13

Pentyl-benzimidazole-2-thioxo-5-carboxylate (15)

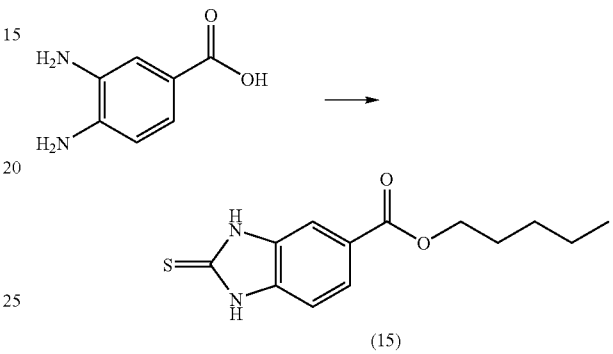

To a mixture of the diamine (500 mg, 3.28 mmol) in anhydrous 1-pentanol (50 mL) was added thiourea (300 mg, 3.94 mmol). The mixture was refluxed for 6 hrs, and then cooled before filtering to furnish a black solid (471 mg, 74%). The solid was washed with 1M HCl and water. The dried solid (200 mg) was then suspended in anhydrous 1-pentanol (25 ml), to which was added Dowex H$^+$ resin (200 mg). The mixture was refluxed for 42 hrs. The reaction mixture was cooled and filtered, and the filtrate concentrated to furnish the title compound as a black gum (193 mg, 52% overall yield).

$^1$H NMR (CDCl$_3$): δ 8.41 (s, 1H, ArH), 8.03 (d, 1H, ArH), 7.82 (d, 1H, ArH), 4.30 (t, 2H, —OCH$_2$CH$_2$CH$_2$CH$_2$CH$_3$), 1.75 (m, 1H, —OCH$_2$CH$_2$CH$_2$CH$_2$CH$_3$), 1.38 (m, 4H, —OCH$_2$CH$_2$CH$_2$CH$_2$CH$_3$), 0.89 (m, 3H, —OCH$_2$CH$_2$CH$_2$CH$_2$CH$_3$);

LRMS (ESI): m/z 265 [M+H$^+$];

C$_{13}$H$_{16}$N$_2$O$_2$S: 264.34

Example 14

3,4,5-tris(acetyloxy)-6-[(acetyloxy)methyl]tetrahydro-2H-pyran-2-yl-benzimidazole-2-one-5-carboxylate (16)

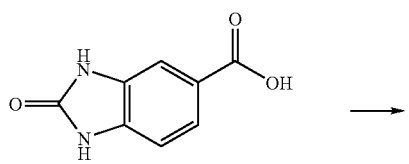

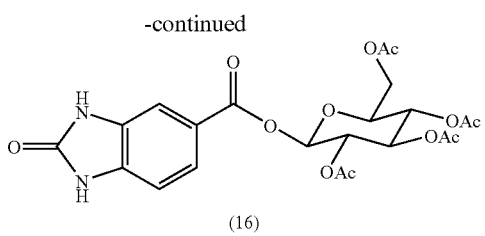

(16)

To a solution of the acid (128 mg, 0.72 mmol) in anhydrous pyridine (20 mL) was added Ag$_2$CO$_3$ (265 mg, 0.96 mmol), and molecular sieves (4 Å, 2.7 g). The mixture was stirred under an atmosphere of nitrogen at room temperature for 30 minutes. Tetra-O-acetyl-glucopyranosyl bromide (100 mg, 0.24 mmol) was added to the reaction mixture, and stirred overnight at room temperature. The mixture was then filtered through celite and the filtrate concentrated to an amber gum. The gum was dissolved in chloroform (5 mL), and triturated with ether to furnish the title compound as a white solid (19 mg, 15%).

$^1$H NMR (CDCl$_3$): δ 8.70, 8.60 (2×bs, 2×1H, 2×NH), 7.80 (d, 1H, ArH), 7.70 (s, 1H, ArH), 7.10 (s, 1H, ArH), 5.92 (d, 1H, H-1, J$_{1,2}$ 3.8 Hz), 5.36 (m, 2H, H-3+H-2), 5.23 (m, 1H, H-4), 4.33 (dd, 1H, H-6, J$_{gem}$ 11.7 Hz, J$_{vic}$ 4.6 Hz), 4.15 (d, 1H, H-6', J$_{gem}$ 11.8 Hz), 3.96 (m, 1H, H-5), 2.07, 2.05, 2.0, 1.59 (4×s, 4×3H, 4×OAc);

LRMS (ESI): m/z 526 [M+NH$_4^+$];

C$_{22}$H$_{24}$N$_2$O$_{12}$: 508.43

Example 15

5-Bromo-6-methybenzimidazol-2-one (17)

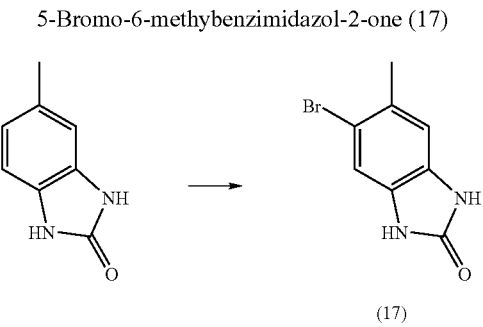

(17)

A mixture of 6-methyl-1,3-dihydro-benzoimidazol-2-one (1.00 g, 6.76 mmol) as prepared in Example 1, N-bromosuccinimide (1.30 g, 7.30 mmol) and 3-chloroperoxybenzoic acid (0.05 g, 0.29 mmol) in carbon tetrachloride (15 ml) was heated under reflux for 4 h. When cooled to room temperature, the mixture was filtered and the solid was recrystallised from methanol to give (17) as a beige solid (0.80 g). Furthermore, the solid insoluble in methanol was collected to give more (17) (0.50 g) and the solids were combined (1.30 g, 85%).

$^1$H NMR (d$_6$-DMSO): δ 2.29 (s, 3H, CH$_3$), 6.89 (s, 1H, ArH), 7.06 (s, 1H, ArH), 10.59 (s, 1H, NH), 10.67 (s, 1H, NH).

$^{13}$C NMR (d$_6$-DMSO): δ 22.9 (CH$_3$), 111.0 (CH), 112.0 (CH), 114.8 (C), 128.9 (C), 129.7 (C), 130.0 (C), 155.7 (C).

ESMS: m/z 225.0 (M−1).

Example 16

5-Hydroxy-6-methybenzimidazol-2-one (18)

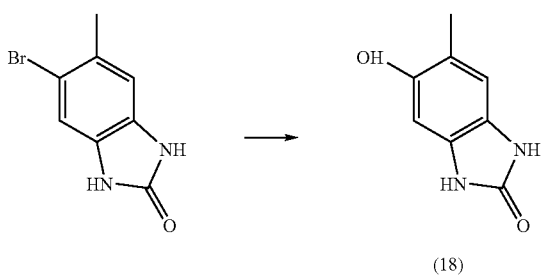

(18)

A solution of (16) (0.30 g, 1.32 mmol) in 10% sodium hydroxide (5 ml) and ethanol (5 ml) was heated under reflux for 1.5 h. When cooled to room temperature the ethanol was removed in vacuo and the mixture was filtered to give (18) as a white solid (0.20 g, 92%).

$^1$H NMR (d$_6$-DMSO): δ 2.28 (s, 3H, CH$_3$), 6.88 (s, 1H, ArH), 7.05 (s, 1H, ArH), 10.61 (s, 1H, NH), 10.66 (s, 1H, NH).

Example 17

5-Dodecanylbenzoimidazol-2-one (19)

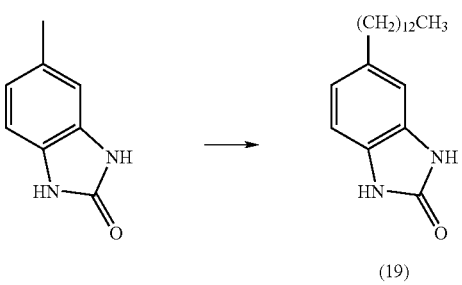

(19)

Sodium (0.05 g, 2.17 mg atom) was dissolved in ethanol (5 ml) and to this was added 6-methyl-1,3-dihydro-benzoimidazol-2-one (0.20 g, 1.35 mmol) and the solution was stirred at room temperature for 1 h. The solvent was removed in vacuo and the white solid was taken up in tetrahydrofuran (5 ml) and dimethyl sulfoxide (5 ml), and to this was added 1-bromododecane (0.34 g, 1.36 mmol) and the whole was stirred at room temperature for 2 h. N,N-Dimethylformamide (5 ml) was added to the mixture and the whole was stirred for a further 2 h. The mixture was filtered and the filtrate was evaporated in vacuo to give a yellow residue. The residue was placed on a silica column and chromatographed with 12.5% hexane-ethyl acetate to give (19) as a yellow oil.

$^1$H NMR (d$_6$-DMSO): δ 0.84 (t, 3H, J=4.5 Hz, CH$_3$), 1.20 (s, 18H, 9CH$_2$), 1.32-1.37 (m, 2H, CH$_2$), 1.74-1.79 (m, 2H, CH$_2$), 3.49 (t, 2H, J=6.6 Hz, CH$_2$), 6.71-6.76 (m, 3H, 3ArH), 10.45 (bs, 2H, 2NH).

ESMS: m/z 317.3 (M+1).

Example 18

4,5,7-Tribromo-6-methylbenzimidazol-2-one (20)

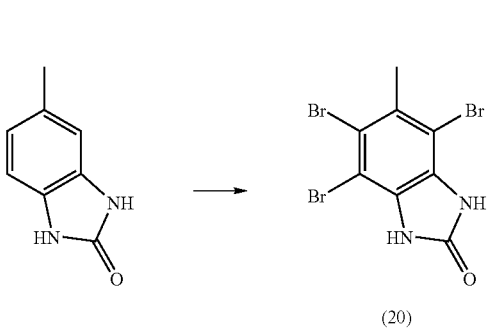

(20)

A mixture of 6-methyl-1,3-dihydro-benzoimidazol-2-one (0.50 g, 3.38 mmol), sodium acetate (1.70 g, 20.48 mmol) in acetic acid (4 ml) was heated at 70° C. A solution of bromine (1.60 g, 10.0 mmol) in acetic acid (5 ml) was slowly added over 10 min. The mixture was then heated under reflux for 1 h. When cooled to room temperature, the yellow mixture was poured into ice-cold water (100 ml) and filtered. The solid was recrystallised from ethanol to give (20) as a beige solid (0.76 g, 58%).

$^1$H NMR ($d_6$-DMSO): δ 2.56 (s, 3H, CH$_3$), 11.33 (s, 2H, 2NH).

$^{13}$C NMR ($d_6$-DMSO): 30.8 (CH$_3$), 102.7 (C), 103.4 (C), 117.0 (C), 129.2 (CBr), 129.3 (CBr), 129.6 (CBr), 154.6 (C).

Example 19

4,5,6,7-Tetrabromobenzimidazol-2-one (21)

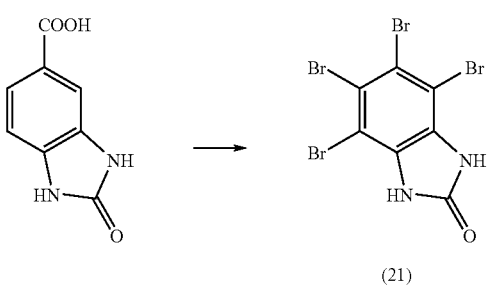

(21)

A mixture of 2-oxo-2,3-dihydro-1H-benzoimidazole-5-carboxylic acid (0.3 g, 1.7 mmol), sodium acetate (0.83 g, 10.0 mmol) in acetic acid (3 ml) was heated at 70° C. A solution of bromine (0.80 g, 5.0 mmol) in acetic acid (3 ml) was slowly added over 10 min. The mixture was then heated under reflux for 1 h. When cooled to room temperature, the yellow mixture was poured into ice-cold water (100 ml) and filtered. The solid was recrystallised from ethanol to give (21) as a golden-like solid (0.25 g, 33%).

$^1$H NMR ($d_6$-DMSO): δ 11.59 (s, 1H, COOH).

ESMS: m/z 444.8 (25%) (M−1), 446.9 (70%), 448.9 (100%), 450.9 (70%), 452.9 (15%).

Example 20

5-Methyl-6-nitrobenzimidazol-2-one (22)

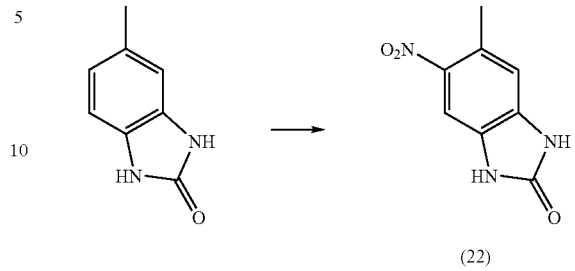

(22)

A mixture of 6-methyl-1,3-dihydro-benzoimidazol-2-one (0.30 g, 2.03 mmol) in 69% nitric acid (5 ml) was stirred over ice for 2 h. The yellow mixture was filtered and washed with water to give (22) as a bright yellow solid (0.39 g, 99.7%).

$^1$H NMR ($d_6$-DMSO): δ 2.53 (s, 3H, CH$_3$), 6.94 (s, 1H, ArH), 7.57 (s, 1H, ArH), 10.96 (s, 1H, NH), 11.20 (s, 1H, NH).

Example 21

5-Amino-6-methylbenzimidazol-2-one (23)

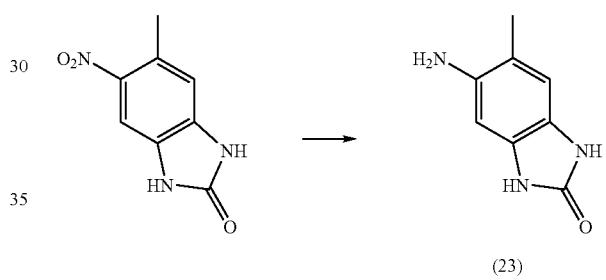

(23)

A mixture of (22) (0.25 g, 1.30 mmol) and 10% palladium on carbon (0.05 g) in ethanol (15 ml) was hydrogenated at atmospheric pressure for 4 h. The catalyst was filtered off through Celite, and the solvent was removed in vacuo to give (23) as a white solid.

$^1$H NMR ($d_6$-DMSO): δ 2.01 (s, 3H, CH$_3$), 4.40 (s, 2H, NH$_2$), 6.29 (s, 1H, ArH), 6.50 (s, 1H, ArH), 9.96 (s, 1H, NH), 10.08 (s, 1H, NH).

ESMS: m/z 164.0 (M+1).

Example 22

N-(6-Methylbenzimidazol-5-yl)-2-pyrimidin-2-yl-sulfanyl)-acetamide (24)

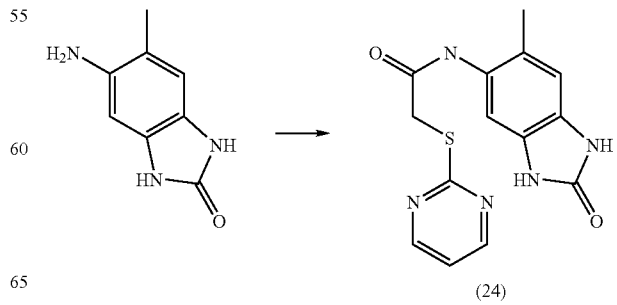

(24)

A solution of (2-pyrimidylthio)acetic acid (0.14 g, 0.82 mmol) and 1,1'-carbonyldiimidazole (0.24 g, 1.48 mmol) in dioxan (5 ml) was heated under reflux for 1 h. The solution was cooled, (23) (0.10 g, 0.61 mmol) was added, and the mixture was heated under reflux for 2 h. When cooled to room temperature, the mixture was filtered and the filtrate was evaporated in vacuo. The residue was taken up in 10% potassium hydroxide (20 ml) and the mixture was filtered to give a dark brown solid. This was recrystallised from acetonitrile to give (24) as a brown solid.

$^1$H NMR (d$_6$-DMSO): δ 2.20 (s, 3H, CH$_3$), 3.29 (s, 2H, CH$_2$), 6.71 (s, 1H, ArH), 7.30 (s, 1H, ArH), 7.93 (s, 1H, ArH), 8.56-8.65 (m, 2H, 2ArH), 10.33 (s, 1H, NH), 10.35 (s, 1H, NH).

ESMS: m/z 314.2 (M−1).

Example 23

Pentyl-benzimidazol-2-one-5-carbothioate (25)

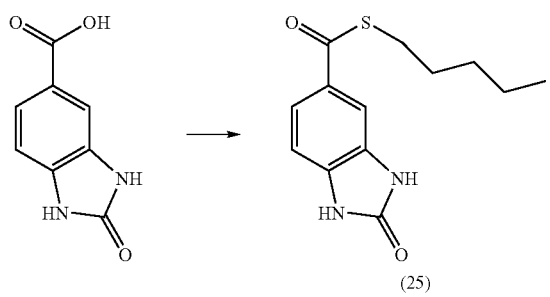

2-Oxo-2,3-dihydro-1H-benzoimidazole-5-carboxylic acid (0.20 g, 1.12 mmol) in thionyl chloride (5 ml) was heated under reflux for 30 min. The excess of thionyl chloride was removed in vacuo and the residue was taken up in pyridine (5 ml). 1-Pentathiol (0.23 g, 2.21 mmol) was added and the whole was placed at reflux for 2 h. When cooled to room temperature, the mixture was filtered, and the filtrate was evaporated in vacuo. The residue was taken up in 10% potassium hydroxide and extracted with ethyl acetate, dried over sodium sulfate, and the solvent was removed in vacuo to give (25) as a white solid.

$^1$H NMR (d$_6$-DMSO): δ 0.86 (t, 3H, J=6.9 Hz, CH$_3$), 1.31 (m, 4H, 2CH$_2$), 1.60 (m, 2H, CH$_2$), 2.99 (t, 2H, J=7.2 Hz, CH$_2$), 7.00 (d, 1H, J=8.1 Hz, ArH), 7.40 (s, 1H, H-4), 7.61 (s, 1H, J=8.4 Hz, ArH).

Example 24

5-(benzimidazol-2(3H)-one-6-yl)-5-oxopentanoic acid (26)

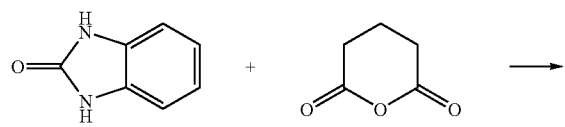

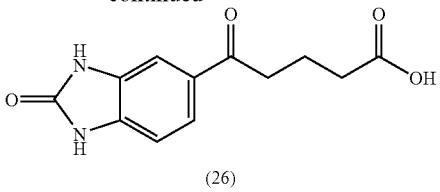

The procedure of Kosyakovskaya (17) was followed.

To a suspension of glutaric anhydride (3.42 g, 30 mmol) and benzimidazol-2(3H)-one (4.02 g, 30 mmol) in tetrachloroethane (100 ml), was added aluminium chloride from a freshly opened container (14.0 g, 105 mmol) in small portions. This mixture was heated to 120 C for 105 min, cooled to room temperature, then poured onto a mixture of ice (75 g) and concentrated hydrochloric acid (20 ml). The suspension was stirred overnight to break up solids that had formed. The tetrachloroethane was azeotropically distilled from the mixture with water under reduced pressure, leaving a brown solid suspended in an aqueous phase. The solid was filtered off and washed with dilute aqueous hydrochloric acid, then water. The solid was added to boiling aqueous sodium carbonate (5% w/v, 150 ml) and the solution filtered. Decolourizing charcoal was added to the cooled filtrate, which was then boiled for 5 min. The charcoal was removed by filtration, and the filtrate treated with concentrated hydrochloric acid until the pH of the solution was 4. The precipitated solid was allowed to stir overnight, filtered off, and dried in a vacuum oven at 50 C/20 mmHg until a constant weight was achieved (1.6 g of brown solid). Nmr indicates that some starting material still remains. Recrystallization of a portion of this solid from acetic acid, as indicated by Kosyakovskaya, did not afford recovery of any product. A portion of the brown solid (300 mg) was dissolved in aqueous sodium bicarbonate (5% w/v, 10 ml) and insoluble material removed by filtration. The filtrate was acidified with concentrated hydrochloric acid and the precipitate formed filtered off and dried at the pump (30 mg).

m/z (EI) found 248.0799, expected 248.0797 (C$_{12}$H$_{12}$N$_2$O$_4$) 248.0797;

$^1$H-nmr (200 MHz, d$_6$-DMSO) δ 11.05 (brs, 1H), 10.89 (brs, 1H), 7.66 (dd, 1H), 7.47 (d, 1H), 7.00 (d, 1H), 3.00 (t, 21), 2.29 (t, 2H), 1.81 (p, 2H).

Example 25

2(3H)-benzimidazolone-5-sulfonic acid pentyl amide (27)

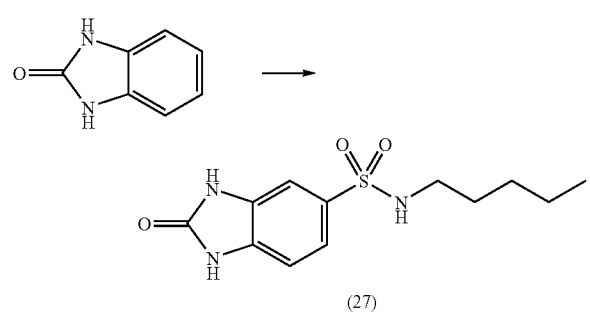

Chlorosulfonic acid (5 ml) was cooled to −5 C and 2(3H)-benzimidazolone (1 g) was added portionwise with stirring. The cooling bath was removed and the reaction allowed to warm to room temperature over 30 min, followed by heating to 95 C for an additional 30 min. After cooling to room temperature 2 ml of the reaction solution was added to n-pentylamine (10 ml) in ice (20 g). Precipitation occurred and the suspension was allowed to stand over night. Filtration followed by extensive rinsing with water gave 760 mg of silvery-grey platelets. A small amount was recrystallised from methanol to give nearly colourless crystals of the title compound.

Mp 316-318 C;

m/z (EI) found 283.0992, expected ($C_{12}H_{17}N_3O_3S$) 283.0991; $^1$H-nmr (500 MHz, $d_6$-DMSO) δ 11.01 (bs, 2H), 7.38 (dd, 1H), 7.34 (bt, 1H), 7.28 (d, 1H), 7.04 (d, 1H), 2.64 (m, 2H), 1.35-1.29 (m, 2H), 1.17-1.14 (m, 4H), 0.78 (t, 3H);

$^{13}$C-nmr (125.8 MHz, $d_6$-DMSO) δ 155.35, 132.83, 132.35, 129.63, 119.91, 108.13, 106.59, 42.47, 28.53, 28.21, 21.61, 13.76.

Example 26

2(3H)-benzimidazolone-
5-sulfonic acid pentyl ester (28)

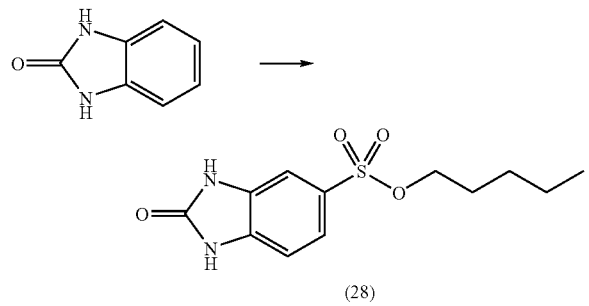

(28)

Similarly, a sample of the reaction mixture from Example 25 was quenched with n-pentanol instead of n-pentylamine. Chromatography using methanol resulted in partial decomposition of the sample, and recovered the title compound as a colourless solid (2.1 mg);

m/z (EI) found 284.0829, expected ($C_{12}H_{16}N_2O_4S$) 284.0831;

$^1$H-nmr (200 MHz, $d_6$-DMSO) δ 11.03 (bs, 2H), 7.38 (dd, 1H), 7.29 (d, 1H), 7.06 (d, 1H), 2.65 (m, 2H), 1.40-1.22 (m, 2H), 1.22-1.06 (m, 4H), 0.78 (t, 3H);

$^{13}$C-nmr (50.3 MHz, $d_6$-DMSO) 155.27, 132.75, 132.27, 129.56, 119.856, 108.07, 106.53, 70.88, 70.82, 42.41, 28.46, 28.14, 21.54, 13.70.

Example 27

Ethyl 4-amino-3-nitrobenzenecarboximidoate (29)

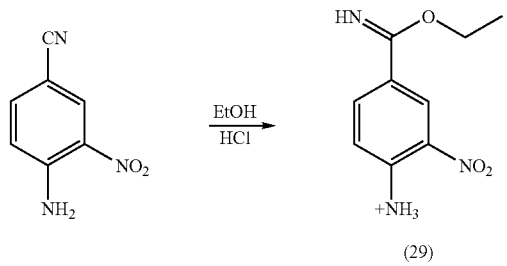

(29)

Synthesis of the nitrile to amidine was prepared according to the Pinner reaction (18). 4-Aminobenzonitrile (0.5 g, 3.1 mmol) was dissolved in 30 ml of dry ethanol and cooled in an ice/water bath. The solution was saturated with dry HCl and kept at a maximum temperature of 20° C. After 1 hr of saturation the solution was allowed to stir at room temperature overnight. The resulting precipitate was collected and filtered to give the title product 0.55 g (86%) as a yellow powder which was pure enough to be used in the following reaction without further purification.

$^1$H NMR (DMSO) δ 1.46 (t, J 6.9 Hz, 3H, $CH_3$), 4.59 (q, J 6.9 Hz, 2H, O—$CH_2$), 7.17 (d, J 9.3 Hz, 1H, Ar—H), 8.09 (dd, J 2.1, 9.0 Hz, 1H, Ar—H) 8.81 (d, J 2.1 Hz, 1H, Ar—H).

Example 28

3-amino-N-butyl-
3-nitrobenzenecarboximidamide (30)

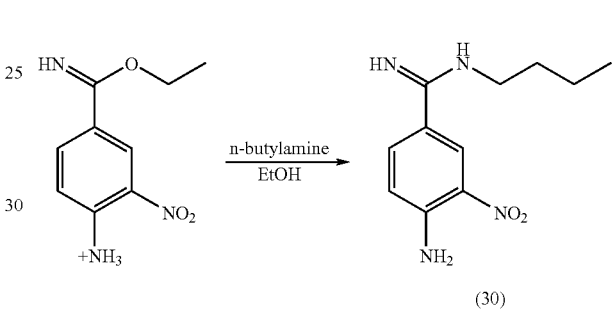

(30)

n-Butylamine (0.292 g, 4.0 mmol) was distilled prior to use and was added to a stirred suspension of Ethyl 4-amino-3-nitrobenzenecarboximidoate (0.7 g, 3.3 mmol) in 15 ml of dry ethanol. The mixture was stirred for 12 hrs at room temperature and then a further hour at 50° C. The resulting dark yellow precipitate was collected by filtration and recrystallised from boiling ethanol yield (89%) as yellow prisms.

$^1$H NMR (DMSO) δ 0.92 (t, J 7.2 Hz, 3H, $CH_3$), 1.38 (m, 2H, $CH_2$), 1.59 (m, 2H, $CH_2$), 3.38 (m, 2H, NH—$CH_2$), 7.16 (d, J 9.0 Hz, 1H, Ar—H), 7.76 (dd, J 1.8, 8.7 Hz, 1H, Ar—H) 8.49 (d, J, 2.1, 1H, Ar—H). m/z (+ESI, 30V) 237.3 ($MH^+$). (19)

Example 29

3,4-diamino-N-butylbenzenecarboximinamine (31)

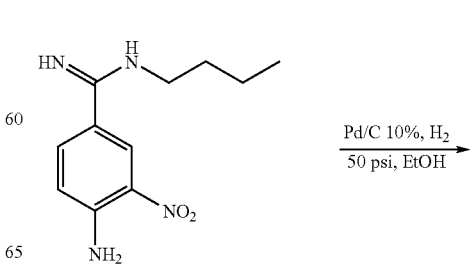

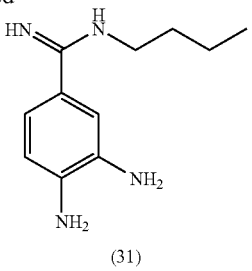

(31)

3-amino-N-butyl-3-nitrobenzenecarboximidamide and 0.125 g of 10% Pd/C in 100 ml of dry methanol was subjected to hydrogenation at 50 psi for approximately 1 h. The catalyst was filtered over Celite and washed with hot methanol. The filtrate was evaporated to give a sticky residue that was triturated with dry ether and dried under vacuum. The product was purified by recrystallising in boiling ethanol to give the title product as a purple powder 0.56 g (97%) mp 150.4° C.

$^1$H NMR (DMSO) δ 0.92 (t, J 7.2 Hz, 3H, CH$_3$), 1.38 (m, 2H, CH$_2$), 1.59 (m, 2H, CH$_2$), 3.35 (m, 2H, NH—CH$_2$), 6.91 (d, J 8.4 Hz, 1H, Ar—H), 7.32 (d, J 8.4 Hz, 1H, Ar—H) 7.43 (s, 1H, Ar—H). m/z (+ESI, 30V) 207.1 (MH$^+$). (19)

Example 30

N-butyl-2-oxo-2,3-dihydro-1H-1,3-benzimidazole-5-carboximidamide (32)

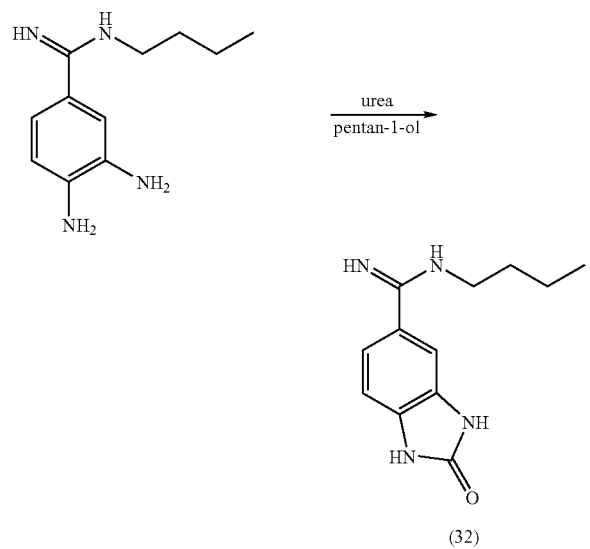

A solution of urea (0.15 g, 2.5 mmol) and 3,4-diamino-N-butylbenzenecarboximinamine (0.4 g, 1.9 mmol) in 10 ml of pentan-1-ol was vigorously stirred and heated to reflux under a nitrogen atmosphere. The heating was discontinued after 2 hours and on cooling to room temperature the solution was filtered. The filtrate was removed under reduced pressure to yield gummy oil which was triturated with dry ether and dried under vacuum to give the title product as a pink powder 0.3 g (66%) mp 168° C. (12)

$^1$H NMR (DMSO) δ 0.92 (t, J 7.2 Hz, 3H, CH$_3$), 1.38 (m, 2H, CH$_2$), 1.59 (m, 2H, CH$_2$), 3.35 (m, 2H, NH—CH$_2$), 7.11 (d, J 8.1 Hz, 1H, Ar—H), 7.31 (s, 1H, Ar—H), 7.37 (d, J 8.4 Hz, 1H, Ar—H). m/z (+ESI, 30V) 233.1 (MH$^+$).

Example 31

5-heptanoylbenzofuran-2(3H)-one (33)

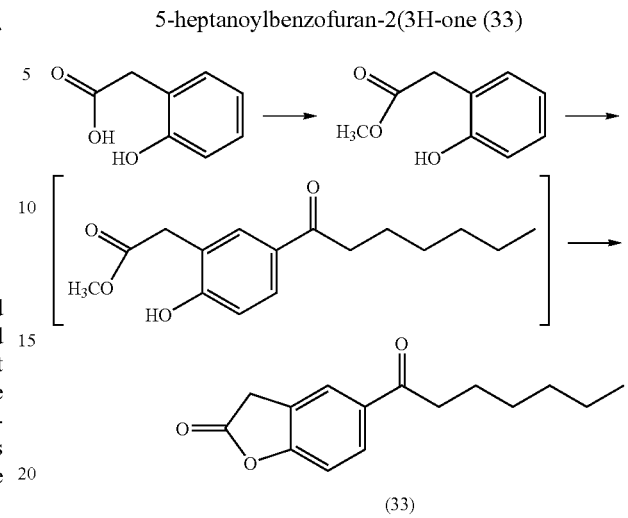

(33)

2-Hydroxyphenylacetic acid was converted to its methyl ester following the procedure in U.S. Pat. No. 4,695,648 (Pharmacia), then to the title compound by a modification of the Friedel-Craft procedure given in the same patent as follows.

To a solution of methyl 2-hydroxyphenylacetic acid methyl ester (1000 mg, 6.02 mmol) in nitrobenzene (10 ml) was added heptanoyl chloride (900 mg, 6.02 mmol), followed by aluminium chloride (1.6 g, 12.0 mmol, 2 equiv). The solution was heated to 60 C for 18 h, then cooled on ice before quenching with aqueous hydrochloric acid (1 M, 50 ml). The mixture was extracted with dichloromethane. (3×50 ml) and concentrated. Chromatography on silica gel using ethyl acetate/petroleum spirits (20:80) as eluant gave a semi-solid yellow residue. Recrystallization from dichloromethane/petroleum spirits at −15 C gave the title compound as a pale yellow solid (129 mg). Mp 64-67° C.;

m/z (EI) found 246.1258, expected (C$_{15}$H$_{18}$O$_3$) 246.1256;

$^1$H-nmr (500 MHz, CDCl$_3$) δ 7.93 (d, 1H), 7.91 (s, 1H), 7.13 (d, 1H), 3.77 (s, 2H), 2.90 (t, 2H), 1.69 (p, 2H), 1.20-1.40 (m, 6H), 0.86 (t, 3H);

$^{13}$C-nmr (125.8 MHz, CDCl$_3$) δ 198.79, 173.10, 157.82, 133.48, 129.85, 124.69, 123.47, 110.46, 38.40, 32.53, 31.54, 28.91, 24.26, 22.42, 13.94.

Example 32

5-Pentylbenzimidazol-2-one (34)

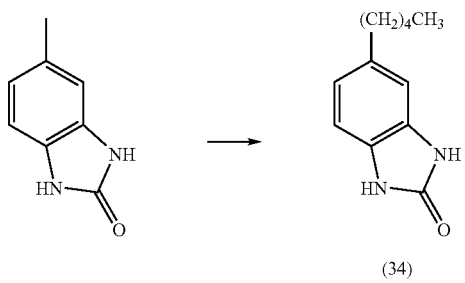

(34)

To a solution of 5-methylbenzimidazol-2-one (50 mg, 3.378×10$^{-4}$ mol) in dry ethanol (5 ml), the freshly made sodium ethoxide in ethanol (1M, 1.01×10$^{-3}$ mol equivalents)

was added dropwise under a nitrogen atmosphere. At room temperature the mixture was stirred for 3 hrs under an atmosphere of nitrogen and the ethanol was then removed under reduced pressure. To this a solution of dry DMSO (3 ml) and 1-bromobutane (54 µl, 5.1×10$^{-4}$ mol) was added and stirred at room temperature under an atmosphere of nitrogen overnight. The reaction mixture was then quenched with ice and neutralised using 1M hydrochloric acid solution, forming a white solid product. The solid was collected by filtration and purified using preparative thin liquid chromatography with 10% MeOH/CHCl$_3$.

$R_f$=0.78

ESMS m/z 205 [(M+1)/1]

Biological Testing

In Vitro Assay of MIF Antagonisms

The activity of compounds was studied in a bioassay utilising MIF-dependent activation of human dermal fibroblasts. Sampey et al (20) have shown that induction of the expression of cyclooxygenase-2 (COX-2) by the cytokine interleukin 1 (IL-1) is dependent upon the presence of MIF, i.e. can be prevented using specific anti-MIF monoclonal antibody. IL-1-induced COX-2 expression is therefore a MIF-dependent event.

S112 human dermal fibroblasts were propagated in RPMI 10% foetal calf serum (FCS). Prior to experimentation, cells were seeded at 10$^5$ cells/ml in RPMI/0.1% BSA for 18 hours. Cells were treated with recombinant human IL-1 (0.1 ng/ml) and with each compound at 1-100 µM. A control was treated only with recombinant human IL-1 (0.1 ng/ml) and vehicle (DMSO). After 6 hours, cells were collected and intracellular COX-2 protein determined by permeabilisation flow cytometry. Cells permeabilised with 0.1% saponin were sequentially labelled with a mouse anti-human COX-2 monoclonal antibody and with sheep-anti-mouse F(ab)2 fragment labelled with fluoroscein isothiocyanate. Cellular fluorescence was determined using a flow cytometer. At least 5000 events were counted for each reading, each of which was performed in duplicate, and the results expressed in mean fluorescence intensity (MFI) after subtraction of negative control-labelled cell fluorescence.

The effect of each compound was determined by subtracting the IL-1+compound-treated cell MFI from the IL-1-treated cell (control) MFI and expressed as % inhibition.

Results are shown in Table 1 below. In each case the % inhibition of IL-1-induced COX-2 expression is expressed as the mean, or mean±SEM where results are available from multiple experiments.

TABLE 1

| Compound | % inhibition | Concentration (µM) | number of expts. |
| --- | --- | --- | --- |
| 5 | 52.2 +/− 2.1% | 100 | 7 |
| 5 | 48.4 +/− 2.7% | 50 | 23 |
| 5 | 34.0 +/− 5.3% | 25 | 6 |
| 5 | 21.4 +/− 2.5% | 10 | 8 |
| 5 | 7.7 +/− 2.0% | 1 | 7 |
| 27 | 37.40% | 50 | 1 |
| 15 | 33.10% | 50 | 1 |
| 13 | 29.9 +/− 4.8% | 100 | 3 |
| 13 | 32.2 +/− 4.7% | 50 | 8 |
| 13 | 14.1 +/− 0.6% | 10 | 3 |
| 13 | 9.6 +/− 3.0% | 1 | 3 |
| 24 | 30.30% | 50 | 1 |
| 22 | 30.00% | 25 | 1 |
| 20 | 28.50% | 25 | 1 |
| 19 | 24.50% | 50 | 1 |
| 19 | 21.30% | 25 | 1 |

TABLE 1-continued

| Compound | % inhibition | Concentration (µM) | number of expts. |
| --- | --- | --- | --- |
| 17 | 22.40% | 50 | 1 |
| 34 | 14.90% | 10 | 1 |
| 8 | 19.9 +/− 3.9% | 50 | 7 |
| 12 | 19.9 +/− 6.2% | 50 | 4 |
| 10 | 19.3 +/− 4.1% | 50 | 2 |
| 6 | 17.8 +/− 3.5% | 50 | 4 |
| 11 | 17.5 +/− 5.1% | 50 | 3 |
| 7 | 16.7 +/− 3.3% | 50 | 2 |
| 9 | 14.9 +/− 5.8% | 50 | 3 |
| 32 | 13.80% | 50 | 1 |
| 2 | 13.0 +/− 3.3% | 50 | 5 |
| 26 | 9.80% | 50 | 1 |
| 23 | 8.50% | 50 | 1 |
| 18 | 2.4 +/− 2.3% | 50 | 2 |

FIG. 1 shows dose response curves for compound 5 observed in 3 experiments where compound 5 was added in 1 µM, 10 µM, 50 µM and 100 µM quantities and the samples analysed for IL-1 induced COX-2 expression as above.

Effect of Glucocorticoids on MIF Antagonism

In Vitro Assay of MIF Antagonism in Presence of Glucocorticoid.

Figure 2:
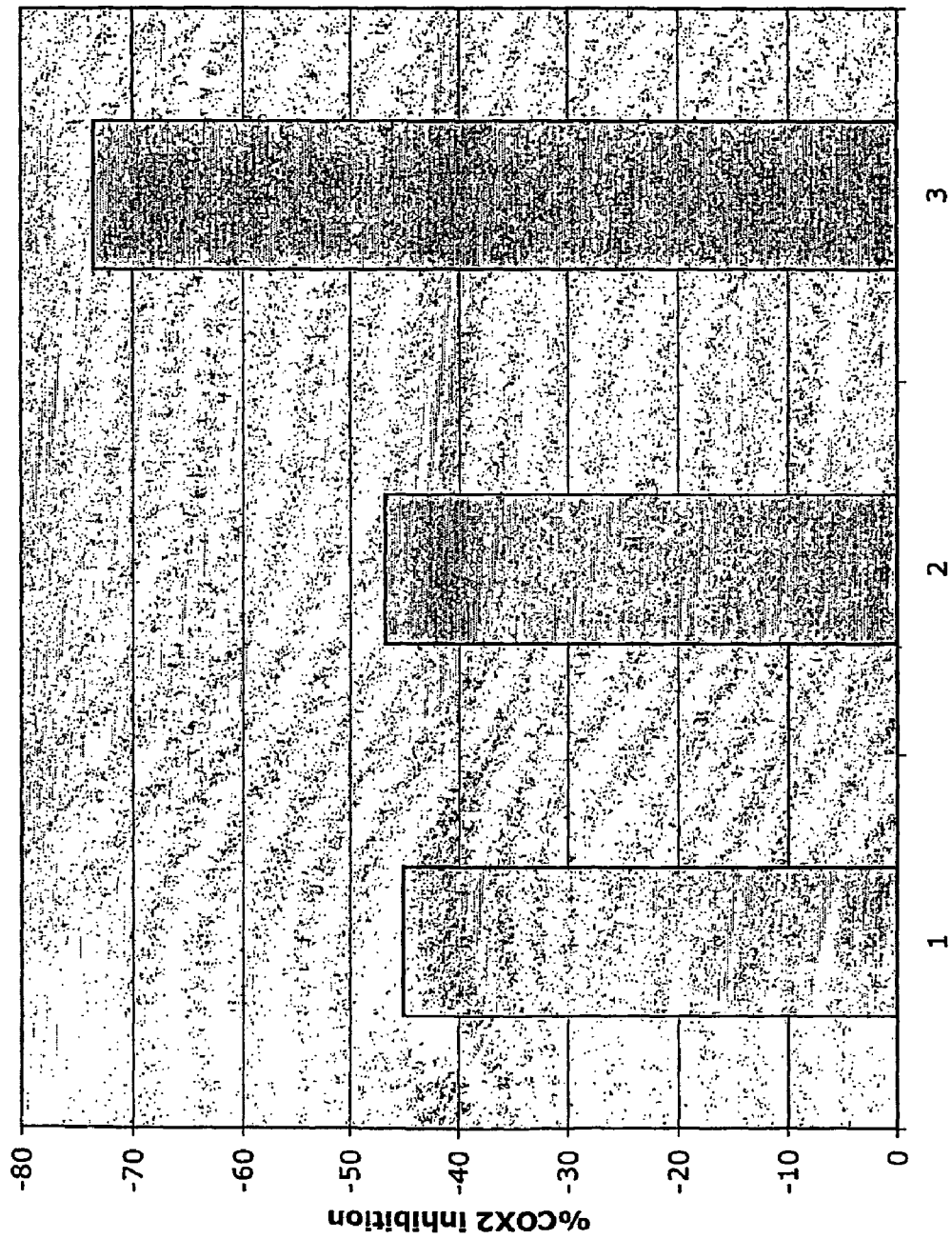
FIG. 2 graphically depicts the effect of a combination of dexamethasone and benzimidazol-2-one-5-pentanoate (compound 5) on IL-1 induced COX-2 expression.

The above in vitro assay for analysing IL-1 induced COX-2 expression was repeated using Compound 5 (50 µM) (column 1), dexamethasone (10$^{-9}$ M) (column 2) or a combination of dexamethasone (10$^{-9}$ M) and Compound 5 (50 µM) (column 3). The results are shown in Table 2 and FIG. 2.

TABLE 2

| Experiment | Compound | % Inhibition |
| --- | --- | --- |
| 1 | Compound 5 | 45.1 |
| 2 | Dexamethasone | 46.8 |
| 3 | Compound 5 + dexamethasone | 73.6 |

In Vitro Assay for the Effect of a MIF Antagonist and a Glucocorticoid on IL-1 Induced Phosphorylation of ERK.

S112 human dermal fibroblasts cultured in RPMI (serum-free) medium were stimulated with recombinant human IL-1 0.1 ng/ml, as described herein, for 30 minutes, with or without the addition of dexamethasone 10$^{-9}$M or benzimidazol-2-one-5-pentanoate (compound 5) (50 µM). The phosphorylation (activation) of ERK was assessed using Western blotting with a mAb specific for the phosphorylated (activated) form of ERK. In brief, cells were disrupted by repeated aspiration through a 21-gauge needle. After incubation on ice for 10 min and microcentrifugation at 3000 rpm for 15 min (4° C.), the supernatants were removed, the protein concentration was determined, and the lysates were stored at −80° C. Equal amounts of cellular proteins were fractionated on 10% SDS-polyacrylamide electrophoresis gels and transferred to polyvinylidene difluoride membranes. Immunoblotting was performed using antibodies directed against phospho-p44/42 (ERK) and total p44l42 according to the manufacturer's instructions. The intensity of ERK activation is proportional to the size and optical density (darkness) of the resulting blots. Total ERK blots serve as a loading control, such that changes in phosphorylated ERK represent changes in phosphorylation and not in total ERK protein. In these experiments, ERK activation was demonstrated in response to IL-1 (lane 2) compared to untreated cells (control) (lane 1). ERK activation by IL-1 was not inhibited by benzimidazol-2-one- 5-pentanoate (compound 5) (IL-1+MIF-a) (lane 3) or dexamethasone alone (not shown), but was powerfully inhibited by the combination of benzimidazol-2-one-5-pentanoate (compound 5) and dexamethasone (IL-1+MIF-a+DEX) (lane 4). The results are shown in FIG. 3.

In Vivo Assay of MIF Antagonism: Endotoxic Shock

Figure 4:
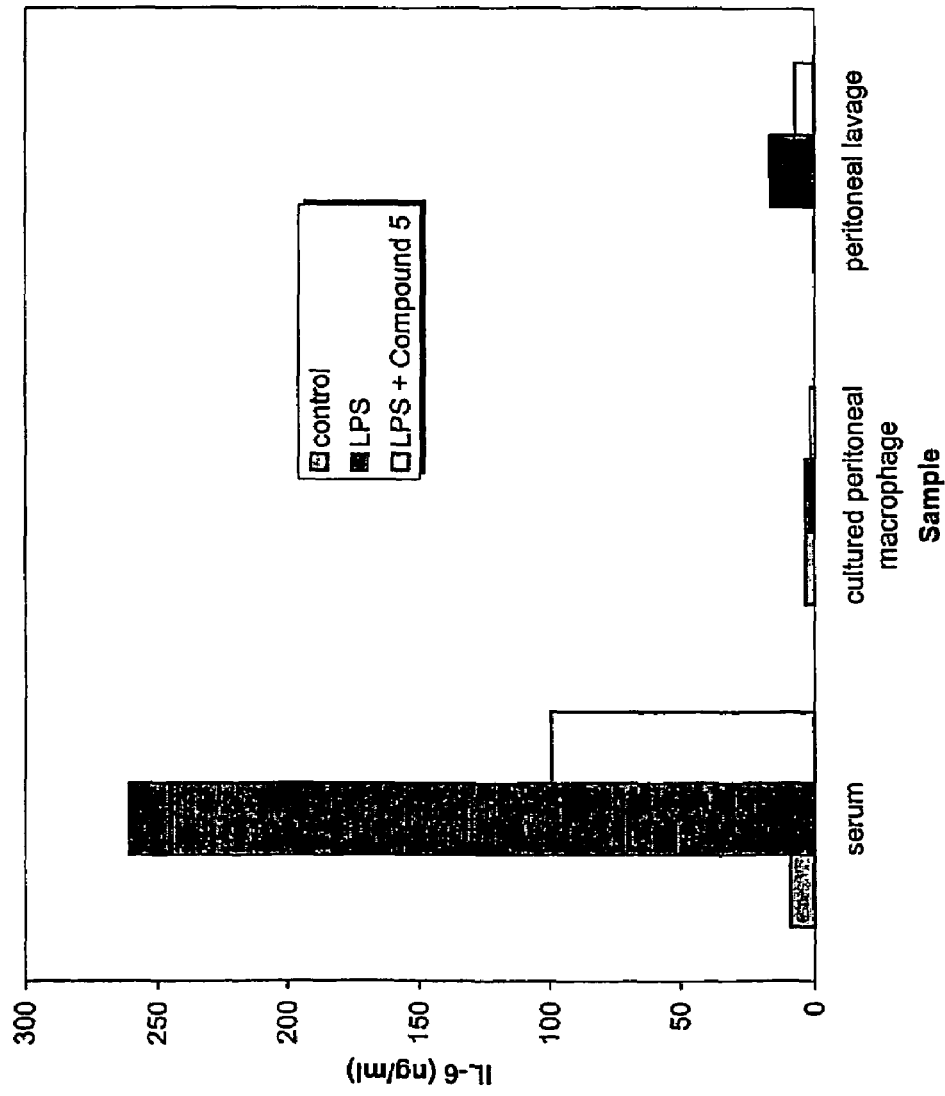
FIG. 4 graphically depicts the effect of benzimidazol-2-one-5-pentanoate (compound 5) on in vivo serum IL-6 production in a murine endotoxic shock model.

The activity of compound 5 was studied in the murine endotoxic shock model. This model has been previously shown to be dependent on MIF (21). Administration of a substance which inhibits the cytokine or biological activity of MIF would be expected to result in a reduction in serum levels of cytokines such as IL-1 or IL-6. Endotoxaemia was induced by intra-peritoneal injection of lipopolysaccharide (LPS) (15 mg/kg) in 400 μl saline. Mice were treated with a saline solution (control) only, a saline solution and LPS, or LPS and compound 5 at a dose of 15 mg/kg body weight, administered by intra-peritoneal injection at 24 hours, 12 hours and 1 hour before intra-peritoneal LPS injection. After 1.5 hours mice were humanely killed by $CO_2$ inhalation then neck dislocation. Serum was obtained from blood obtained by cardiac puncture prior to death and measured for cytokines including interleukin 1 (IL-1) and interleukin 6 (IL-6) by ELISA. The production of IL-1 and IL-6 has been previously shown to be dependent on MIF (22). Macrophages were obtained by lavage of the peritoneal cavity using normal saline and placed into 24 well tissue culture plates for 18 hours in RPMI/10% FCS. The cultured peritoneal macrophage supernatants were then analysed for cytokines including IL-6. The peritoneal lavage supernatants were also analysed for cytokines including IL-6. The results are provided in Table 3 and FIG. 4.

TABLE 3

| Experiment | Serum IL-6 (ng/ml) | Cultured peritoneal macrophage IL-6 (ng/ml) | Peritoneal lavage IL-6 (ng/ml) |
|---|---|---|---|
| control | 8.81 | 3.39 | 0 |
| LPS only | 261.05 | 3.40 | 16.11 |
| LPS + compound 5 | 99.78 | 1.33 | 7.07 |

Figure 5:
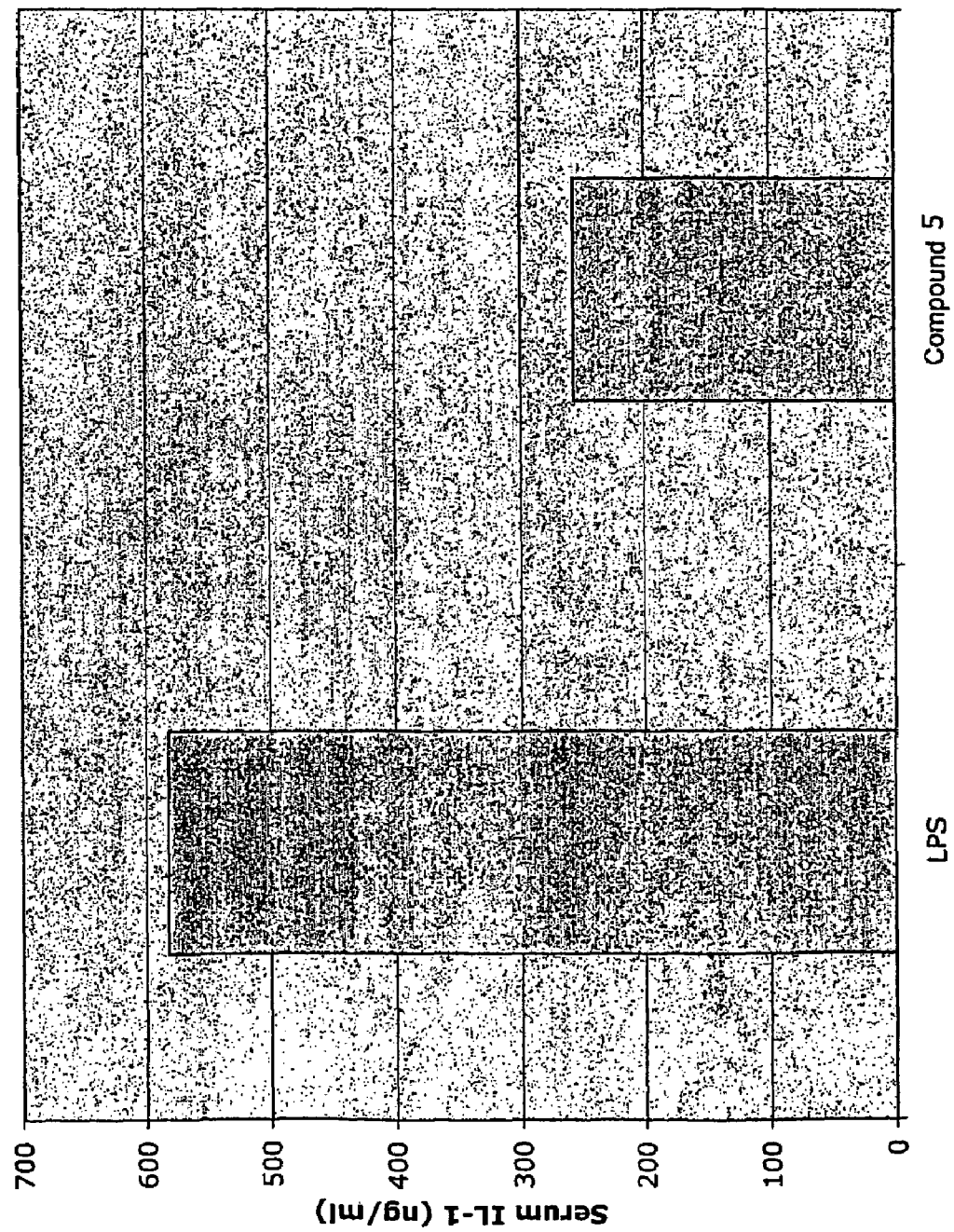
FIG. 5 graphically depicts the effect of benzimidazol-2-one-5-pentanoate (compound 5) on in vivo serum IL-1 production in a murine endotoxic shock model.

FIG. 5 shows analysis of serum IL-1 (ng/ml) obtained from mice in which when LPS was administered alone or in combination with compound 5. A marked reduction in serum IL-1 concentration was observed in animals treated with compound 5.

The effect of compound 5 was tested under a variety of conditions in animals exposed to endotoxic shock induced as above by the injection of 15 mg/kg LPS by intraperitoneal injection. In each case compounds were administered by intraperitoneal injection at a dose of 15 mg/kg. Compound 5 administration was associated with reductions in serum IL-1, IL-6, and TNF concentration whether administered by intraperitoneal injection (IP) or by oral gavage, and under a variety of administration regimens. These data suggest compounds of Formula I are active inhibitors of the biological or cytokine activity of MIF in vivo.

TABLE 4

Serum cytokine levels in response to LPS: effects of compound 5

| Treatment regimen* | Result | Control | LPS | LPS + cpd | Inhibitory effect |
|---|---|---|---|---|---|
| IP injection 15 mg/kg −24, −6, −1 h | Serum IL-1 at 1.5 h | 23.53 | 42.49 | 39.82 | Y |
| Oral gavage 15 mg/kg −24, −6, −1 h | Serum IL-1 at 1.5 h | | 103.7 | 47.1 | Y |
| IP injection 15 mg/kg −24, −6, −1 h | Serum IL-1 at 6 h | | 786.6 | 170.2 | Y |
| IP injection 15 mg/kg −24, −12, −1 h | Serum IL-1 at 1.5 h | | 484.8 | 283.8 | Y |
| IP injection 15 mg/kg −18 h | Serum IL-1 at 1.5 h | | 301.5 | 105.9 | Y |
| Oral gavage 15 mg/kg −24 h | Serum IL-1 at 1.5 h | 23.53 | 292.0 | 152.6 | Y |
| Oral gavage 5 mg/kg −24 h, −1 h | Serum IL-1 at 1.5 h | | 237.0 | 182.5 | Y |
| Oral gavage 15 mg/kg −24 h | Serum IL-6 at 1.5 h | 20360 | 121100 | 80250 | Y |
| IP injection 15 mg/kg −24, −12, −1 h | Serum IL-6 at 1.5 h | | 92790 | 75260 | Y |
| IP injection 15 mg/kg −24, −12, −1 h | Serum IL-6 at 6 h | | 261900 | 162800 | Y |
| IP injection 15 mg/kg −1 h | Serum IL-6 at 6 h | | 215100 | 150300 | Y |
| IP injection 5 mg/kg −1 h | Serum IL-6 at 6 h | | 215100 | 108200 | Y |

TABLE 4-continued

Serum cytokine levels in response to LPS: effects of compound 5

| Treatment regimen* | Result | Control | LPS | LPS + cpd | Inhibitory effect |
|---|---|---|---|---|---|
| IP injection 1 mg/kg −1 h | Serum IL-6 at 6 h | | 215100 | 101000 | Y |
| IP injection 15 mg/kg −18 h | Serum TNF at 1.5 h | | 4263 | 2422 | Y |

In Vitro Toxicity Assay

Figure 6:
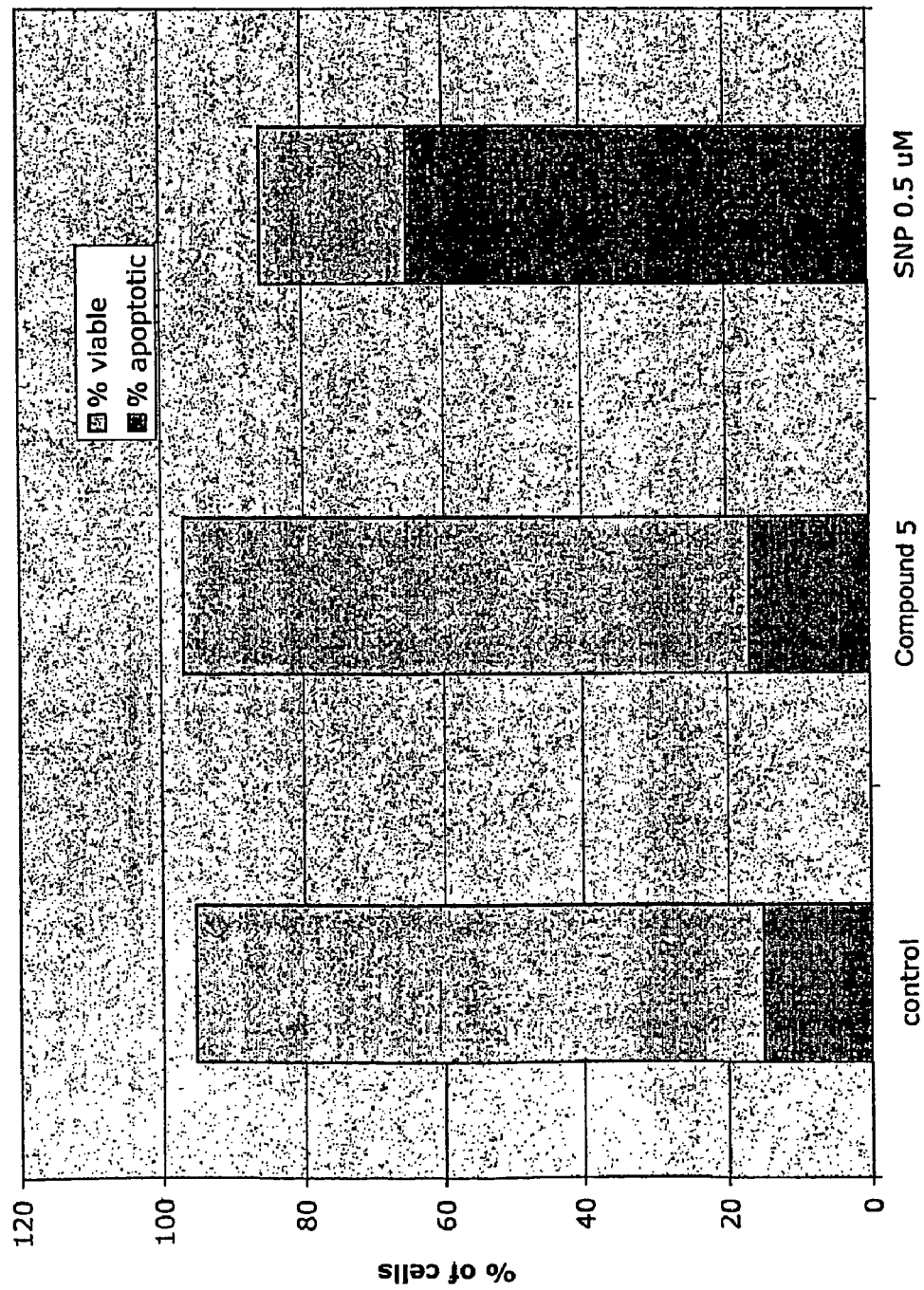
FIG. 6 graphically depicts the cytotoxicity effect of benzimidazol-2-one-5-pentanoate (compound 5) in vitro.
Figure 7:
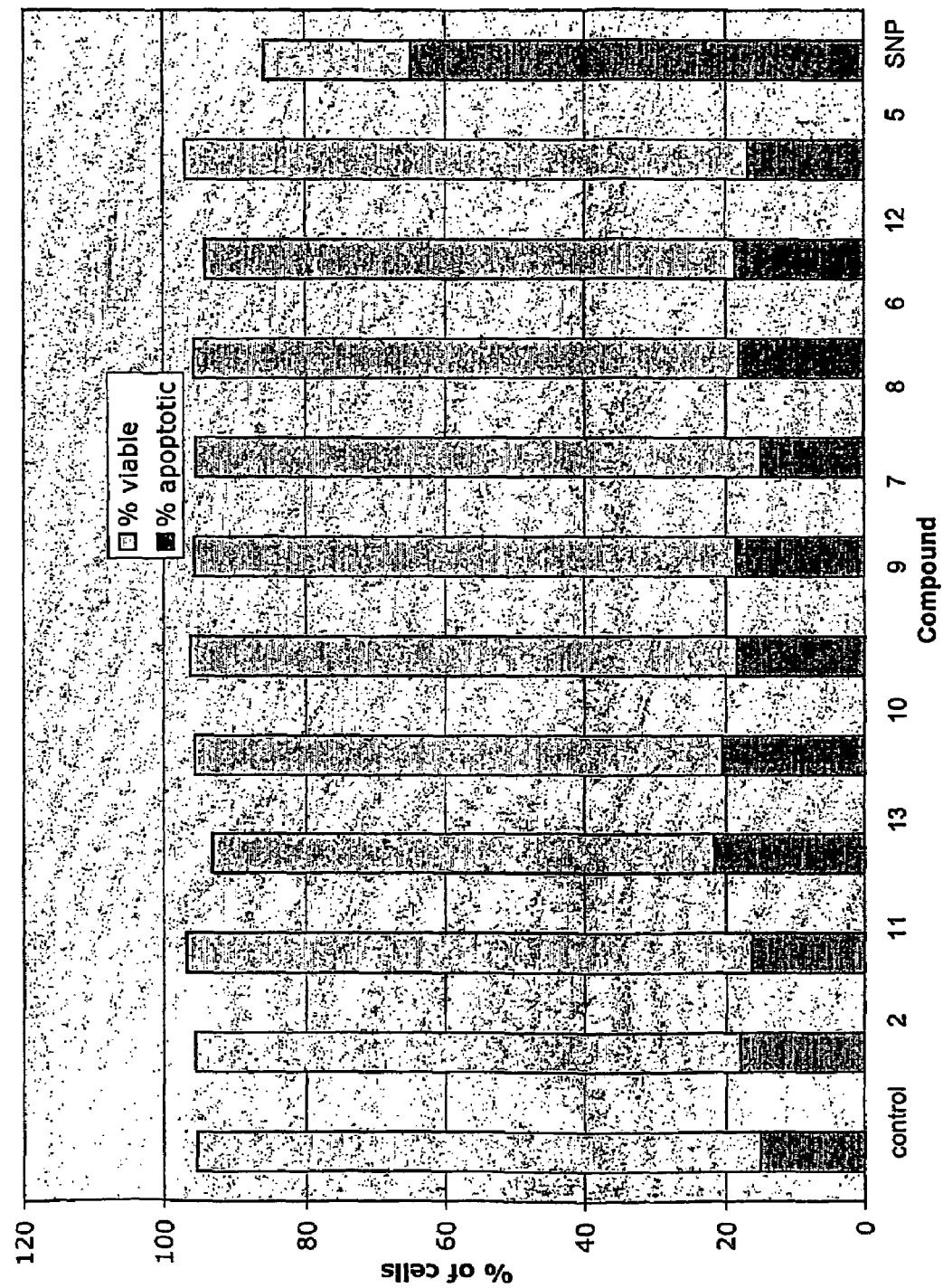
FIG. 7 graphically depicts the cytotoxicity effect of a number of compounds of formula (I) in vitro.

The compounds of formula (I) may have low toxicity towards cells. The toxicity of compounds of formula (I) were examined in vitro to assess cytotoxicity. Human dermal fibroblast cell line (S112) cells were exposed to vehicle (control), compounds of formula (I) (50 µM) or sodium nitroprusside (SNP) (0.5 µM. SNP is a positive control agent which induces dose-dependent apoptosis in S112 cells. Toxicity was assessed by analysis of apoptosis using flow cytometric detection of cell surface Annexin V binding and propidium iodide staining. At least 5000 events were analysed for each experiment. Cells positive for both Annexin V and propidium iodide were designated as apoptotic and cells negative for both Annexin V and propidium iodide were designated as viable. Results are expressed as the percentage (%) of cells with each of these labels. No compound of formula (I) induced apoptosis at levels above the control whereas SNP induced a high level of apoptosis. The results for compound 5 are shown in FIG. 6. The results for a number of compounds of formula (I) are shown in FIG. 7.

In Vitro Assay of MIF Antagonism: T Cell Activation

Activation of T lymphocyte responses is a critical event in the development of autoimmune and chronic inflammatory diseases. T lymphocyte activation in vitro and in vivo are known to be dependent upon the presence of bioactive MIF. For example, administration of specific monoclonal antibodies directed against MIF have been shown to inhibit development of T cell activation in vitro and of cutaneous delayed-type hypersensitivity responses in vivo (22) (7). The demonstration that compounds inhibitory of the cytokine and biological activity of MIF are inhibitory of T cell activation in vitro will be seen by those skilled in the art as supportive of the biological and functional antagonism of MIF provided by those compounds.

C57BL6/J male mice, aged 7-10 weeks old, were immunised with 200 µg of methylated bovine serum albumin (mBSA) dissolved in 20 µL of saline, emulsified in 200 µL of Freund's complete adjuvant (FCA) by subcutaneous injection. Seven (7) days later mice received a booster immunisation with 100 µg mBSA in 10 µL saline plus 100 µL FCA by subcutaneous injection. After a further seven (7) days mice were killed and spleens collected aseptically into Hanks buffered saline solution (HBSS). A single cell suspension was prepared in Petri dishes by flushing DMEM using a 26G needle and 2 mL syringe. The resulting cell suspension was centrifuged for 5-7 minutes and supernatant discarded. Erythrocytes were lysed using a solution containing 0.579% $NH_4Cl$, 0.000037% EDTA, and 0.1% $NaHCO_3$ in a 37° C. water bath. Tubes were then filled with DMEM and centrifuged for 5-7 minutes. The cell-containing pellet was then resuspended in DMEM containing 5% fetal calf serum TICS) and 0.05% 2-mercapto-ethanol at a concentration of $1 \times 10^6$ cells/mL and plated at $1 \times 10^5$ cells/well in 96-well plastic tissue culture plates. Test substances (compound or vehicle) were added and incubated for 1 hour in a 37° C., 5% $CO_2$ incubator. The specific stimulating antigen, mBSA, was then added at 10-50 µg/ml and plates incubated for 30 hours in a 37° C., 5% $CO_2$ incubator. Tritiated $^3$H-thymidine was then added at a concentration of 0.5 µCi/well for a further 18 hours. Cells were harvested on a Packard cell harvester, and the harvested material added to 750 µL/tube scintillation fluid. Scintillation counts were read on a Wallac beta-emission counter. Incorporation of $^3$H-thymidine into DNA is a measure of cell proliferation, and hence of antigen-specific T cell activation.

Figure 8:
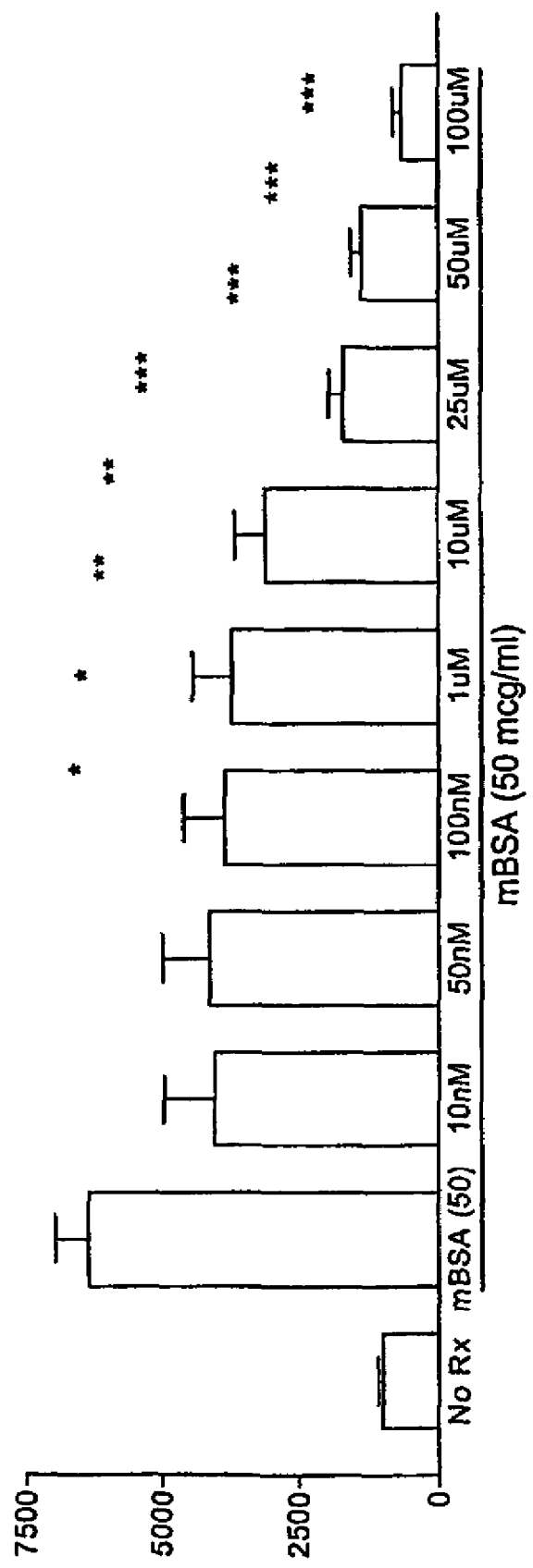
FIG. 8 depicts graphically the effect of benzimidazol-2-one-5 pentanoate (compound 5) on antigen-specific activation of splenic T lymphocytes from mice pre-immunised against mBSA. Activation is measured using tritiated ($^3$H)-thymidine incorporation, as a measure of antigen-induced T cell proliferation.

As shown in FIG. 8, T cell proliferation was significant increased in the presence of the specific sensitising antigen, mBSA, at 50 µg/mL. The addition of compound 5 in increasing concentrations exerted a dose-dependent and statistically significant inhibitory effect on antigen-specific T cell activation. In FIG. 8, asterisks signify a statistically significant result (*$p<0.05$, $p<0.01$, *$p<0.001$).

The concentration at which T cell activation was suppressed by 50% compared to vehicle-only-treated cells (EC50) was calculated using Prism® software. The EC50 for compound 5 in experiments where T cells were stimulated with 50 µg/ml of mBSA was 13.75 µM. Further compounds were also tested for their ability to inhibit antigen-specific T cell activation as a marker of the inhibition of the cytokine or biological activity of MIF using this assay. Table 5 lists the EC50 for each compound in this assay, performed with concentrations of mBSA of either 50 or 10 µg/ml.

TABLE 5

Inhibition of T cell activation by compounds.

| | mBSA 50 µg/ml | | mBSA 10 µg/ml | |
|---|---|---|---|---|
| Compound | EC50(µM) | no. expts | EC50(µM) | no. expts |
| 27 | 1.29 | 1 | 9.15 | 1 |
| 26 | 2.31 | 1 | 10.18 | 1 |
| 28 | 7.37 | 1 | 2.19 | 1 |
| 19 | 9.36 | 1 | 2.25 | 1 |
| 15 | 10.12 | 1 | 9.40 | 1 |
| 17 | 10.72 | 1 | 2.91 | 1 |
| 5 | 13.75 | 5 | 15.30 | 2 |
| 33 | 13.95 | 1 | 24.77 | 1 |
| 16 | 25.99 | 1 | 23.84 | 1 |
| 18 | 33.98 | 1 | 19.31 | 1 |
| 7 | 44.76 | 3 | 33.89 | 1 |
| 34 | 49.89 | 1 | 13.50 | 1 |
| 11 | 50.73 | 3 | 44.44 | 1 |
| 9 | 61.92 | 3 | 76.96 | 1 |
| 13 | 71.73 | 4 | 53.28 | 1 |
| 10 | 77.54 | 3 | >100 | 1 |
| 12 | 77.89 | 3 | >100 | 1 |
| 8 | >100 | 3 | 25.43 | 1 |

TABLE 5-continued

Inhibition of T cell activation by compounds.

| | mBSA 50 µg/ml | | mBSA 10 µg/ml | |
|---|---|---|---|---|
| Compound | EC50(µM) | no. expts | EC50(µM) | no. expts |
| 6 | >100 | 3 | 25.84 | 1 |
| 19 | >100 | 1 | 45.56 | 1 |
| 32 | >100 | 1 | >100 | 1 |
| 25 | >100 | 1 | >100 | 1 |
| 22 | >100 | 1 | >100 | 1 |
| 2 | (not done) | | 7.29 | 2 |

In Vivo Assay of MIF Antagonism: Cutaneous Delayed-Type Hypersensitivity (DTH) to mBSA As noted above, cutaneous delayed-type hypersensitivity reactions (DTH) are an in vivo test of T cell activation. DTH reactions have been shown to be dependent on the presence of bioactive MIF, as shown by suppression of these reactions with monoclonal anti-MIF antibodies (22). A compound which inhibits the cytokine of biological activity of MIF may be expected to inhibit the development of DTH reactions in vivo. DTH reactions were induced in mice developing antigen-induced arthritis (see below). C57BL6/J male mice, aged 7-10 weeks old, were immunized on day 0 with 200 µg methylated BSA (mBSA) emulsified in 200 µl of Freund's complete adjuvant (FCA) injected subcutaneously into the flank skin. Mice were treated with compound 5, administered by intraperitoneal injection, once per 24 hours at a dose of 15 mg/kg body weight. After seven days, mice received 100 µg mBSA and 100 µl FCA by intradermal injection at the base of the tail. After a further 14 days, arthritis was induced by intra-articular injection of 30 µg mBSA in 10 µl of sterile saline into the left knee, the right knee being injected with sterile saline alone. DTH reactions were induced as follows: these mice were challenged 24 h before the end of the experiment by intradermal injection of 50 µg mBSA in 20 µl saline into one hind footpad. A similar volume of saline was injected into the contralateral footpad as a control. Footpad swelling was quantified 24 h later using a micrometer. DTH was recorded as the difference in skin swelling between mBSA and saline-injected footpads, and expressed as change in footpad thickness (Δmm). A reduction in skin thickness is consistent with an inhibitory effect on the biological or cytokine activity of MIF.

Figure 9:
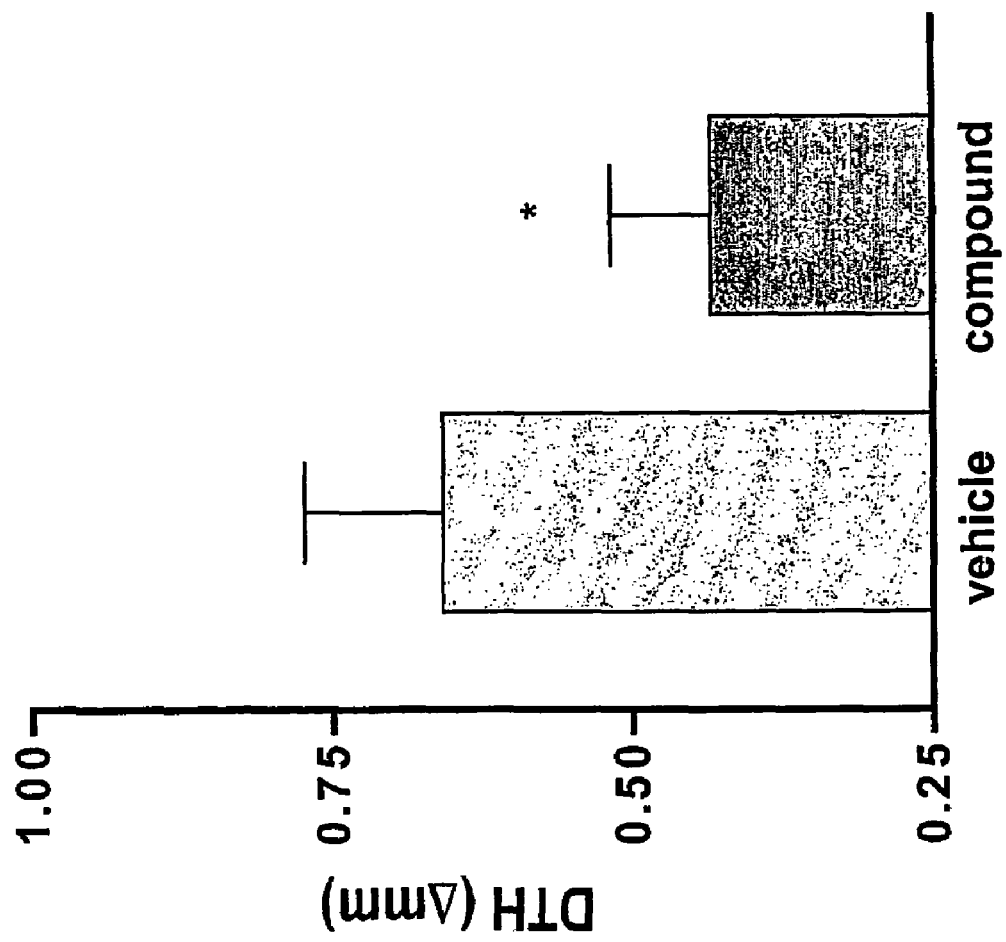
FIG. 9 depicts graphically the effect of benzimidazol-2-one-5 pentanoate (compound 5) on cutaneous delayed-type hypersensitivity reactions in vivo.

As shown in FIG. 9, a statistically significant reduction in cutaneous DTH reactions was observed in mice treated with compound 5, compared to mice treated with vehicle (p<0.05).

In Vivo Assay of MIF Antagonism: Antigen-Induced Arthritis.

Rheumatoid arthritis is a common, serious, chronic inflammatory disease affecting synovial joints, of which the etiology is unknown. Rheumatoid arthritis is one of the most common autoimmune or chronic inflammatory diseases, and can be seen as a model for other, less common, autoimmune and chronic inflammatory diseases. MIF has been confirmed as an important mediator in several animal models of rheumatoid arthritis, through studies in which antagonism of MIF with a monoclonal anti-MIF antibody exerted significant inhibitory effects on disease (23), (24), (8). Included among the animal models of rheumatoid arthritis in which MIF has been shown to be an essential factor is murine antigen-induced arthritis (8). A compound which inhibits the cytokine of biological activity of MIF might be expected to inhibit the development of murine antigen-induced arthritis in vivo.

Antigen-induced arthritis was induced in mice. C57BL6/J male mice, aged 7-10 weeks old, were immunized on day 0 with 200 µg methylated BSA (mBSA) emulsified in 200 µl of Freund's complete adjuvant (FCA) injected subcutaneously into the flank skin. Mice were treated with compound 5, administered by intraperitoneal injection, once per 24 hours at a dose of 15 mg/kg body weight. After seven days, mice received 100 µg mBSA and 100 µl FCA by intradermal injection at the base of the tail. After a further 14 days, arthritis was induced by intra-articular injection of 30 µg mBSA in 10 µl of sterile saline into the left knee, the right knee being injected with sterile saline alone.

Arthritis was analysed histologically at day 28 after first immunisation. Knee joints were dissected and fixed in 10% buffered formalin for 7 days. Fixed tissues were decalcified for 3 weeks in 15% ethylene-diamine-tetra-acetic acid (EDTA), dehydrated and embedded in paraffin. Sagittal sections (5 µm) of the knee joint were stained with Safranin-O and counterstained with fast green/iron hematoxylin. Histological sections were scored from 0 to 3 for four parameters: Synovitis was defined as hyper-cellularity of the synovium including pannus formation. Joint space exudate was identified as leukocytes, discretely or in aggregates, in the joint space. Cartilage degradation was defined as the loss of Safranin-O staining of articular cartilage (0=full stained cartilage, 3=totally unstained cartilage). Bone damage was defined as the extent and depth of the subchondral bone invasion by pannus. A total score was also generated from the sum of these four parameters (maximum 12).

Figure 10:
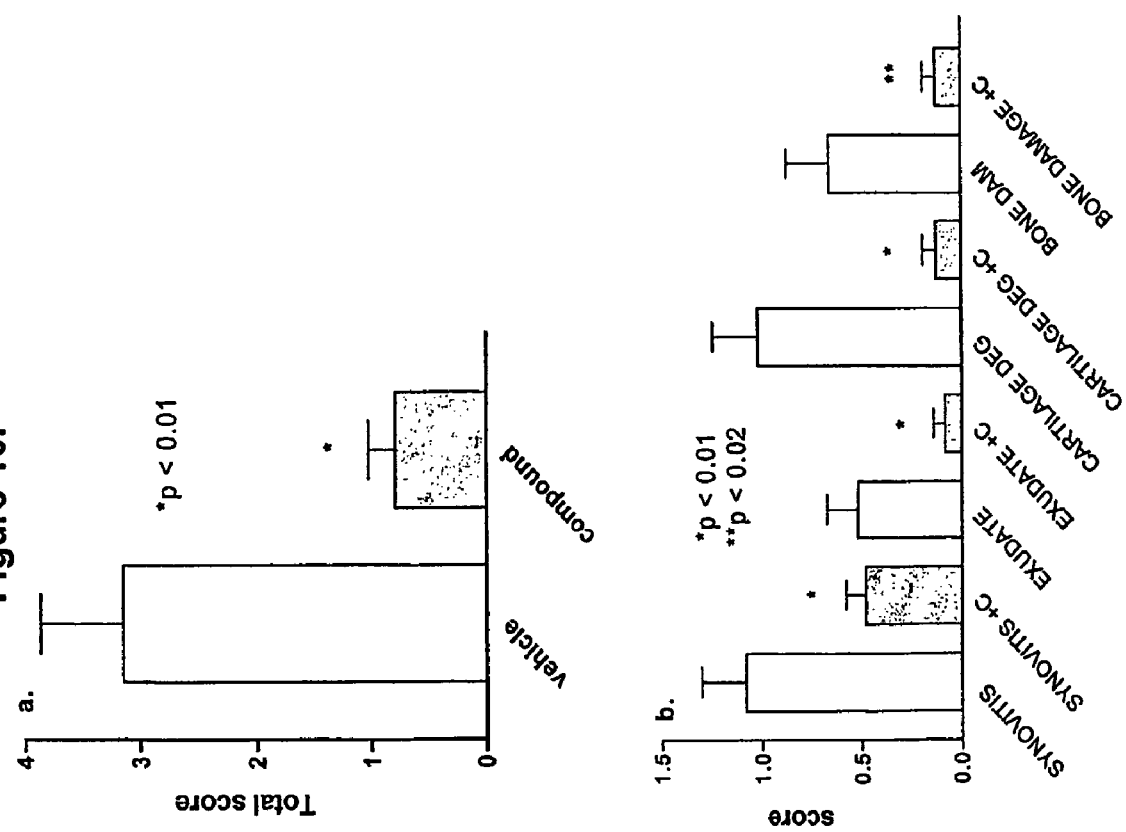
FIG. 10 depicts graphically the in vivo effects of benzimidazol-2-one-5 pentanoate (compound 5) on murine antigen induced arthritis, an animal model of rheumatoid arthritis.

The results of treating mice with compound 5 are shown in FIG. 10. In FIG. 10a, the total arthritis score for vehicle and compound-treated animals is presented graphically. A statistically significant reduction in total arthritis score is seen (p=0.0024). In FIG. 10b, individual parameters of arthritis are presented graphically. Statistically significant reductions in the severity of all individual parameters of arthritis can be seen for animals treated with compound 5.

An additional compound of Formula I has also been tested in the murine antigen induced arthritis model. Results for compound 13 are provided in table 6. Compound 13 also exerted an inhibitory effect on the severity of murine antigen induced arthritis.

TABLE 6

Effects of compound 13 in murine antigen induced arthritis.

| | Total arthritis score (mean ± SEM) | Number of experiments |
|---|---|---|
| vehicle | 6.25 ± 0.2 | 2 |
| compound | 5.17 ± 1.9 | 3 |

In Vivo Assay of MIF Antagonism: Ex Vivo T Cell Activation

As MIF is important in T cell activation, a compound capable of inhibiting the cytokine or biological activity of MIF might be expected to be exert inhibitory effects on T cell responsiveness. In vivo administration of such a compound might be expected to exert effects on T cell responsiveness even after the T cells have been removed from exposure to the compound, that is, if T cells were studied ex vivo after in vivo treatment with the MIF antagonist compound. To measure ex vivo antigen-specific T cell activation, draining lymph nodes from arthritic limbs or spleens were removed from mice with murine antigen induced arthritis, induced as above with mBSA, at day 28 after first immunisation and a single cell suspension prepared in DMEM containing 5% FCS and 0.05% 2-mercaptoethanol. $1 \times 10^5$ cells/200 µl were cultured in triplicate in the presence or absence of mBSA (0.1, 1.0, 10 µg/ml) in 96-well plates for 48 hours (37° C., 5% $CO_2$.) The T cell proliferation response was determined by measuring $^3$H-thymidine incorporation during the final 18 hr. The cells were harvested and radioactivity incorporation into the DNA was measured with a Wallac 1409 liquid scintillation counter. The means of each triplicate culture were calculated. Each experiment comprised at least three individual animals and the results presented represent the mean±SEM of groups of animals in each experiment. The percentage inhibition of T cell proliferation was calculated using the result of the $^3$H-2.0 thymidine incorporation of cells from compound-treated animals subtracted from the $^3$H-thymidine incorporation of cells from vehicle-treated animals.

Figure 11:
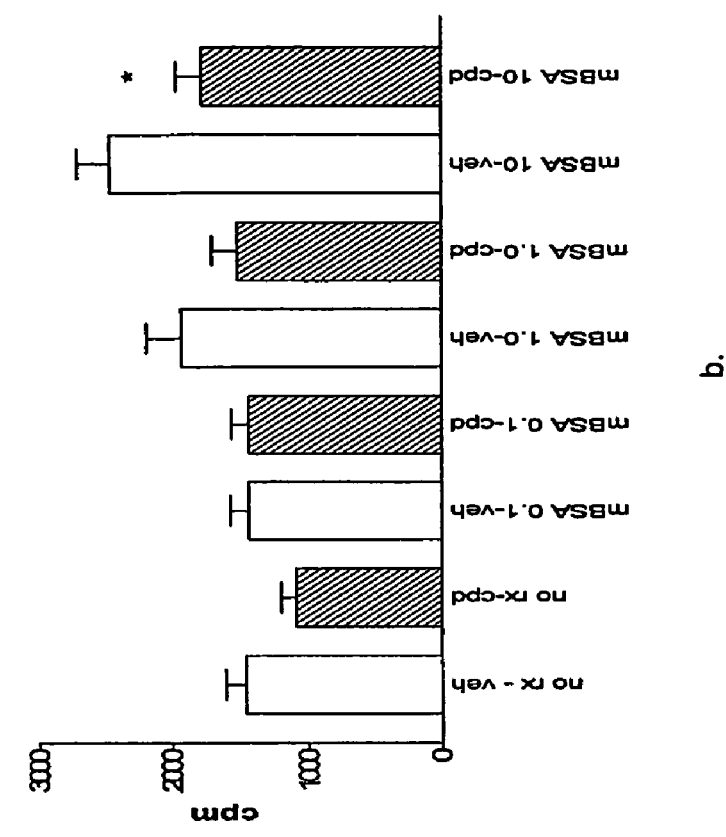
FIG. 11 depicts graphically the effect of in vivo treatment with compounds 5 and 13 on the ex vivo antigen-specific activation of lymph node and splenic T cells in response to mBSA.
Figure 11:
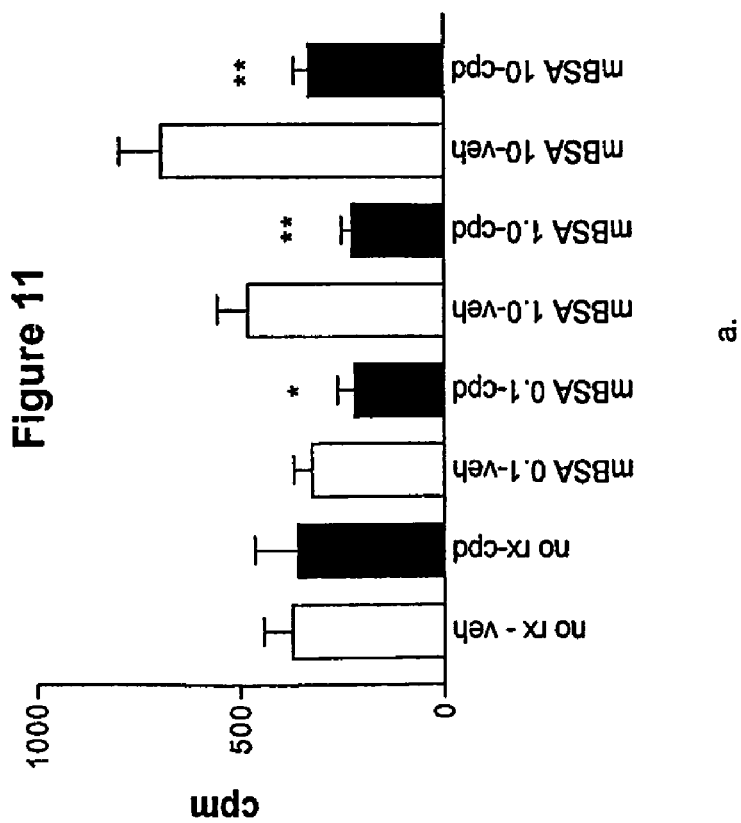

FIG. 11a depicts graphically the effect of in vivo treatment with compound 5 on the ex vivo activation of lymph node T cells in response to mBSA. As can be seen, cells from mice treated in vivo with compound 5 (filled bars) exhibited reduced proliferative responses to mBSA compared to cells from mice treated with vehicle. Representative of at least three separate experiments, each in triplicate and each including several individual animals.

FIG. 11b depicts graphically the effect of in vivo treatment with compound 13 on the ex vivo activation of splenic node T cells in response to mBSA. As can be seen, cells from mice treated in vivo with compound 13 (hatched bars) exhibited reduced proliferative responses to mBSA compared to cells from mice treated with vehicle. As can be seen from table 7, in vivo administration of compound 13 and compound 5 each exert an inhibitory effect on ex vivo splenic T cell proliferation.

TABLE 7

Inhibition of ex vivo splenic T cell activation by in vivo treatment with compounds.

| Compound | % inhibition | [mBSA] (µg/mL) | no. expts |
|---|---|---|---|
| 13 | 28% | 10 | 1 |
| 5 | 30% | 10 | 3 |
| 5 | 33% | 1 | 3 |

In Vitro Assay of MIF Antagonism: Dermal Fibroblast Proliferation Induced by Recombinant MIF.

It is well known to those skilled in the art that MIF is able to induce proliferation in a number of cell types including cells derived from patients with rheumatoid arthritis (25). It has also been demonstrated that antagonism of MIF with a monoclonal anti-MIF antibody can inhibit the proliferation of cells in vitro. A compound with the ability to inhibit the cytokine or biological function of MIF might be expected to inhibit the proliferative effect of MIF.

The activity of compound 5 was studied in a bioassay utilising MIF-induced proliferation of human dermal fibroblasts. S112 human dermal fibroblasts were propagated in RPMI/10% foetal calf serum (FCS). Prior to experimentation, cells were seeded at $10^5$ cells/ml in RPMI/0.1% 13SA for 18 hours. At time point zero, culture medium was replaced with RPMI/10% FCS and treatments administered. Cells were treated with recombinant human macrophage migration inhibitory factor (MIF) 50 ng/ml and/or compound 5 at a 1-1000 molar ratio to the concentration of MIF. At a time point 30 hours later, cells were pulsed with 1 µCi/well of $^3$H-thymidine. At a time point 48 hours after commencement of the experiment, cells were harvested using a semi-automated cell harvester. The radioactivity incorporated into DNA was determined by liquid scintillation counting, with results expressed as [$^3$H] thymidine incorporation.

Figure 12:
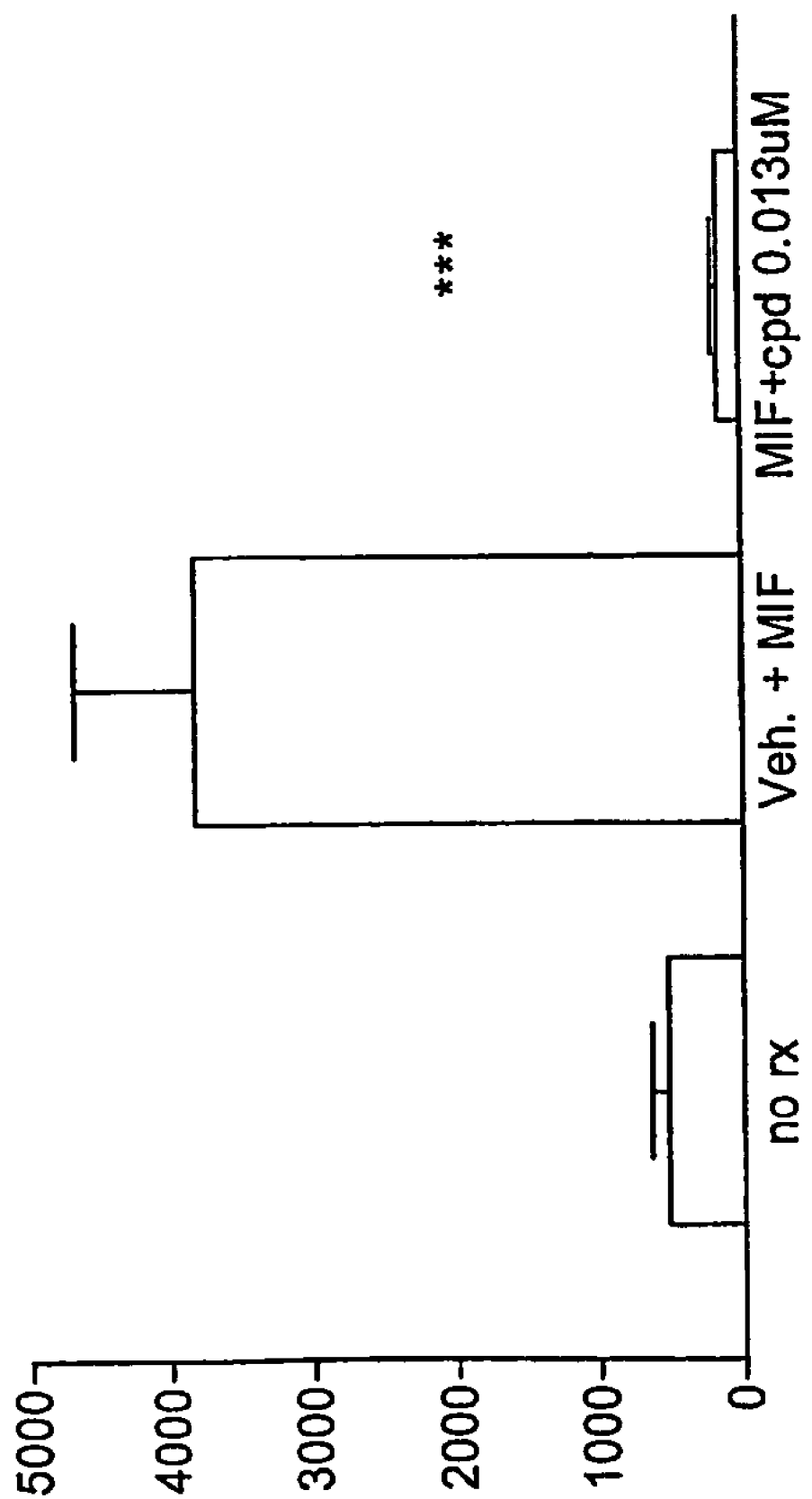
FIG. 12 depicts graphically the effect of benzimidazol-2-one-5 pentanoate (compound 5) on proliferation of cells treated with recombinant human MIF.

FIG. 12 depicts graphically the effect of compound 5 (0.013 µM) on proliferation of S112 cells treated with recombinant human MIF. A marked and statistically significant inhibitory effect was observed. The data presented are representative of four separate experiments.

In table 8, the inhibitory effect of compound 5 is expressed as the % inhibition of proliferation compared to the proliferation of rhMIF-treated cells.

TABLE 8

Inhibition of MIF-induced proliferation of s112 dermal fibroblast by compound 5.

| Compound | % inhibition | concentration (µM) | p value | no. expts |
|---|---|---|---|---|
| 5 | 98% | 0.013 | P < 0.001 | 4 |

In Vitro Assay of MIF Antagonism: Inhibition of Peritoneal Macrophage Cytokine Production.

MIF is known to be a participant in the innate immune response to toxins such as the bacterial endotoxin lipopolysaccharide (LPS). As shown above, antagonists of MIF can inhibit endotoxin-induced macrophage cytokine production in vivo. A compound with the ability to inhibit the cytokine or biological function of MIF might be expected to inhibit the activation of cytokine production by macrophages in response to LPS.

C57BL6/J male mice were injected intraperitoneally with 2 ml of thioglycollate. Five (5) days later peritoneal macrophages were collected by lavaging the peritoneum of anaesthetized mice with 3 ml of cold Hanks buffered saline solution. Cells from several mice were pooled, washed and re-suspended in DMEM supplemented with 5% FCS. Cells were plated in 96 well plastic tissue culture plates at $1 \times 10^5$ cells/well. Cells were treated with compound or vehicle for 1 hour in a 5% $CO_2$ incubator at 37° C. Cells were then treated with LPS (10-100 ng/ml) or recombinant human interferon-γ (10 units/ml) and incubated for 24 hours. After 24 hours, 50 µl of supernatant from each well was carefully removed and transferred to ELISA plates. The concentration of interleukin 1 (IL-1) or interleukin 6 (IL-6) was measured by ELISA. The concentration of compound at which LPS- or interferon-γ-induced cytokine release was suppressed by 50% compared to vehicle-only-treated cells (EC50) was calculated using Prism® software. Table 9 lists the EC50 for two compounds tested in this assay.

TABLE 9

Inhibition of murine peritoneal macrophage cytokine production.

| Compound | Interferon-γ (units/ml) | [LPS] ng/mL | EC50 (µM) | no. expts |
|---|---|---|---|---|
| IL-1 | | | | |
| 13 | | 100 | 16.67 | 1 |
| 5 | | 10 | 0.075 | 2 |
| IL-6 | | | | |
| 13 | 10 | | 9.82 | 1 |
| 5 | | 100 | 17.72 | 2 |

In Vitro Assay of MIF Antagonism: Inhibition of Peritoneal Macrophage Nitric Oxide Release.

MIF is able to induce or facilitate the expression and release of a wide variety of pro-inflammatory and/or destructive molecules. In the case of macrophages, in addition to the facilitation of cytokine release, MIF is able to facilitate the release of nitric oxide (NO) (26). A compound with the ability to inhibit the cytokine or biological function of MIF might be expected to inhibit the activation of NO production by macrophages.

C57BL6/J male mice were injected intraperitoneally with 2 ml of thioglycollate. Five (5) days later peritoneal macrophages were collected by lavaging the peritoneum of anaesthetized mice with 3 ml of cold Hanks buffered saline solution. Cells from several mice were pooled, washed and re-suspended in DMEM supplemented with 5% FCS. Cells were plated in 96 well plastic tissue culture plates at $1 \times 10^5$ cells/well. Cells were treated with compound or vehicle for 1 hour in a 5% $CO_2$ incubator at 37° C. Cells were then treated with LPS (10 ng/ml) and recombinant human interferon-γ (10 units/ml) and incubated for 24 hours. After 24 hours, 50 µl of supernatant from each well was carefully removed and transferred to ELISA plates. The concentration of nitrite in culture supernatants was measured by the Greiss assay (27). The results were defined as the percentage inhibition of nitrite concentration in compound-treated cell culture supernatants compared to that of vehicle-treated cells.

Table 10 displays the results for two compounds tested in this assay. Marked and statistically significant reductions in nitrite concentration were observed in the supernatants of cells treated with compounds.

TABLE 10

Inhibition of murine peritoneal macrophage nitric oxide production.

| Compound | Concentration (µM) | % Nitrite concentration inhibition from control | P value |
|---|---|---|---|
| 11 | 25 µM | 3.1 +/− 1.2% | |
| | 50 µM | 28.1 +/− 1.0% | P < 0.001 |
| | 100 µM | 65.5 +/− 0.8% | P < 0.001 |
| 5 | 25 µM | 11.1 +/− 1.3% | P < 0.001 |
| | 50 µM | 19.7 +/− 1.6% | P < 0.001 |
| | 100 µM | 28.6 +/− 1.5% | P < 0.001 |

In Vitro Assay of MIF Antagonism: Inhibition of Human Rheumatoid Arthritis Synovial Fibroblast Proliferation.

MIF is known to be a stimulus or participant in the proliferation of multiple cell types with relevance to disease states. For example, this been shown to be the case for the native resident cells of the synovial lesion of human rheumatoid arthritis, namely fibroblast-like synoviocytes (FLS). Lacey et al (26) reported that recombinant MIF induces proliferation of FLS, and moreover that a monoclonal anti-MIF antibody is able to suppress the proliferation of FLS induced by another cytokine, interleukin 1 (IL-1). A compound capable of inhibiting the cytokine or biological activity of MIF would be expected to be able to inhibit the IL-1-induced proliferation of human rheumatoid arthritis FLS.

Fibroblast-like synoviocytes (FLS) were obtained from synovium of rheumatoid (RA) patients undergoing joint replacement surgery and prepared according to Lacey et al (26). FLS were isolated using enzyme digestion and cultured in RPMI/10% fetal calf serum (FCS) as previously described. A single cell suspension was obtained by digesting minced synovial tissue with 2.4 mg/ml Dispase (grade II, 5 U/mg) 1 mg/ml collagenase (type II) and DNase (type 1). FLS were propagated in 10 cm culture plates in RPMI supplemented with 10% FCS at 37° C. in a 5% $CO_2$ humidified incubator. Cells beyond 3rd passage were more than 99% CD45−. Cells were used between passages 4 and 9. Cells from four individual human RA donor FLS used.

To determine the effect of compound 5 on FLS proliferation, DNA synthesis was measured by [$^3$H] thymidine incorporation. FLS were seeded overnight at $0.5 \times 10^5$ cells per well in 24 well tissue culture plates in RPMI/10% FCS. Cell growth was synchronised by culturing FLS in RPMI/0.1% bovine serum albumin for 24 h. FLS were treated with human recombinant IL-1β (0.1 ng/ml) and compound 5 (50 µM) or vehicle for 54 h prior to cells being pulsed for 18 h with 1 µCi/ml $^3$H-thymidine. Duplicate or triplicate cultures were used for each determination as noted. FLS were detached using Trypsin-EDTA, harvested using a cell harvester, and the radioactivity incorporated into DNA determined using a Wallac 1409 liquid scintillation counter. Results were expressed as the percentage of control (untreated) cell proliferation, and the mean±SEM of four experiments calculated.

As shown in Table 11, IL-1 statistically significantly induced the proliferation of human rheumatoid arthritis FLS. There was no effect of vehicle on proliferation, but compound 5 treatment was associated with a marked and statistically significant inhibition of IL-1-induced FLS proliferation.

These data are consistent with compound 5 being an inhibitor of the cytokine and biological activity of MIF.

TABLE 11

| Control | IL-1 | IL-1 + vehicle | IL-1 + compound 5 |
|---|---|---|---|
| 100 ± 0 | 167 ± 39 | 156 ± 32 | 18 ± 6 |

REFERENCES (1) David, J, Delayed hypersensitivity in vitro: its mediation by cell-free substances formed by lymphoid cell-antigen interaction. *Proceedings of the National Academy of Sciences USA,* 1966; 56:72-77.

(2) Weiser, W Y, Temple P A, Witek-Gianotti J S, Remold H G, Clark S C, Davis J R, Molecular cloning of cDNA encoding a human macrophage migration inhibitory factor, *Proceedings of the National Academy of Sciences USA,* 1989; 86:7522-7526.

(3) Leech M, Metz C N, Smith M, Weedon H, Holdsworth S R, Bucala R, et al. Macrophage migration inhibitory factor (MIF) in rheumatoid arthritis: Evidence for pro-inflammatory function and regulation by glucocorticoids. *Arthritis & Rheumatism* 1999; 42:1601-1608.

(4) Morand E F, Bucala R, Leech M. Macrophage migration inhibitory factor (MIF): An emerging therapeutic target in rheumatoid arthritis. *Arthritis & Rheumatism* 2003; 48:291-299.

(5) Calandra T, Bernhagen J, Metz C N, Spiegel L A, Bacher M, Donnelly T, et al. MIF as a glucocorticoid-induced modulator of cytokine production. *Nature* 1995; 377:68-71.

(6) Donnelly S C, Haslett C, Reid P T, Grant I S, Wallace W A H, Metz C N, I. Regulatory role for macrophage migration inhibitory factor in acute respiratory distress syndrome. *Nature Medicine* 1997; 3:320-323.

(7) Bacher M, Metz C N, Calandra T, Mayer K, Chesney J, Lohoff M, et al. An essential regulatory role for macrophage migration inhibitory factor in T-cell activation. *Proceedings of the National Academy of Sciences USA* 1996; 3:7849-7854.

(8) Santos L L, Hall P, Metz C N, Bucala R, Morand E F. Role of macrophage migration inhibitory factor (MIF) in murine antigen-induced arthritis: Interaction with glucocorticoids. *Clin. Exp. Immunol.* 2001; 123:309-314.

(9) Leech M, Santos L L, Metz C, Holdsworth S R, Bucala R, Morand E F. Control of macrophage migration inhibitory factor (MIF) by endogenous glucocorticoids in rat adjuvant arthritis. *Arthritis & Rheumatism* 2000; 43:827-833.

(10) Bucala R. MIF rediscovered: cytokine, pituitary hormone, and glucocorticoid-induced regulator of the immune response. *FASEB. J.* 1996; 10:1607-1613.

(11) Sabroe I, Pease J E, Williams T J. Asthma and MIF: innately Th1 and Th2. *Clin Exp Allergy* 2000; 30(9):1194-6.

(12) Harvey, I. W.; McFarlane, M. D.; Moody, D. J.; Smith, D. M. *J. Chem. Soc. Perkin Trans.*, 1988, 1, 681-689.

(13) Swantek J L, Cobb M H, Geppert T D. Jun N-terminal kinase/stress-activated protein kinase (JNK/SAPK) is required for lipopolysaccharide stimulation of tumor necrosis factor alpha (TNF) translation: glucocorticoids inhibit TNF translation by blocking JNK/SAPK. *Molecular and Cellular Biology* 1997; 17:6274-6282.

(14) Rogatsky I, Logan S K, Garabedian M J. Antagonism of glucocorticoid receptor transcriptional activation by the c-Jun N-terminal kinase. *Proc. Natl. Acad. Sci. U.S.A.* 1998; 95:2050-2055.

(15) Kassel O, Sancono A, Kratzschmar J, Kreft B, Stassen M, Cato A C. Glucocorticoids inhibit MAP kinase via increased expression and decreased degradation of MKP-1. *Embo J* 2001; 20(24):7108-16.

(16) Mitchell, R A, Metz C N, Peng T, Bucala R. Sustained mitogen-activated protein kinase (MAPK) and cytoplasmic phospholipase A2 activation by macrophage migration inhibitory factor (MIF). Regulatory role in cell proliferation and glucocorticoid action. *Journal of Biological Chemistry,* 1999; 274:18100-18106.

(17) M. N. Kosyakovskaya, A. V. Gordeeva, Ch. Sh. Kadyrov, *Chem. Het. Compounds,* 1972, 8, 351)

(18) Berg, S. S.; Newbery, G. *J. Chem. Soc.,* 1946, 642.

(19) Hopkins, K. T.; Wilson, D. W.; Bender, B. C.; McCurdy, D. R.; Hall, J. E. *J. Med. Chem.,* 1998, 41, 3872-3878.

(20) Sampey A V, Hall P, Bucala R, Morand E F. Macrophage migration inhibitory factor (MIF) activation of rheumatoid synoviocytes. *Arthritis & Rheumatism* 1999; 44:S283.

(21) Bernhagen, J, Calandra T, Mitchell R A, Martin S B, Tracey K J, Voelter W, et al. MIF is a pituitary-derived cytokine that potentiates lethal endotoxaemnia. *Nature* 1993; 365:756-759.

(22) Bozza M, Satoskar A B, Lin G, Lu B, Humbles A A, Gerard C, et al., Targeted disruption of Migration Inhibitory Factor gene reveals its critical role in sepsis. *Journal of experimental Medicine* 1999; 189: 341-346.

(23) Bernhagen J, Bacher M, Calandra T, Metz C N, Doty S B, Donnelly T, et al. An essential role for macrophage migration inhibitory factor in the tuberculin delayed-type hypersensitivity reaction. *Journal of Experimental Medicine* 1996; 183:277-282.

(24) Mikulowska A, Metz C N, Bucala R, Holmdahl R. Macrophage migration inhibitory factor is involved in the pathogenesis of collagen type II-induced arthritis in mice. *Journal of Immunology* 1997; 158:5514-5517.

(25) Leech M, Metz C N, Santos L L, Peng T, Holdsworth S R, Bucala R, et al. Involvement of macrophage migration inhibitory factor in the evolution of rat adjuvant arthritis. *Arthritis & Rheumatism* 1998; 41:910-917.

(26) Lacey D C, Sampey A V, Mitchell R, Bucala R, Santos L, Leech M, et al. Control of fibroblast-like synoviocyte proliferation by macrophage migration inhibitory factor (MIF). *Arthritis & Rheumatism* 2003; 48:103-9.

(27) Juttner S, Berrhagen J, Metz C N, Rollinghoff M, Bucala R, Gessner A. Migration inhibitory factor induces killing of *Leishmania major* by macrophages: dependence on reactive nitrogen intermediates and endogenous TNF. *J. Immunol.* 1998; 161:2383-2390.

(28) Santos L L, Morand E F, Holdsworth S R Suppression of adjuvant arthritis and synovial macrophage inducible nitric oxide by N-iminoethyl-1-ornithine, a nitric oxide synthase inhibitor. *Inflammation* 1997; 21:299-311.

The invention claimed is:

1. A method of inhibiting activity of MIF comprising contacting MIF with an MIF activity-inhibiting effective amount of a compound of formula (I), or a pharmaceutically acceptable salt thereof

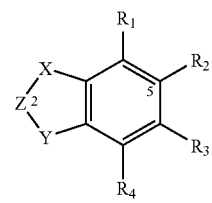

(I)

wherein

X is —N($R_6$)—;

Y is —N($R_7$)—;

Z is —C(O)—;

$R_1$ is selected from hydrogen, or $(CR_5R_{5'})_n$halo;

$R_2$ is selected from the group consisting of $C_1$-$C_{20}$alkyl, $C_2$-$C_{20}$alkenyl, $C_2$-$C_{20}$alkynyl, $(CR_{12}R_{12'})_m C(O)R_8$, $(CR_{12}R_{12'})_m C(S)R_8$, $(CR_{12}R_{12'})_m S(O)R_8$, $(CR_{12}R_{12'})_m S(O)_2 R_8$, $(CR_{12}R_{12'})_m OR_9$, $(CR_{12}R_{12'})_m SR_9$, $(CR_{12}R_{12'})_n NR_{10}R_{11}$, $(CR_{12}R_{12'})_m C(=NR_{24})R_{22}$ and $(CR_{12}R_{12'})_m R_{13}$;

$R_3$ is selected from hydrogen, $C_1$-$C_6$alkyl, $(CR_{16}R_{16'})_p NR_{14}R_{15}$, $(CR_{16}R_{16'})_p OR_{17}$, $(CR_{16}R_{16'})_p$halo, and $(CR_{16}R_{16'})_p NO_2$ $R_4$ is hydrogen, or halogen;

Each $R_5$ and $R_{5'}$ is independently hydrogen, $R_6$ is hydrogen, or $C_1$-$C_3$alkyl;

$R_7$ is hydrogen or $C_1$-$C_3$alkyl;

$R_8$ is selected from the group consisting of hydrogen, $C_1$-$C_{20}$alkyl, $C_2$-$C_{20}$alkenyl, $C_2$-$C_{20}$alkynyl, $OR_{19}$, $SR_{19}$, $N(R_{20})_2$, [NH—CH($R_{21}$)—C(O)]$_q$—$OR_{29}$, pyranosyl and $(CR_{12}R_{12'})_r R_{13}$;

$R_9$ is hydrogen;

$R_{10}$ and $R_{11}$ are independently selected from hydrogen, and C(O)$R_{23}$;

Each $R_{12}$ and $R_{12'}$ is independently hydrogen;

$R_{13}$ is selected from $OR_{25}$, $SR_{25}$, halo, $N(R_{25})_2$, and C(O)$R_{31}$;

$R_{14}$ and $R_{15}$ are each hydrogen;

Each $R_{16}$ and $R_{16'}$ is hydrogen;

$R_{17}$ is hydrogen;

$R_{19}$ and each $R_{20}$ are independently selected from hydrogen, $C_1$-$C_{20}$alkyl, and, $(CR_{26}R_{26'})_r R_{27}$;

$R_{21}$ is the characterising group of an amino acid wherein the amino acid is alanine, phenylalanine, serine, homoserine or norvaline;

$R_{22}$ is $NH(C_{1-6}alkyl)$;

$R_{23}$ is $(CR_{26}R_{26'})_tR_{27}$;

Each $R_{24}$ is independently selected from hydrogen and $C_1$-$C_6$alkyl;

Each $R_{25}$ is independently selected from hydrogen, and $C_1$-$C_6$alkyl;

Each $R_{26}$ and $R_{26'}$ is independently hydrogen;

$R_{27}$ selected from, $OR_{30}$, $SR_{30}$, and aryl;

Each $R_{29}$ is independently selected from hydrogen and $C_1$-$C_3$alkyl;

Each $R_{30}$ is independently selected from, $C_1$-$C_3$alkyl, and heterocyclyl;

$R_{31}$ is heterocyclyloxy;

n is 0 or an integer from 1 to 3;

m is 0 or an integer from 1 to 20;

p is 0 or an integer from 1 to 6;

q is an integer from 1 to 5;

t is an integer from 1 to 10;

wherein alkyl, alkenyl, alkynyl, aryl and heterocyclyl may be optionally substituted.

2. A method according to claim 1 wherein X is —N(H)—, Y is —N(H)—, and Z is —C(O)—.

3. A method according to claim 1 wherein the compound of formula 1 is selected from the group consisting of: benzimidazole-2-one-5-n-pentanoate, 5-[2-(1-oxy-2-hydroxyethyl)ethyl]benzimidazol-2-one-5-carboxylate, benzimidazole-2-one-5-methanoate, benzimidazole-2-one-5-ethanoate, 3,4,5-tris(acetyloxy)-6-[(acetyloxy)methyl]tetrahydro-2H-pyran-2-yl-benzimidazole-2-one-5-carboxylate, 5-bromo-6-methylbenzimidazol-2-one, 5-hydroxy-6-methylbenzimidazol-2-one, 5-dodecanylbenzoimidazol-2-one, 4,5,7-tribromo-6-methylbenzimidazol-2-one, 4,5,6,7-tetrabromobenzimidazol-2-one, 5-methyl-6-nitrobenzimidazol-2-one, 5-amino-6-methylbenzimidazol-2-one, N-(6-methylbenzimidazol-5-yl)-2-pyrimidin-2-yl-sulfanyl-acetamide, pentyl-benzimidazol-2-one-5-carbothioate, 5-(benzimidazol-2(3H)-one-6-yl)-5-oxopentanoic acid, 2(3H)-benzimidazolone-5-sulfonic acid pentyl ester, 2(3H)-benzimidazolone-5-sulfonic acid pentyl amide, N-butyl-2-oxo-2,3-dihydro-1H-1,3-benzimidazole-5-carboximidamide, 5-heptanoylbenzofuran-2(3H)-one, methyl 3-hydroxy-2-{[(2-oxo-2,3-dihydro-1H-1,3-benzimidazol-5-yl)carbonyl]amino}propanoate, 3-hydroxy-2-{[(2-oxo-2,3-dihydro-1H-1,3-benzimidazol-5-yl)carbonyl]amino}propanoic acid, methyl 2-{[(2-oxo-2,3-dihydro-1H-1,3-benzimidazol-5-yl)carbonyl]amino}-3-phenyl propanoate, 2-{[(2-oxo-2,3-dihydro-1H-1,3-benzimidazol-5-yl)carbonyl]amino}-3-phenyl propanoic acid, and N-(3,4-dihydroxyphenethyl)-2-oxo-2,3-dihydro-1H-1,3-benzimidazole-5-carboxamide.

4. A method of treating rheumatoid arthritis wherein MIF activity is implicated comprising the administration of a treatment effective amount of a compound of formula (I) as defined in claim 1 or a pharmaceutically acceptable salt thereof to a subject in need thereof.

5. A method of claim 4 wherein the subject is a human subject.

6. A method of treating rheumatoid arthritis wherein MIF activity is implicated comprising: administering to a mammal a compound of formula (I) as defined in claim 1 or a pharmaceutically acceptable salt thereof and a second therapeutic agent.

7. A method according to claim 6 wherein the second therapeutic agent is a glucocorticoid.

8. A method of treatment of rheumatoid arthritis for which treatment with a glucocorticoid is indicated, said method comprising: administering to a mammal a glucocorticoid and a compound of formula (I) as defined in claim 1 or a pharmaceutically acceptable salt thereof.

9. A method of treating a steroid-resistant rheumatoid arthritis comprising: administering to a mammal a glucocorticoid and a compound of formula (I) as defined in claim 1 or a pharmaceutically acceptable salt thereof.

10. A method according to claim 1 wherein $R_1$ is hydrogen or $(CR_5R_{5'})_n$halo;

$R_2$ is selected from $C_{1-20}$alkyl, $(CR_{12}R_{12'})_mC(O)R_8$, $(CR_{12}R_{12'})_mS(O)_2R_8$, $(CR_{12}R_{12'})_nNR_{10}R_{11}$, $(CR_{12}R_{12'})_m C(=NR_{24})R_{22}$ and $(CR_{12}R_{12'})_mR_{13}$;

$R_3$ is selected from hydrogen, $C_{1-6}$alkyl, $(CR_{16}R_{16'})_pNR_{14}R_{15}$, $(CR_{16}R_{16'})_pOR_{17}$, $(CR_{16}R_{16'})_p$halo and $(CR_{16}R_{16'})_pNO_2$;

$R_4$ is hydrogen or halogen;

Each $R_5$ and $R_{5'}$ is independently hydrogen;

$R_8$ is selected from $C_1$-$C_{20}$alkyl, $OR_{19}$, $SR_{19}$, $N(R_{20})_2$, [NH—CH($R_{21}$)—C(O)]$_q$—$OR_{29}$, pyranosyl and $(CR_{12}R_{12'})R_{13}$;

$R_9$ is hydrogen;

$R_{10}$ and $R_{11}$ are independently selected from hydrogen and $C(O)R_{23}$;

Each $R_{12}$ and $R_{12'}$ is independently hydrogen;

$R_{13}$ is selected from $OR_{25}$, $SR_{25}$, halo, $N(R_{25})_2$ and $C(O)R_{31}$;

$R_{14}$ and $R_{15}$ are each hydrogen;

Each $R_{16}$ and $R_{16'}$ is hydrogen;

$R_{17}$ is hydrogen;

$R_{19}$ and each $R_{20}$ are independently selected from hydrogen, $C_1$-$C_{20}$alkyl, and $(CR_{26}R_{26'})_tR_{27}$;

$R_{21}$ is the characterising group of phenylalanine or serine;

$R_{22}$ is $NH(C_{1-6}alkyl)$;

$R_{23}$ is $(CR_{26}R_{26'})_tR_{27}$;

Each $R_{24}$ is independently selected from hydrogen and $C_1$-$C_6$alkyl;

Each $R_{25}$ is independently selected from hydrogen and $C_1$-$C_6$alkyl;

Each $R_{26}$ and $R_{26'}$ is independently hydrogen;

$R_{27}$ is selected from $OR_{30}$, $SR_{30}$ and aryl;

Each $R_{29}$ is independently selected from $C_1$-$C_3$alkyl and heterocyclyl; and $R_{31}$ is heterocyclyloxy.

11. A method according to claim 10 wherein n is 0;

m is 0;

p is 0;

q is 0; and t is 1 or 2.

12. A method according to claim 1 wherein the compound of formula (I) is benzimidazole-2-one-5-n-pentanoate.

* * * * *